United States Patent
Gu et al.

(10) Patent No.: US 10,668,164 B2
(45) Date of Patent: Jun. 2, 2020

(54) IMMUNOGENIC GLYCOPROTEIN CONJUGATES

(71) Applicant: PFIZER INC., New York, NY (US)

(72) Inventors: Jianxin Gu, Paramus, NJ (US); Rajesh Kumar Kainthan, Tappan, NY (US); Jin-Hwan Kim, Suffern, NY (US); Avvari Krishna Prasad, Chapel Hill, NC (US); Yu-Ying Yang, Stamford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/118,038

(22) PCT Filed: Feb. 6, 2015

(86) PCT No.: PCT/IB2015/050919
§ 371 (c)(1),
(2) Date: Aug. 10, 2016

(87) PCT Pub. No.: WO2015/121783
PCT Pub. Date: Aug. 20, 2015

(65) Prior Publication Data
US 2017/0007713 A1    Jan. 12, 2017

Related U.S. Application Data

(60) Provisional application No. 61/939,845, filed on Feb. 14, 2014.

(51) Int. Cl.
*A61K 47/64* (2017.01)
*A61K 39/09* (2006.01)
*A61K 39/00* (2006.01)

(52) U.S. Cl.
CPC ........ *A61K 47/6415* (2017.08); *A61K 39/092* (2013.01); *A61K 47/646* (2017.08); *A61K 2039/6037* (2013.01)

(58) Field of Classification Search
None
See application file for complete search history.

(56) References Cited

U.S. PATENT DOCUMENTS

| | | | |
|---|---|---|---|
| 4,708,871 | A | 11/1987 | Geysen |
| 4,709,017 | A | 11/1987 | Collier et al. |
| 4,912,094 | A | 3/1990 | Myers |
| 4,950,740 | A | 8/1990 | Greenfield et al. |
| 5,843,711 | A | 12/1998 | Collier et al. |
| 5,917,017 | A | 6/1999 | Collier et al. |
| 6,027,925 | A | 2/2000 | Pollack et al. |
| 6,455,673 | B1 | 9/2002 | Collier |
| 2007/0141077 | A1 | 6/2007 | Pavliak et al. |

FOREIGN PATENT DOCUMENTS

| | | |
|---|---|---|
| EP | 0378881 | 7/1990 |
| EP | 0427347 | 5/1991 |
| EP | 0471177 | 2/1992 |
| EP | 0594610 | 5/1994 |
| WO | WO 90/14837 | 12/1990 |
| WO | WO 91/01146 | 2/1991 |
| WO | WO 92/19265 | 11/1992 |

(Continued)

OTHER PUBLICATIONS

Anderson, P., et al., "Immunization of 2-month-old infants with protein-coupled oligosaccharides derived from the capsule of Haemophilus influenzae type b", J. Pediatr, 1985, 107:346-351.

Baraldo, K., et al., "N19 Polyepitope as a Carrier for Enhanced Immunogenicity and Protective Efficacy of Meningococcal Conjugate Vaccines", Infection and Immunity, 2004, vol. 72, No. 8, 4884-4887.

Bergmann, C., et al., "An endogenously synthesized decamer peptide efficiently primes cytotoxic T cells specific for the HIV-1 envelope glycoprotein*", Eur. J. Immunol., 1993, 23:2777-2781.

Bergmann, C., et al., "Flanking Residues Alter Antigenicity and Immunogenicity of Multi-Unit CTL Epitopes", The Journal of Immunology, 1996, 157:3242-3249.

(Continued)

*Primary Examiner* — Patricia Duffy
(74) *Attorney, Agent, or Firm* — Keith D. Hutchinson; Matthew J. Pugmire

(57) ABSTRACT

The present invention relates generally to glycoconjugates comprising a saccharide covalently conjugated to a carrier protein through a spacer containing ((2-oxoethyl)thio)). In an aspect the invention provides oxo-eT linked glycoconjugates comprising a saccharide covalently conjugated to a carrier protein through a ((2-oxoethyl)thio) spacer having the formula (I): (I) wherein: A is a group $(C=X)_m$ wherein X is S or O and m is 0 or 1; B is a bond, O, or $CH_2$; and when m is 0, B can also be $(C=O)$; R is a $C_2$-$C_{16}$ alkylene, $C_2$-$C_{16}$ heteroalkylene, NH—C(=O)—$C_2$-$C_{16}$ alkylene, or NH—C(=O)—$C_2$-$C_{16}$ heteroalkylene, wherein said alkylene and heteroalkylene are optionally substituted by 1, 2 or 3 groups independently selected from COOR' where R' is selected from H, methyl, ethyl or propyl. The invention further relates to immunogenic compositions comprising such glycoconjugates, and to methods for the preparation and use of such glycoconjugates and immunogenic compositions.

(I)

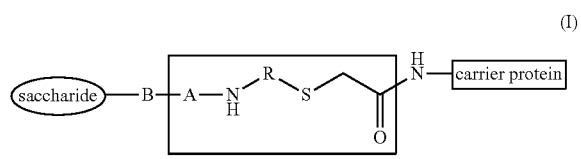

12 Claims, 8 Drawing Sheets

(56) References Cited

FOREIGN PATENT DOCUMENTS

| WO | WO 93/13302 | 7/1993 |
|---|---|---|
| WO | WO 93/17712 | 9/1993 |
| WO | WO 94103208 | 2/1994 |
| WO | WO 98158668 | 12/1998 |
| WO | WO 00/18434 | 4/2000 |
| WO | WO 00/37105 | 6/2000 |
| WO | WO 00/39299 | 7/2000 |
| WO | WO 00/56357 | 9/2000 |
| WO | WO 00/61761 | 10/2000 |
| WO | WO 01/72337 | 10/2001 |
| WO | WO 01/98334 | 12/2001 |
| WO | WO 02/091998 | 11/2002 |
| WO | WO 02/098368 | 12/2002 |
| WO | WO 02/098369 | 12/2002 |
| WO | WO 03/54007 | 7/2003 |
| WO | WO 2004/083251 | 9/2004 |
| WO | WO 04081515 | 9/2004 |
| WO | WO 05/033148 | 4/2005 |
| WO | WO 2006/110381 | 10/2006 |
| WO | 2007/071707 * | 6/2007 |
| WO | WO2007071707 | 6/2007 |
| WO | WO 2007/127668 | 11/2007 |
| WO | WO 2008/157590 | 12/2008 |
| WO | WO2009/000826 | 12/2008 |
| WO | WO2014027302 | 2/2014 |

OTHER PUBLICATIONS

Chiavolini, D., et al., "Animal Models of *Streptococcus pneumoniae* Disease", Clin. Micro. Rev., 2008, pp. 666-685, vol. 21, No. 4.

Doe, B., et al., "Induction of HIV-1 envelope (gp120)-specific cytotoxic T lymphocyte responses in mice by recombinant CHO cell-derived gp120 is enhanced by enzymatic removal of N-linked glycans", Eur. J. Immunol., 1994, 24:2369-2376.

Erickson, A., et al., "Hepatitis C Virus-Specific CTL Responses in the Liver of Chimpanzees with Acute and Chronic Hepatitis C", The Journal of Immunology, 1993, pp. 4189-4199, vol. 151, No. 8.

Falugi, F., et al., "Rationally designed strings of promiscuous CD4+ T cell epitopes provide help to Haemophilus influenzae type b oligosaccharide: a model for new conjugate vaccines," Eur. J. Immunology, 2001, vol. 31, 3816-3824.

Fournier, J., et al., "Isolation of Type 5 capsular Polysaccharide", Ann. Inst. Pasteur/Microbiol., 1987, pp. 561-567, vol. 138.

Geysen, H. M., et al., "A Priori Delineation of a Peptide which Mimics a Discontinuous Antigenic Determinant", Molecular Immunol., 1986, pp. 709-715, vol. 23, No. 7.

Geysen, H.M., et al., "Use of peptide synthesis to probe viral antigens for epitopes to a resolution of a single amino acid," Proc. Natl. Acad. Sci., 1984, pp. 3398-4002, vol. 81.

Hestrin, S., "The Reaction of Acetylcholine and other Carboxylic Acid Derivatives with Hydroxylamine, and its Analytical Application", J. Biol. Chem., 1949, 180:249-261.

Hu, B., et al., "Approach to Validating an Opsonophagocytic Assay for *Streptococcus pneumoniae*", Clin. and Diag. Lab. Immun., 2005, p. 287-295, vol. 12, No. 2.

Jones, C., et al., "Use and validation of NMR assays for the identity and O-acetyl content of capsular polysaccharides from Neisseria meningitidis used in vaccine manufacture", Journal of Pharm. and Biomed. Anal., 2002, 30:1233-1247.

Kuo, J., et al., "Characterization of a Recombinant Pneumolysin and Its Use as a Protein Carrier for Pneumococcal Type 18C Conjugate Vaccines," Infection and Immunity, 1995, vol. 63, No. 7, 2706-2713.

Lemercinier, X., et al., "Full 1H NMR assignment and detailed O-acetylation patterns of capsular polysaccharides from Neisseria meningitidis used in vaccine production", Carbohydrate Research, 1996, 296:83-96.

Sau S., et al., "The *Staphylococcus aureus* allelic genetic loci for serotype 5 and 8 capsule expression contain the type-specific genes flanked by common genes", Microbiology, 1997, 143:2395-2405.

Schneerson, R., et al., Serum Antibody Responses of Juvenile and Infant Rhesus Monkey's Injected with Haemophilus influenzae Type b and Pneumococcus Type 6A Capsular Polysaccharide-Protein Conjugates, Infection and Immunity, 1984, pp. 582-591, vol. 45, No. 3.

Suhrbier, A., "Multi-epitope DNA vaccines", Immunol. and Cell Biol., 1997, 75:402-408.

Uchida, T., et al., "Diphtheria Toxin and Related Proteins," The Journal of Biological Chemistry, 1973, vol. 248, No. 11, 3838-3844.

Douglas, C., et al., "Exotoxin A of Pseudomonas aeruginosa: Substitution of Glutamic Acid 553 with Aspartic Acid Drastically Reduces Toxicity and Enzymatic Activity," 1987, J. Bacterial, 169:4967-4971.

Morris, G., "Epitope Mapping Protocols in Methods in Molecular Biology", vol. 66, 1996, Humana Press.

International Search Report, PCT/IB2015/050919, dated Feb. 6, 2015.

* cited by examiner

General scheme for the preparation of oxo-eTAC linked glycoconjugates (ETAC/CDT Hydroxyl Activation (eTAC))

General scheme for the preparation of oxo-eTAAN linked glycoconjugates

General scheme for the preparation of oxo-eTAAD linked glycoconjugates

General scheme for the preparation of oxo-eTAAD linked glycoconjugates, using thiazolidinonethione derivative (ETAAD – Thiazolidinone )

IMMUNOGENIC GLYCOPROTEIN CONJUGATES

CROSS REFERENCE TO RELATED APPLICATIONS

This application is a National Stage Application of International Application No. PCT/IB2015/050919, filed Feb. 6, 2015, which claims the benefit under 35 U.S.C. § 119(e) of U.S. Provisional Application Ser. No. 61/939,845, filed Feb. 14, 2014, both of which are incorporated by reference in their entirety.

FIELD OF THE INVENTION

The invention relates generally to glycoconjugates comprising a saccharide covalently conjugated to a carrier protein through a spacer containing ((2-oxoethyl)thio) ("oxo-eT" thereafter) having the general formula (I)

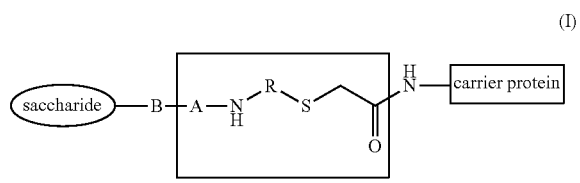

wherein B, A and R have the meaning indicated below, to immunogenic compositions comprising such glycoconjugates, and to methods for the preparation and use of such glycoconjugates and immunogenic compositions.

In an embodiment, said spacer is not the (2-((2-oxoethyl)thio)ethyl)carbamate (eTEC) spacer.

BACKGROUND OF THE INVENTION

The approach to increasing immunogenicity of poorly immunogenic molecules by conjugating these molecules to "carrier" molecules has been utilized successfully for decades (see, e.g., Goebel et al. (1939) J. Exp. Med. 69: 53). For example, many immunogenic compositions have been described in which purified capsular polymers have been conjugated to carrier proteins to create more effective immunogenic compositions by exploiting this "carrier effect." Schneerson et al. (1984) Infect. Immun. 45: 582-591). Conjugation has also been shown to bypass the poor antibody response usually observed in infants when immunized with a free polysaccharide (Anderson et al. (1985) J. Pediatr. 107: 346; Insel et al. (1986) J. Exp. Med. 158: 294).

Conjugates have been successfully generated using various cross-linking or coupling reagents, such as homobifunctional, heterobifunctional, or zero-length crosslinkers. Many methods are currently available for coupling immunogenic molecules, such as saccharides, proteins, and peptides, to peptide or protein carriers. Most methods create amine, amide, urethane, isothiourea, or disulfide bonds, or in some cases thioethers. A disadvantage to the use of cross-linking or coupling reagents which introduce reactive sites into the side chains of reactive amino acid molecules on carrier and/or immunogenic molecules is that the reactive sites, if not neutralized, are free to react with any unwanted molecule either in vitro (thus potentially adversely affecting the functionality or stability of the conjugates) or in vivo (thus posing a potential risk of adverse events in persons or animals immunized with the preparations). Such excess reactive sites can be reacted or "capped", so as to inactivate these sites, utilizing various known chemical reactions, but these reactions may be otherwise disruptive to the functionality of the conjugates. This may be particularly problematic when attempting to create a conjugate by introducing the reactive sites into the carrier molecule, as its larger size and more complex structure (relative to the immunogenic molecule) may render it more vulnerable to the disruptive effects of chemical treatment. Thus, there remains a need for new methods to prepare appropriately capped carrier protein conjugates, such that the functionality of the carrier is preserved and the conjugate retains the ability to elicit the desired immune response.

SUMMARY OF THE INVENTION

The present invention relates generally to glycoconjugates comprising a saccharide covalently conjugated to a carrier protein through a spacer containing ((2-oxoethyl)thio)) (also named "oxo-eT" thereafter).

In an aspect, the present invention relates to glycoconjugates comprising a saccharide covalently conjugated to a carrier protein through a spacer containing ((2-oxoethyl)thio) having the general formula (I):

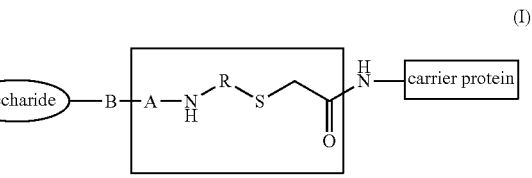

wherein:
A is a group $(C=X)_m$ wherein X is S or O and m is 0 or 1;
B is a bond, O, or $CH_2$; and when m is 0, B can also be (C=O);
R is a $C_2$-$C_{16}$ alkylene, $C_2$-$C_{16}$ heteroalkylene, NH—C(=O)—$C_2$-$C_{16}$ alkylene, or NH—C(=O)—$C_2$-$C_{16}$ heteroalkylene, wherein said alkylene and heteroalkylene are optionally substituted by 1, 2 or 3 groups independently selected from COOR' where R' is selected from H, methyl, ethyl or propyl.

In the above general formula (I), $C_2$-$C_{16}$ alkylene denotes a straight-chain containing 2 to 16 carbon atoms. Examples of suitable ($C_2$-$C_{16}$) alkylene radicals are $(CH_2)_2$, $(CH_2)_3$, $(CH_2)_4$, $(CH_2)_5$, $(CH_2)_6$, $(CH_2)_7$, $(CH_2)_8$, $(CH_2)_9$ or $(CH_2)_{10}$.

In the above general formula (I), heteroalkylene refers to an alkylene group as defined herein in which one or more of the carbon atoms is each independently replaced with the same or different heteroatom selected from O, S or N. In a preferred embodiment, heteroalkylene refers to an alkylene group as defined herein in which one or more of the carbon atoms is each replaced with an oxygen atom. In a preferred embodiment, heteroalkylene refers to an alkylene group as defined herein in which 1, 2, 3 or 4 of the carbon atoms is each replaced with an oxygen atom. Example of suitable $C_2$-$C_{16}$ heteroalkylene are O—$CH_2$, O—$CH_2$—$CH_2$, $CH_2$—$CH_2$—O—$CH_2$—$CH_2$, O—$CH_2$—$CH_2$—O—$CH_2$—$CH_2$, O—$CH_2$—$CH_2$—O—$CH_2$—$CH_2$—O—$CH_2$—$CH_2$, O—$CH_2$—$CH_2$—(N—$CH_3$)—$CH_2$—$CH_2$—O—$CH_2$—$CH_2$, $CH_2$—$CH_2$—(N—$CH_3$)—$CH_2$—$CH_2$, $CH_2$—$CH_2$—S—$CH_2$—$CH_2$ . . . .

In a preferred embodiment,
B is O and A is C(=O), or,
B is $CH_2$ and m is 0, or, B is C(=O) and m is 0, and/or R is a $C_2$-$C_{10}$ alkylene, $C_2$-$C_{10}$ heteroalkylene, NH—C(=O)—$C_2$-$C_{10}$ alkylene, or NH—C(=O)—$C_2$-$C_{10}$ heteroalkylene, wherein said alkylene and heteroalkylene are optionally substituted by 1, 2 or 3 groups independently selected from COOR' where R' is selected from H, methyl, ethyl or propyl, or, R is a $C_2$-$C_{10}$ alkylene, $C_2$-$C_{10}$ heteroalkylene, NH—C(=O)—$C_2$-$C_{10}$ alkylene, or NH—C(=O)—$C_2$-$C_{10}$ heteroalkylene, wherein said alkylene and heteroalkylene are optionally substituted by COOH.

In other preferred embodiments,

B is O and A is C(=O), or,

B is CH2 and m is 0, or,

B is C(=O) and m is 0, and/or

R is selected from the groups consisting of $(CH_2)_2$, $(CH_2)_3$, $(CH_2)_4$, $(CH_2)_5$, $(CH_2)_6$, $(CH_2)_7$, $(CH_2)_8$, $(CH_2)_9$ or $(CH_2)_{19}$.

In other preferred embodiments,

B is O and A is C(=O), or,

B is CH2 and m is 0, or,

B is C(=O) and m is 0, and/or

R is selected from the groups consisting of O—$CH_2$, O—$CH_2$—$CH_2$, $CH_2$—$CH_2$—O—$CH_2$—$CH_2$, O—$CH_2$—$CH_2$—O—$CH_2$—$CH_2$, CO—$CH_2$—$CH_2$—O—$CH_2$—$CH_2$—O—$CH_2$—$CH_2$, CO—$CH_2$—$CH_2$—(N—$CH_3$)—$CH_2$—$CH_2$—O—$CH_2$—$CH_2$, $CH_2$—$CH_2$—(N—$CH_3$)—$CH_2$—$CH_2$ and $CH_2$—$CH_2$—S—$CH_2$—$CH_2$.

In an embodiment, the glycoconjugates of the present invention comprise a saccharide covalently conjugated to a carrier protein through a spacer containing ((2-oxoethyl)thio) (also named or "oxo-eT" thereafter) with the provisio that said spacer is not the (2-((2-oxoethyl)thio)ethyl)carbamate (eTEC) spacer (i.e., —C(O)NH(CH$_2$)$_2$SCH$_2$C(O)—).

The invention further relates to immunogenic compositions comprising such glycoconjugates, and to methods for the preparation and use of such glycoconjugates and immunogenic compositions.

In an aspect, the present invention is directed towards methods of making glycoconjugates comprising a saccharide covalently conjugated to a carrier protein through a bivalent, heterobifunctional linker referred to herein as a ((2-oxoethyl)thio) or "oxo-eT" spacer.

In some embodiments, the oxo-eT linked glycoconjugates of the invention have the following formulas 1. a (((2-oxoethyl)thio)alkyl)carbamate (oxo-eTAC) linked glycoconjugate having formula (II)

(II)

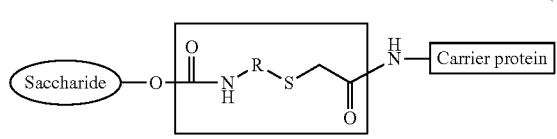

wherein R is $(CH_2)_n$ where n is 3 to 10;

2. a (((2-oxoethyl)thio)alkyl)carbamate (oxo-eTAC) linked glycoconjugate, having the following formula (III):

(III)

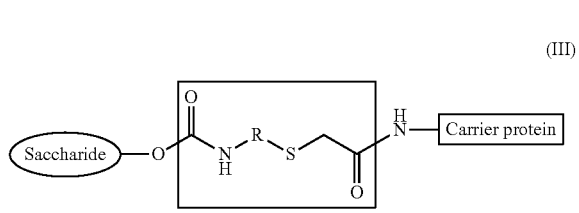

wherein R is selected from $(CH_2CH_2O)_mCH_2CH_2$, $CH(COOH)(CH_2)_n$, $NHCO(CH_2)_n$, $NHCO(CH_2CH_2O)_mCH_2CH_2$, $OCH_2(CH_2)_n$ or $O(CH_2CH_2O)_mCH_2CH_2$;

wherein n is selected from 1 to 10 and m is selected from 1 to 4.

3. a (((2-oxoethyl)thio)alkyl)amine (oxo-eTAAN) linked glycoconjugate having formula (IV):

(IV)

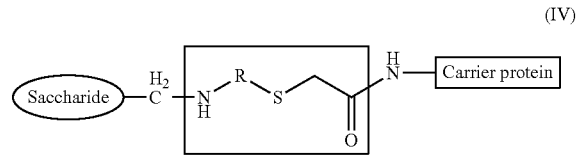

wherein R is selected from $CH_2(CH_2)_n$, $(CH_2CH_2O)_mCH_2CH_2$, $CH(COOH)(CH_2)_n$, $NHCO(CH_2)_n$, $NHCO(CH_2CH_2O)_mCH_2CH_2$, $OCH_2(CH_2)_n$ or $O(CH_2CH_2O)_mCH_2CH_2$;

wherein n is selected from 1 to 10 and m is selected from 1 to 4;

4. a (((2-oxoethyl)thio)alkyl)amide (oxo-eTAAD) linked glycoconjugate having formula (V)

(V)

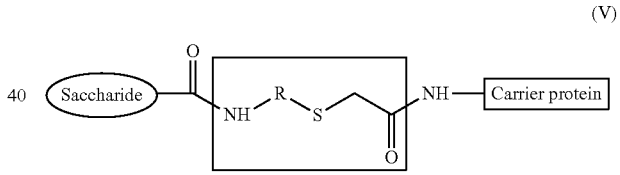

wherein R is selected from $CH_2(CH_2)_1$, $(CH_2CH_2O)_mCH_2CH_2$, $CH(COOH)(CH_2)_1$, $NHCO(CH_2)_1$, $NHCO(CH_2CH_2O)_mCH_2CH_2$, $OCH_2(CH_2)_n$ or $O(CH_2CH_2O)_mCH_2CH_2$;

wherein n is selected from 1 to 10 and m is selected from 1 to 4.

In a preferred embodiment, the invention relates to a glycoconjugates of formula (I), (II), (III) (IV) or (V) where R is selected from $(CH2)_n$ wherein n is selected from 3 to 10;

$(CH_2CH_2O)_mCH_2CH_2$ wherein m is selected from 1 to 3;

$CH(COOH)(CH_2)_n$ wherein n is selected from 1 to 8;

$NHCO(CH_2)_n$ wherein n is selected from 1 to 8;

$NHCO(CH_2CH_2O)_mCH_2CH_2$ wherein m is 1 or 2, $OCH_2(CH_2)_n$ wherein n is selected from 1 to 8, or, —$O(CH2CH_2O)_mCH_2CH_2$ wherein m is 1 or 2.

In the above defined glycoconjugates comprising a spacer containing ((2-oxoethyl)thio) as part of the structural linkage between a saccharide and a carrier protein or peptide, said spacer provides stable thioether and amide bonds.

The glycoconjugates of the present invention comprise a spacer containing ((2-oxoethyl)thio) as part of the structural linkage between a saccharide and a carrier protein or peptide, said spacer provides stable thioether and amide bonds. Additionally, it is preferred that said spacer is relatively short so as to lower the risk of generating an immune response against the spacer part of the conjugate. An immune response against the spacer part of the conjugate is not desirable and a short spacer has the benefit of minimizing said risk. Therefore in an embodiment, the glycoconjugates of the present invention comprise a spacer containing ((2-oxoethyl)thio) where the number of atoms of that spacer (e.g. contained in the central box of formulas I, II, III, IV or V) is 25 atoms or less. Preferably, the number of atoms of that spacer (e.g. contained in the central box of formulas I, II, III, IV or V) is 21, 20, 19, 18, 17, 16, 15, 14, 13, 12, 11, 10, 9, 8, 7, or 6 atoms. Even more preferably, the number of atoms of that spacer (e.g. contained in the central box of formulas I, II, III, IV or V) is 15 or less (such as 14, 13, 12, 11, 10, 9, 8, 7, or 6 atoms).

The invention further provides oxo-eT linked glycoconjugates, immunogenic compositions comprising them, and methods for the use of such glycoconjugates and immunogenic compositions.

In one aspect, the invention provides a glycoconjugate comprising a saccharide conjugated to a carrier protein through an oxo-eTAC spacer, wherein the saccharide is covalently linked to the oxo-eTAC spacer through a carbamate linkage, and wherein the carrier protein is covalently linked to the oxo-eTAC spacer through a thioether and amide linkage. In an embodiment, said oxo-eTAC spacer is not the (2-((2-oxoethyl)thio)ethyl)carbamate (eTEC) spacer (i.e., —C(O)NH(CH2)2SCH2C(O)—).

In one aspect, for the generation of oxo-eTAC spacer in the conjugate, the preferred linkers used herein are Mercaptopropionylhydrazide (MPH, n=2), L-Cystine dimethylester dihydrochloride (n=1), and 2-(2-aminoethoxy)ethane-1-thiol (AEET, n=2) and 4-Amino-1-butanethiol hydrochloride (n=4).

In another aspect, the invention provides a glycoconjugate comprising a saccharide conjugated to a carrier protein through an oxo-eTAAN spacer, wherein the saccharide is covalently linked to the oxo-eTAAN spacer through an amine linkage, and wherein the carrier protein is covalently linked to the oxo-eTAAN spacer through a thioether and amide linkage.

In another aspect, the invention provides a glycoconjugate comprising a saccharide conjugated to a carrier protein through an oxo-eTAAD spacer, wherein the saccharide is covalently linked to the oxo-eTAAD spacer through an amide linkage, and wherein the carrier protein is covalently linked to the oxo-eTAAD spacer through a thioether and amide linkage.

In some embodiments, the saccharide is a polysaccharide, such as a capsular polysaccharide derived from bacteria, in particular from pathogenic bacteria. In other embodiments, the saccharide is an oligosaccharide or a monosaccharide.

The carrier proteins incorporated into the glycoconjugates of the invention are selected from the group of carrier proteins generally suitable for such purposes, as further described herein or known to those of skill in the art. In particular embodiments, the carrier protein is $CRM_{197}$.

In another aspect, the invention provides a method of making a glycoconjugate comprising a saccharide conjugated to a carrier protein through an oxo-eTAC spacer, comprising the steps of: a) reacting a saccharide with a carbonic acid derivative or cyanogen derivative to produce an activated saccharide; b) reacting the activated saccharide with a bifunctional linker containing amine and thiol functionalities (as protected or free thiol forms, e.g. DL-cystine or DL-cysteine or a salt thereof, or mercaptopropionylhydrazide, or 2-(2-aminoethoxy)ethane-1-thiol, or 4-Amino-1-butanethiol or a salt thereof), to produce a thiolated saccharide; c) reacting the thiolated saccharide with a deprotecting or reducing agent (if thiol is protected) to produce an activated thiolated saccharide comprising one or more free sulfhydryl residues; d) reacting the activated thiolated saccharide with an activated carrier protein comprising one or more α-haloacetamide groups, to produce a thiolated saccharide-carrier protein conjugate; and e) reacting the thiolated saccharide-carrier protein conjugate with (i) a first capping reagent capable of capping unconjugated α-haloacetamide groups of the activated carrier protein; and/or (ii) a second capping reagent capable of capping unconjugated free sulfhydryl residues of the activated thiolated saccharide; whereby an oxo-eTAC linked glycoconjugate is produced.

In frequent embodiments, step a) is done in an organic solvent.

In frequent embodiments, the carbonic acid derivative is 1,1'-carbonyl-di-(1,2,4-triazole) (CDT) or 1,1'-carbonyldiimidazole (CDI) or disuccinimidyl carbonate (DSC) or N-hydroxysuccinimidyl chloroformate. Preferably, the carbonic acid derivative is CDT and the organic solvent is a polar aprotic solvent, such as dimethylsulfoxide (DMSO). In preferred embodiments, the thiolated saccharide is produced by reaction of the activated saccharide with a heterobifunctional thioalkylamine reagent or a salt thereof. The oxo-eTAC linked glycoconjugates produced by the methods of the invention may be represented by general formulas (II and III).

In frequent embodiments, the first capping reagent is N-acetyl-L-cysteine, which reacts with unconjugated α-haloacetamide groups on lysine residues of the carrier protein to form an S-carboxymethylcysteine (CMC) residue covalently linked to the activated lysine residue through a thioether linkage. In other embodiments, the second capping reagent is iodoacetamide (IAA), which reacts with unconjugated free sulfhydryl groups of the activated thiolated saccharide to provide a capped thioacetamide. Frequently, step e) comprises capping with both a first capping reagent and a second capping reagent. In certain embodiments, step e) comprises capping with N-acetyl-L-cysteine as the first capping reagent and IAA as the second capping reagent.

In some embodiments, the capping step e) further comprises reaction with a reducing agent, for example, DTT, TCEP, or mercaptoethanol, after reaction with the first and/or second capping reagent.

In some embodiments, step d) further comprises providing an activated carrier protein comprising one or more α-haloacetamide groups prior to reacting the activated thiolated saccharide with the activated carrier protein. In frequent embodiments, the activated carrier protein comprises one or more α-bromoacetamide groups.

In another aspect, the invention provides a method of making a glycoconjugate comprising a saccharide conjugated to a carrier protein through an oxo-eTAAN spacer, comprising the steps of: a) reacting a saccharide with an oxidizing reagent to generate aldehyde groups to produce an activated saccharide; b) reacting the activated saccharide with a bifunctional linker containing amine and thiol functionalities (in protected or free forms) from the amino end of the linker, to produce a thiolated saccharide by reductive amination; c) reacting the thiolated saccharide with a deprotecting agent or reducing agent (if thiol is protected) to produce an activated thiolated saccharide comprising one or more free sulfhydryl residues; d) reacting the activated thiolated saccharide with an activated carrier protein comprising one or more α-haloacetamide groups, to produce a thiolated saccharide-carrier protein conjugate; and e) reacting the thiolated saccharide-carrier protein conjugate with (i) a first capping reagent capable of capping unconjugated α-haloacetamide groups of the activated carrier protein; and/or (ii) a second capping reagent capable of capping unconjugated free sulfhydryl residues of the activated thiolated saccharide; whereby an oxo-eTAAN linked glycoconjugate is produced. The oxo-eTAAN linked glycoconjugates produced by the methods of the invention may be represented by general formula (IV).

In a preferred embodiment of the above for the generation of the thiolated polysaccharide, the primary hydroxyl groups of the polysaccharide are oxidized by 2,2,6,6-Tetramethyl-1-piperidinyloxy (TEMPO)/N-Chlorosuccinimide (NCS) reagent system (see FIG. 2 or application number PCT/IB2013/060933 which is incorporated herein by reference as if set forth in its entirety), prior to further reaction with the amino end of eTAAN linker.

In another aspect, the invention provides a method of making a glycoconjugate comprising a carboxyl containing saccharide conjugated to a carrier protein through an oxo-eTAAD spacer, comprising the steps of: a) first reacting the carboxyl group containing saccharide to generated an activated saccharide with a carbodiimide or a derivative thereof; b) reacting the activated saccharide with a heterobifunctional linker containing amine and thiol functionalities (in protected or free form) from the amino end, to produce a thiolated saccharide; c) reacting the thiolated saccharide with a deprotecting or reducing agent (if protected) to produce an activated thiolated saccharide comprising one or more free sulfhydryl residues; d) reacting the activated thiolated saccharide with an activated carrier protein comprising one or more α-haloacetamide groups, to produce a thiolated saccharide-carrier protein conjugate; and e) reacting the thiolated saccharide-carrier protein conjugate with (i) a first capping reagent capable of capping unconjugated α-haloacetamide groups of the activated carrier protein; and/or (ii) a second capping reagent capable of capping unconjugated free sulfhydryl residues of the activated thiolated saccharide; whereby an oxo-eTAAD linked glycoconjugate is produced.

In another aspect, the invention provides a method of making a glycoconjugate comprising a carboxyl functionalized saccharide conjugated to a carrier protein through an oxo-eTAAD spacer. As an example, the primary hydroxyl of the saccharide first could be converted to carboxyl by reaction with TEMPO/sodium hypochlorite.

In frequent embodiments, the carbodiimide derivative is 1-ethyl-3-(3-dimethylaminopropyl)carbodiimide (EDC), or N,N'-dicyclohexylcarbodiimide (DCC), or 1-cyclohexyl-3-(2-morpholinoethyl)carbodiimide. Preferably, the carbodiimide derivative is 1-ethyl-3-(3-dimethylaminopropyl)carbodiimide (EDC) and the organic solvent is a polar aprotic solvent, such as dimethylsulfoxide (DMSO). In preferred embodiments, the thiolated saccharide is produced by reaction of the activated saccharide with a a bifunctional linker containing amine and thiol functionalities. The oxo-eTAAD linked glycoconjugates produced by the methods of the invention may be represented by general formula (V) In a preferred embodiment of the above for the reaction of the carboxyl containing saccharide, the initial activation step is accomplished by carbodiimide and thiazolidinone thione, prior to the reaction with the amino end of the heterobifunctional eTAAD linker. In another embodiment the initial carboxylic acid activation step is accomplished by N-ethyl-3-phenylisoxazolium-3'-sulfonate (Woodward's reagent K) prior to reaction with the amino end of the bifunctional eTAAD linker.

In another aspect, the invention provides an oxo-eT linked glycoconjugate comprising a saccharide conjugated to a carrier protein through an oxo-eT spacer produced according to any of the methods disclosed herein.

For each of the aspects of the invention, in particular embodiments of the methods and compositions described herein, the oxo-eT linked glycoconjugate comprises a saccharide which is a bacterial capsular polysaccharide, in particular a capsular polysaccharide derived from pathogenic bacteria.

By way of example, the polysaccharide may be from Gram negative bacteria selected from the group consisting of: *Escherichia coli, Francisella tularensis, H influenzae, Klebsiella, Moraxella catarrhalis, Neisseria meningitidis, Porphyromonas-A-gingivalis, Pseudomonas aeruginosa, Burkholderia cepacia, Salmonella typhi, Salmonella typhimurium, Salmonella paratyphi, Shigella dysenteriae, Shigella flexneri, Shegella sonnei* and *Vibrio cholera*. The polysaccharide may be from Gram positive bacteria selected from the group consisting of: *Enterococcus faecalis, Enterococcus faecium*, Group A *Streptococcus*, Group B *Streptococcus, Mycobacterium tuberculosis, Staphylococcus aureus, Staphylococcus epidermidis* and *Streptococcus pneumoniae*.

In some embodiments, the oxo-eT linked glycoconjugate comprises a pneumococcal (Pn) capsular polysaccharide derived from *Streptococcus pneumoniae*. In specific embodiments, the Pn capsular polysaccharide is selected from the group consisting of Pn-serotype 1, 2, 3, 4, 5, 6A, 6B, 7F, 8, 9V, 9N, 10A, 11A, 12F, 14, 15A, 15B, 17F, 18C, 19A, 19F, 20, 22F, 23A, 23B, 23F, 33F and 35B capsular polysaccharides. In specific embodiments, the Pn capsular polysaccharide is selected from the group consisting of Pn-serotype 1, 3, 4, 5, 6A, 6B, 7F, 8, 9V, 10A, 11A, 12F, 14, 15B, 18C, 19A, 19F, 22F, 23F and 33F capsular polysaccharides. In specific embodiments, the Pn capsular polysaccharide is selected from the group consisting of Pn-serotype 2, 9N, 15A, 17F, 20, 23A, 23B and 35B capsular polysaccharides.

In other such embodiments, the oxo-eT linked glycoconjugate comprises a meningococcal (Mn) capsular saccharides (oligo or polysaccharide) derived from *Neisseria meningitidis*. In specific embodiments, the Mn capsular polysaccharide is selected from the group consisting of Mn-serotype A, C, W135 and Y capsular polysaccharides. In specific embodiments, the Mn capsular polysaccharide is Mn-serotype X capsular polysaccharide.

In other such embodiments, the oxo-eT linked glycoconjugate comprises a capsular polysaccharide derived from Group B *Streptococcus* (GBS). In specific embodiments, the GBS capsular polysaccharide is selected from the group consisting of serotype Ia, Ib, II, III or V capsular polysaccharides.

In other such embodiments, the oxo-eT linked glycoconjugate comprises a capsular polysaccharide derived from *Staphylococcus aureus*. In specific embodiments, the *S. aureus* capsular polysaccharide is *S. aureus* serotype 5 or 8 capsular polysaccharide.

In other such embodiments, the oxo-eT linked glycoconjugate comprises a capsular polysaccharide derived from an *Enterococcus* bacteria. In specific embodiments, the *Enterococcus* capsular polysaccharide is *Enterococcus faecalis* or *Enterococcus faecium* capsular polysaccharide.

In particularly preferred embodiments, the saccharide is a bacterial capsular polysaccharide, such as a Pn or Mn or GBS or *S. aureus* or *Enterococcus* capsular polysaccharide, covalently conjugated to $CRM_{197}$ through an oxo-eT spacer.

The compositions and methods described herein are useful in a variety of applications. For example, the glycoconjugates of the invention can be used in the production of immunogenic compositions comprising an oxo-eT linked glycoconjugate. Such immunogenic compositions can be used to protect recipients from bacterial infections, for example by pathogenic bacteria such as *S. pneumonia* or *N. meningitidis* or GBS or *S. aureus* or *Enterococcus*.

Thus, in another aspect, the invention provides an immunogenic composition comprising an oxo-eT linked glycoconjugate and a pharmaceutically acceptable excipient, carrier or diluent, wherein the glycoconjugate comprises a saccharide covalently conjugated to a carrier protein through an oxo-eT spacer, as described herein.

In frequent embodiments, the immunogenic composition comprises an oxo-eT linked glycoconjugate and a pharmaceutically acceptable excipient, carrier or diluent, wherein the glycoconjugate comprises a bacterial capsular polysaccharide.

In some such embodiments, the immunogenic composition comprises an oxo-eT linked glycoconjugate which comprises a Pn capsular polysaccharide derived from *S. pneumoniae*. In some specific embodiments, the Pn capsular polysaccharide is selected from the group consisting of Pn-serotype 1, 2, 3, 4, 5, 6A, 6B, 7F, 8, 9N, 9V, 10A, 11A, 12F, 14, 15A, 15B, 17F, 18C, 19A, 19F, 20, 22F, 23A, 23B, 23F, 33F and 35B capsular polysaccharides. In specific embodiments, the Pn capsular polysaccharide is selected from the group consisting of Pn-serotype 1, 3, 4, 5, 6A, 6B, 7F, 8, 9V, 10A, 11A, 12F, 14, 15B, 18C, 19A, 19F, 22F, 23F and 33F capsular polysaccharides. In specific embodiments, the Pn capsular polysaccharide is selected from the group consisting of Pn-serotype 2, 9N, 15A, 17F, 20, 23A, 23B and 35B capsular polysaccharides.

In other such embodiments, the immunogenic composition comprises an oxo-eT linked glycoconjugate which comprises a Mn capsular polysaccharide derived from *N. meningitidis*. In some specific embodiments, the Mn capsular polysaccharide is selected from the group consisting of Mn-serotype A, C, W135 and Y capsular polysaccharides. In specific embodiments, the Mn capsular polysaccharide is Mn-serotype X capsular polysaccharide.

In other such embodiments, the oxo-eT linked glycoconjugate comprises a capsular polysaccharide derived from Group B *Streptococcus* (GBS). In specific embodiments, the GBS capsular polysaccharide is selected from the group consisting of serotype Ia, Ib, II, III or V capsular polysaccharides.

In other such embodiments, the oxo-eT linked glycoconjugate comprises a capsular polysaccharide derived from *Staphylococcus aureus*. In specific embodiments, the *S. aureus* capsular polysaccharide is *S. aureus* serotype 5 or 8 capsular polysaccharide.

In other such embodiments, the oxo-eT linked glycoconjugate comprises a capsular polysaccharide derived from an *Enterococcus* bacteria. In specific embodiments, the *Enterococcus* capsular polysaccharide is *Enterococcus faecalis* or *Enterococcus faecium* capsular polysaccharide.

In preferred embodiments, the immunogenic composition comprises an oxo-eT linked glycoconjugate which comprises a bacterial capsular polysaccharide, such as a Pn or Mn or GBS or *S. aureus* or *Enterococcus* capsular polysaccharide, covalently conjugated to $CRM_{197}$ through an oxo-eT spacer.

In some embodiments, the immunogenic compositions comprise an adjuvant. In some such embodiments, the adjuvant is an aluminum-based adjuvant selected from the group consisting of aluminum phosphate, aluminum sulfate and aluminum hydroxide. In one embodiment, the immunogenic compositions described herein comprise the adjuvant aluminum phosphate.

In another aspect, the invention provides a method of preventing, treating or ameliorating a bacterial infection, disease or condition in a subject, comprising administering to the subject an immunologically effective amount of an immunogenic composition of the invention, wherein said immunogenic composition comprises an oxo-eT linked glycoconjugate comprising a bacterial antigen, such as a bacterial capsular polysaccharide.

In one embodiment, the infection, disease or condition is associated with *S. pneumonia* bacteria and the glycoconjugate comprises a Pn capsular polysaccharide. In another embodiment, the infection, disease or condition is associated with *N. meningitidis* bacteria and the glycoconjugate comprises a Mn capsular polysaccharide. In another embodiment, the infection, disease or condition is associated with Group B *Streptococcus* bacteria and the glycoconjugate comprises a GBS capsular polysaccharide. In another embodiment, the infection, disease or condition is associated with *S. aureus* bacteria and the glycoconjugate comprises a *S. aureus* capsular polysaccharide. In another embodiment, the infection, disease or condition is associated with *Enterococcus faecalis* or *Enterococcus faecium* and the glycoconjugate comprises respectively a *Enterococcus faecalis* or a *Enterococcus faecium* capsular polysaccharide.

In other aspects, the invention provides a method for inducing an immune response against pathogenic bacteria; a method for preventing, treating or ameliorating a disease or condition caused by pathogenic bacteria; and a method for reducing the severity of at least one symptom of an infection, disease or condition caused by pathogenic bacteria, in each case by administering to a subject an immunologically effective amount of an immunogenic composition comprising an oxo-eT linked glycoconjugate and a pharmaceutically acceptable excipient, carrier or diluent, wherein the glycoconjugate comprises a bacterial antigen, such as a bacterial capsular polysaccharide derived from the pathogenic bacteria.

In another aspect, the invention provides a method of inducing an immune response in a subject, comprising administering to the subject an immunologically effective amount of an immunogenic composition comprising an oxo-eT linked glycoconjugate and a pharmaceutically acceptable excipient, carrier or diluent, wherein the glycoconjugate comprises a bacterial antigen, such as a bacterial capsular polysaccharide. In preferred embodiments, the method involves producing a protective immune response in the subject, as further described herein.

In another aspect, the invention provides a method of administering an immunologically effective amount immunogenic composition comprising an oxo-eT linked glycoconjugate to a subject to generate a protective immune response in the subject, as further described herein.

In a further aspect, the invention provides an antibody generated in response an oxo-eT linked glycoconjugate of the present invention, or an immunogenic composition comprising such a glycoconjugate. Such antibodies can be used in research and clinical laboratory assays, such as bacterial detection and serotyping, or may be used to confer passive immunity to a subject.

In yet another aspect, the invention provides an immunogenic composition comprising an oxo-eT linked glycoconjugate of the present invention, for use in the prevention, treatment or amelioration of bacterial infection, for example infection by *S. pneumonia* or *N. meningitidis* or Group B *Streptococcus* or *S. aureus* or *Enterococcus* bacteria (such as *Enterococcus faecalis* or a *Enterococcus faecium*).

In another aspect, the invention provides the use of an immunogenic composition comprising an oxo-eT linked glycoconjugate of the present invention, for the preparation of a medicament for the prevention, treatment or amelioration of bacterial infection, for example infection by *S. pneumonia* or *N. meningitidis* or Group B *Streptococcus* or *S. aureus* or *Enterococcus* bacteria (such as *Enterococcus faecalis* or a *Enterococcus faecium*).

In certain preferred embodiments of the therapeutic and/or prophylactic methods and uses described above, the immunogenic composition comprises an oxo-eT linked glycoconjugate comprising a bacterial capsular polysaccharide covalently linked to a carrier protein through an oxo-eT spacer. In frequent embodiments of the methods and uses described herein, the bacterial capsular polysaccharide is a Pn capsular polysaccharide or a Mn capsular polysaccharide or a GBS capsular polysaccharide or a *S. aureus* polysaccharide or an or *Enterococcus* bacteria polysaccharide (such as *Enterococcus faecalis* or *Enterococcus faecium*). In some such embodiments, the Pn capsular polysaccharide is selected from the group consisting of Pn-serotype 1, 3, 4, 5, 6A, 6B, 7F, 8, 9V, 10A, 11A, 12F, 14, 15B, 18C, 19A, 19F, 22F, 23F and 33F capsular polysaccharides. In specific embodiments, the Pn capsular polysaccharide is selected from the group consisting of Pn-serotype 1, 2, 3, 4, 5, 6A, 6B, 7F, 8, 9V, 9N, 10A, 11A, 12F, 14, 15A, 15B, 17F, 18C, 19A, 19F, 20, 22F, 23A, 23B, 23F, 33F and 35B capsular polysaccharides. In specific embodiments, the Pn capsular polysaccharide is selected from the group consisting of Pn-serotype 1, 3, 4, 5, 6A, 6B, 7F, 8, 9V, 10A, 11A, 12F, 14, 15B, 18C, 19A, 19F, 22F, 23F and 33F capsular polysaccharides. In specific embodiments, the Pn capsular polysaccharide is selected from the group consisting of Pn-serotype 2, 9N, 15A, 17F, 20, 23A, 23B and 35B capsular polysaccharides. In other such embodiments, the Mn capsular polysaccharide is selected from the group consisting of Mn-serotype A, C, W135 and Y capsular polysaccharides. In other such embodiments, the GBS capsular polysaccharide is selected from the group consisting of serotype Ia, Ib, II, III or V capsular polysaccharides.

In certain embodiments of the therapeutic and/or prophylactic methods and uses described above, the immunogenic composition comprises an oxo-eT linked glycoconjugate comprising a bacterial capsular polysaccharide covalently linked to a carrier protein through an oxo-eT spacer. In certain embodiments of the methods and uses described herein, the bacterial capsular polysaccharide is a *S. aureus* capsular polysaccharide. In other such embodiments, the *S. aureus* capsular polysaccharide is *S. aureus* serotype 5 or 8 capsular polysaccharide.

In certain embodiments of the therapeutic and/or prophylactic methods and uses described above, the immunogenic composition comprises an oxo-eT linked glycoconjugate comprising a bacterial capsular polysaccharide covalently linked to a carrier protein through an oxo-eT spacer. In certain embodiments of the methods and uses described herein, the bacterial capsular polysaccharide is an *Enterococcus* bacteria capsular polysaccharide. In other such embodiments, the *Enterococcus* bacteria capsular polysaccharide is *Enterococcus faecalis* or *Enterococcus faecium* capsular polysaccharide.

In certain preferred embodiments, the carrier protein is $CRM_{197}$. In particularly preferred embodiments, the immunogenic composition comprises an oxo-eT linked glycoconjugate which comprises a bacterial capsular polysaccharide, such as a Pn or Mn or GBS or *S. aureus* or an *Enterococcus* bacteria polysaccharide (such as *Enterococcus faecalis* or *Enterococcus faecium*) capsular polysaccharide, covalently conjugated to $CRM_{197}$ through an oxo-eT spacer.

DETAILED DESCRIPTION

Figure 1:
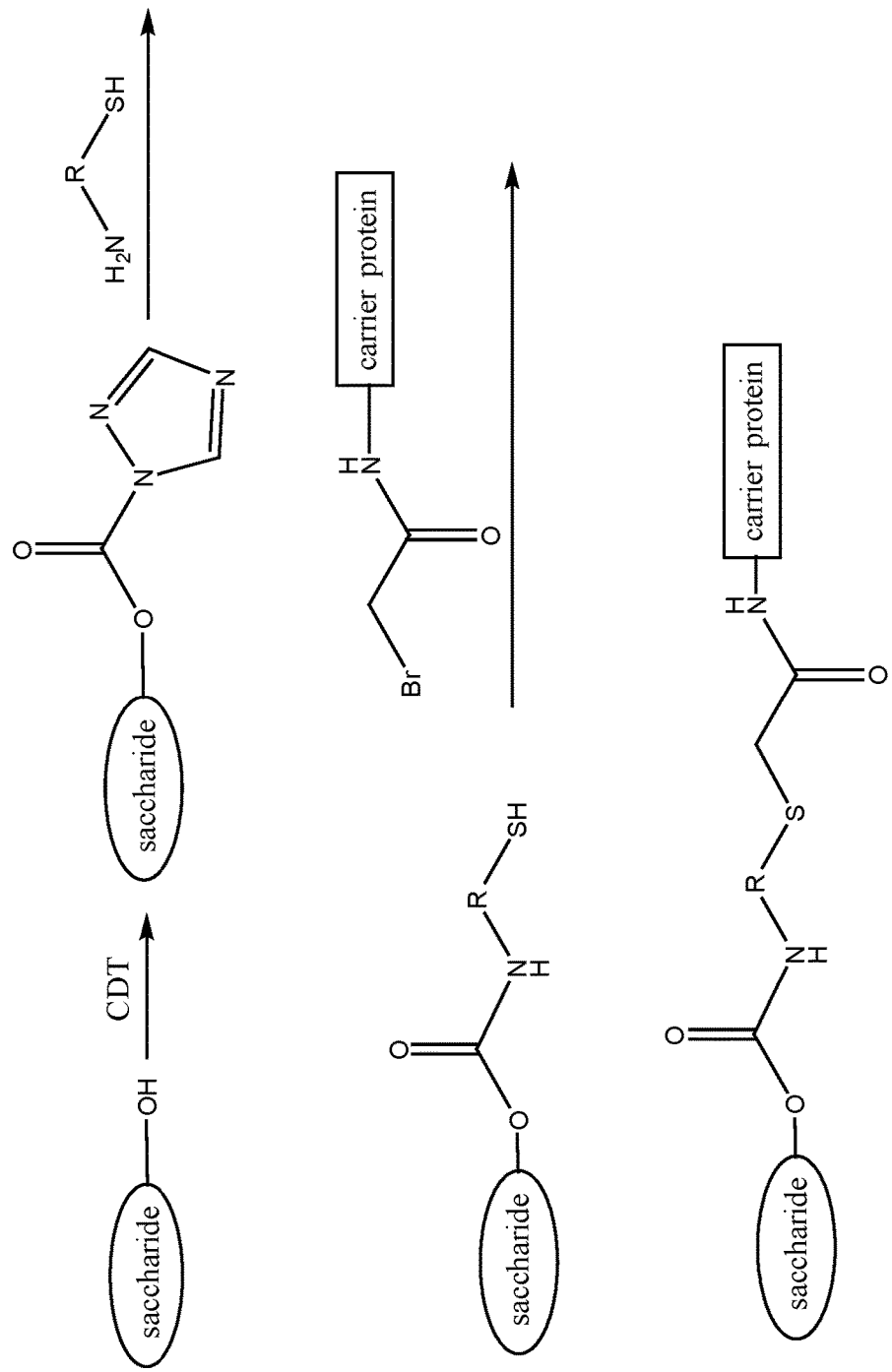
FIG. 1 shows a general scheme for the preparation of oxo-eTAC linked glycoconjugates of the invention, for a glycoconjugate comprising a polysaccharide covalently conjugated to $CRM_{197}$.

The present invention may be understood more readily by reference to the following detailed description of the preferred embodiments of the invention and the Examples included herein. Unless defined otherwise, all technical and scientific terms used herein have the same meaning as commonly understood by one of ordinary skill in the art to which the invention pertains. Although any methods and materials similar or equivalent to those described herein can be used in the practice or testing of the present invention, certain preferred methods and materials are described herein. In describing the embodiments and claiming the invention, certain terminology will be used in accordance with the definitions set out below.

As used herein, the singular forms "a", "an", and "the" include plural references unless indicated otherwise. Thus, for example, references to "the method" includes one or more methods, and/or steps of the type described herein, and references to "an oxo-eT spacer" refer to one or more eT spacers, as will be apparent to one of ordinary skill in the art upon reading the disclosure.

As used herein, the term "about" means within a statistically meaningful range of a value, such as a stated concentration range, time frame, molecular weight, temperature or pH. Such a range can be within an order of magnitude, typically within 20%, more typically within 10%, and even more typically within 5% of the indicated value or range. Sometimes, such a range can be within the experimental error typical of standard methods used for the measurement and/or determination of a given value or range. The allowable variation encompassed by the term "about" will depend upon the particular system under study, and can be readily appreciated by one of ordinary skill in the art. Whenever a range is recited within this application, every whole number integer within the range is also contemplated as an embodiment of the invention.

It is noted that in this disclosure, terms such as "comprises," "comprised," "comprising," "contains," "containing" and the like can have the meaning attributed to them in U.S. patent law; e.g., they can mean "includes," "included," "including" and the like. Such terms refer to the inclusion of a particular ingredients or set of ingredients without excluding any other ingredients. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from the novel or basic characteristics of the invention. The terms "consists of" and "consisting of" have the meaning ascribed to them in U.S. patent law; namely, that these terms are closed ended. Accordingly, these terms refer to the inclusion of a particular ingredient or set of ingredients and the exclusion of all other ingredients.

The term "saccharide" as used herein may refer to a polysaccharide, an oligosaccharide, or a monosaccharide. Frequently, references to a saccharide refer to a bacterial capsular polysaccharide, in particular capsular polysaccharides derived from pathogenic bacteria such as *S. pneumoniae* or *N. meningitis* or GBS or *S. aureus* or an *Enterococcus* bacteria (such as *Enterococcus faecalis* or *Enterococcus faecium*).

The terms "conjugate" or "glycoconjugate" are used interchangeably herein to refer to a saccharide covalently conjugated to a carrier protein. The glycoconjugates of the present invention are sometimes referred to herein as "oxo-eT linked" glycoconjugates, which comprise a saccharide covalently conjugated to a carrier protein through at least one oxo-eT spacer. The oxo-eT linked glycoconjugates of the invention and immunogenic compositions comprising them may contain some amount of free saccharide.

The term "free saccharide" as used herein means a saccharide that is not covalently conjugated to the carrier protein or a saccharide that is covalently attached to very few carrier proteins attached in a high saccharide/protein ratio (>5:1), but is nevertheless present in the glycoconjugate composition. The free saccharide may be non-covalently associated with (i.e., non-covalently bound to, adsorbed to, or entrapped in or with) the conjugated saccharide-carrier protein glycoconjugate. The terms "free polysaccharide" and "free capsular polysaccharide" may be used herein to convey the same meaning with respect to glycoconjugates wherein the saccharide is a polysaccharide or a capsular polysaccharide, respectively.

As used herein, "to conjugate," "conjugated" and "conjugating" refer to a process whereby a saccharide, for example a bacterial capsular polysaccharide, is covalently attached to a carrier molecule or carrier protein. In the methods of the present invention, the saccharide is covalently conjugated to the carrier protein through at least one oxo-eT spacer. The conjugation can be performed according to the methods described below or by other processes known in the art. Conjugation to a carrier protein enhances the immunogenicity of a bacterial capsular polysaccharide.

Glycoconjugates

The present invention relates to glycoconjugates comprising a saccharide covalently conjugated to a carrier protein through one or more oxo-eT spacers, wherein the saccharide is covalently conjugated to the oxo-eT spacer through a carbamate or an amine or an amide linkage, and wherein the carrier protein is covalently conjugated to the oxo-eT spacer through a thioether and an amide linkage.

In addition to the presence of one or more oxo-eT spacers, novel features of the glycoconjugates of the present invention include the molecular weight profiles of the saccharides and resulting oxo-eT linked glycoconjugates, the ratio of conjugated lysines per carrier protein and the number of lysines covalently linked to the polysaccharide through the oxo-eT spacer(s), the number of covalent linkages between the carrier protein and the saccharide as a function of repeat units of the saccharide, and the relative amount of free saccharide compared to the total amount of saccharide.

The oxo-eT linked glycoconjugates of the invention may be represented by the general formula (I), as illustrated below:

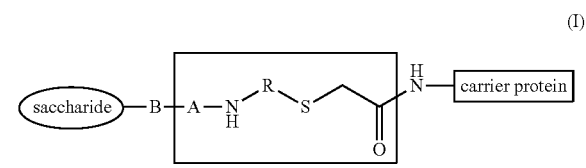

wherein:
A is a group $(C=X)_m$ wherein X is S or O and m is 0 or 1;
B is a bond, O, or $CH_2$; and when m is 0, B can also be $(C=O)$;
R is a $C_2$-$C_{16}$ alkylene, $C_2$-$C_{16}$ heteroalkylene, NH—C(=O)—$C_2$-$C_{16}$ alkylene, or NH—C(=O)—$C_2$-$C_{16}$ heteroalkylene, wherein said alkylene and heteroalkylene are optionally substituted by 1, 2 or 3 groups independently selected from COOR' where R' is selected from H, methyl, ethyl or propyl.

In the here above general formula (I), $C_2$-$C_{10}$ alkylene denotes a straight-chain or branched group containing 2 to 10 carbon atoms. Examples of suitable ($C_2$-$C_{10}$) alkylene radicals are $(CH_2)_2$, $(CH_2)_3$, $CH_2$—(CH—$CH_3$)—$CH_2$, $(CH_2)_5$, $(CH_2)_6$, $(CH_2)_7$, $(CH_2)_8$, $(CH_2)_9$, $(CH_2)_{10}$, $(CH_2)_2$—(CH—$CH_3$)—$(CH_2)_2$.

In the here above general formula (I), heteroalkylene refers to an alkylene group as defined herein in which one or more of the carbon atoms is each independently replaced with the same or different heteroatom selected from O, S or N. In a preferred embodiment, heteroalkylene refers to an alkylene group as defined herein in which one or more of the carbon atoms is each replaced with an oxygen atom. Example of suitable $C_2$-$C_{20}$ heteroalkylene are O—$CH_2$, O—$CH_2$—$CH_2$, $CH_2$—$CH_2$—O—$CH_2$—$CH_2$, O—$CH_2$—$CH_2$—O—$CH_2$—$CH_2$, O—$CH_2$—$CH_2$—O—$CH_2$—$CH_2$, $CH_2$—O—$CH_2$—$CH_2$, O—$CH_2$—$CH_2$—(N—$CH_3$)—$CH_2$—$CH_2$—O—$CH_2$—$CH_2$, $CH_2$—$CH_2$—(N—$CH_3$)—$CH_2$—$CH_2$, $CH_2$—$CH_2$—S—$CH_2$—$CH_2$ . . . .

In an embodiment, the oxo-eT linked glycoconjugates of the invention may be represented by the general formula (I) above and wherein:
R=(CH$_2$)$_n$ wherein n=1 to 10 or
R=(CH$_2$CH$_2$O)$_n$CH$_2$CH$_2$ wherein n=1 to 5 or
R=(CH(COOH)(CH$_2$)$_n$ wherein n=1 to 10 or
R=NHCO(CH$_2$)$_n$ wherein n=1 to 10 or
R=NHCO(CH$_2$CH$_2$O)$_n$CH$_2$ CH wherein n=1 to 4 or
R=O(CH$_2$)$_n$ wherein n=1 to 10 or
R=O(CH$_2$CH$_2$O)$_n$CH$_2$CH wherein n=1 to 4.

The oxo-eTAC spacer provides stable carbamate, thioether and amide bonds between the saccharide and carrier protein. Synthesis of the oxo-eTAC linked glycoconjugate involves reaction of an activated hydroxyl group of the saccharide with the amino group of a thioalkylamine reagent, forming a carbamate linkage to the saccharide to provide a thiolated saccharide. Generation of one or more free sulfhydryl groups is accomplished by reaction with a reducing agent to provide an activated thiolated saccharide (if thiol is protected). Reaction of the free sulfhydryl groups of the activated thiolated saccharide with an activated carrier protein having one or more α-haloacetamide groups on amine containing residues generates a thioether bond to form the conjugate, wherein the carrier protein is attached to the oxo-eTAC spacer through a thioether and an amide bond.

The oxo-eTAAN spacer, one of eT spacer's subgroup provides stable amine, thioether and amide bonds between the saccharide and carrier protein. The saccharide is first activated by oxidation of vicinal diol groups with periodate or oxidation of primary hydroxyl groups with a combination of TEMPO and an oxidant to produce aldehyde groups. Oxidation of primary hydroxyl groups is preferred over periodate oxidsation since it does not involve chain scission thereby leading to minimal epitope modification. Synthesis of the oxo-eTAAN linked glycoconjugate involves reaction of an activated saccharide aldehyde with the amino group of a bifunctional linker containing amine and thiol functionalities, forming an amine linkage to the saccharide to provide a thiolated saccharide. Generation of one or more free sulfhydryl groups is accomplished by reaction with a reducing agent to provide an activated thiolated saccharide (if thiol is protected). Reaction of the free sulfhydryl groups of the activated thiolated saccharide with an activated carrier protein having one or more α-haloacetamide groups on amine containing residues generates a thioether bond to form the conjugate, wherein the carrier protein is attached to the oxo-eTAAN spacer through a thioether and an amide bond.

The oxo-eTAAD spacer, one of oxo-eT spacer's subgroup provides stable thioether and amide bonds between the saccharide and carrier protein. Synthesis of the oxo-eTAAD linked glycoconjugate involves reaction of an activated carboxyl group of the saccharide with the amino group of a bifunctional linker containing amine and thiol functionalities, forming an amide linkage to the saccharide to provide a thiolated saccharide. Generation of one or more free sulfhydryl groups is accomplished by reaction with a reducing agent to provide an activated thiolated saccharide (if thiol is protected). Reaction of the free sulfhydryl groups of the activated thiolated saccharide with an activated carrier protein having one or more α-haloacetamide groups on amine containing residues generates a thioether bond to form the conjugate, wherein the carrier protein is attached to the oxo-eTAAD spacer through a thioether and an amide bond.

In glycoconjugates of the invention, the saccharide may be a polysaccharide, an oligosaccharide, or a monosaccharide, and the carrier protein may be selected from any suitable carrier as further described herein or known to those of skill in the art. In frequent embodiments, the saccharide is a bacterial capsular polysaccharide. In some such embodiments, the carrier protein is CRM$_{197}$.

In some such embodiments, the oxo-eT linked glycoconjugate comprises a Pn capsular polysaccharide derived from *S. pneumoniae*. In specific embodiments, the Pn capsular polysaccharide is selected from the group consisting of Pn-serotype 1, 3, 4, 5, 6A, 6B, 7F, 8, 9V, 10A, 11A, 12F, 14, 15B, 18C, 19A, 19F, 22F, 23F and 33F capsular polysaccharides. In other embodiments, the Pn capsular polysaccharide is selected from the group consisting of Pn-serotype 1, 2, 3, 4, 5, 6A, 6B, 7F, 8, 9V, 9N, 10A, 11A, 12F, 14, 15A, 15B, 17F, 18C, 19A, 19F, 20, 22F, 23A, 23B, 23F, 33F and 35B capsular polysaccharides. In other embodiments, the Pn capsular polysaccharide is selected from the group consisting of Pn-serotype 2, 9N, 15A, 17F, 20, 23A, 23B and 35B capsular polysaccharides. In other embodiments, the capsular polysaccharide is selected from the group consisting of Pn-Serotypes 10A, 11A, 22F and 33F capsular polysaccharides. In one such embodiment, the capsular polysaccharide is a Pn-33F capsular polysaccharide. In another such embodiment, the capsular polysaccharide is a Pn-22F capsular polysaccharide. In another such embodiment, the capsular polysaccharide is a Pn-10A capsular polysaccharide. In yet another such embodiment, the capsular polysaccharide is a Pn-11A capsular polysaccharide.

In other embodiments, the oxo-eT linked glycoconjugate comprises a Mn capsular polysaccharide derived from *N. meningitidis*. In specific embodiments, the Mn capsular polysaccharide is selected from the group consisting of Mn-serotype A, C, W135 and Y capsular polysaccharides. In one such embodiment, the capsular polysaccharide is a Mn-A capsular polysaccharide. In another such embodiment, the capsular polysaccharide is a Mn—C capsular polysaccharide. In another such embodiment, the capsular polysaccharide is a Mn—W135 capsular polysaccharide. In yet another such embodiment, the capsular polysaccharide is a Mn—Y capsular polysaccharide. In another specific embodiment, the Mn capsular polysaccharide is Mn-serotype X capsular polysaccharides.

In other embodiments, the oxo-eT linked glycoconjugate comprises a GBS capsular polysaccharide derived from Group B *Streptococcus*. In specific embodiments, the GBS capsular polysaccharide is selected from the group consisting of GBS-serotype Ia, Ib, II, III and V capsular polysaccharides. In one such embodiment, the capsular polysaccharide is a GBS-Ia capsular polysaccharide. In another such embodiment, the capsular polysaccharide is a GBS-Ib capsular polysaccharide. In another such embodiment, the capsular polysaccharide is a GBS-II capsular polysaccharide. In another such embodiment, the capsular polysaccharide is a GBS-III capsular polysaccharide. In yet another such embodiment, the capsular polysaccharide is a GBS-V capsular polysaccharide.

In other embodiments, the oxo-eT linked glycoconjugate comprises a capsular polysaccharide derived from *Staphylococcus aureus*. In specific embodiments, the *S. aureus* capsular polysaccharide is *S. aureus* serotype 5 or 8 capsular polysaccharide.

In other embodiments, the oxo-eT linked glycoconjugate comprises a capsular polysaccharide derived from an *Enterococcus* bacteria. In specific embodiments, the *Enterococcus* capsular polysaccharide is *Enterococcus faecalis* or *Enterococcus faecium* capsular polysaccharide.

In particularly preferred embodiments, the oxo-eT linked glycoconjugate comprises a Pn or Mn bacterial capsular polysaccharide, such as a Pn-serotype 1, 3, 4, 5, 6A, 6B, 7F, 8, 9V, 10A, 11A, 12F, 14, 15B, 18C, 19A, 19F, 22F, 23F or 33F capsular polysaccharide, or a Mn-serotype A, C, W135 or Y capsular polysaccharide, or a GBS-serotype Ia, Ib, II, III or V capsular polysaccharide, which is covalently conjugated to $CRM_{197}$ through an oxo-eT spacer.

In other embodiments, the oxo-eT linked glycoconjugate comprises a *S. aureus* or *Enterococcus* bacterial capsular polysaccharide, such as *S. aureus* serotype 5 or 8 capsular polysaccharide, or *Enterococcus faecalis* or *Enterococcus faecium* capsular polysaccharide, which is covalently conjugated to $CRM_{197}$ through an oxo-eT spacer.

In some embodiments, the oxo-eT linked glycoconjugates of the present invention comprise a saccharide covalently conjugated to the carrier protein through an oxo-eT spacer, wherein the saccharide has a molecular weight of between 10 kDa and 2,000 kDa. In other such embodiments, the saccharide has a molecular weight of between 50 kDa and 2,000 kDa. In further such embodiments, the saccharide has a molecular weight of between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa. In some such embodiments, the saccharide is a bacterial capsular polysaccharide, such as a Pn-serotype 1, 3, 4, 5, 6A, 6B, 7F, 8, 9V, 10A, 11A, 12F, 14, 15B, 18C, 19A, 19F, 22F, 23F or 33F capsular polysaccharide, or a Mn-serotype A, C, W135 or Y capsular polysaccharide, or a GBS-serotype Ia, Ib, II, III or V capsular polysaccharide wherein the capsular polysaccharide has a molecular weight falling within any of the molecular weight ranges as described. In some other embodiments, the saccharide is a bacterial capsular polysaccharide, such as a capsular polysaccharide from *Staphylococcus aureus* (e.g. *S. aureus* serotype 5 or 8 capsular polysaccharide) or capsular polysaccharide from an *Enterococcus* bacteria (such as *Enterococcus faecalis* or *Enterococcus faecium* capsular polysaccharide) wherein the capsular polysaccharide has a molecular weight falling within any of the molecular weight ranges as described.

In some embodiments, the oxo-eT linked glycoconjugate of the invention has a molecular weight of between 50 kDa and 20,000 kDa. In other embodiments, the oxo-eT linked glycoconjugate has a molecular weight of between 500 kDa and 10,000 kDa. In other embodiments, the oxo-eT linked glycoconjugate has a molecular weight of between 200 kDa and 10,000 kDa. In still other embodiments, the oxo-eT linked glycoconjugate has a molecular weight of between 1,000 kDa and 3,000 kDa.

In further embodiments, the oxo-eT linked glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

Another way to characterize the oxo-eT linked glycoconjugates of the invention is by the number of lysine residues in the carrier protein that become conjugated to the saccharide through an oxo-eT spacer, which can be characterized as a range of conjugated lysines.

In frequent embodiments, the carrier protein is covalently conjugated to the oxo-eT spacer through an amide linkage to one or more ε-amino groups of lysine residues on the carrier protein. In some such embodiments, the carrier protein comprises 2 to 20 lysine residues covalently conjugated to the saccharide. In other such embodiments, the carrier protein comprises 4 to 16 lysine residues covalently conjugated to the saccharide.

In a preferred embodiment, the carrier protein comprises $CRM_{197}$, which contains 39 lysine residues. In some such embodiments, the $CRM_{197}$ may comprise 4 to 16 lysine residues out of 39 covalently linked to the saccharide. Another way to express this parameter is that about 10% to about 41% of $CRM_{197}$ lysines are covalently linked to the saccharide. In another such embodiment, the $CRM_{197}$ may comprise 2 to 20 lysine residues out of 39 covalently linked to the saccharide. Another way to express this parameter is that about 5% to about 50% of $CRM_{197}$ lysines are covalently linked to the saccharide.

The oxo-eT linked glycoconjugates of the invention may also be characterized by the ratio (weight/weight) of saccharide to carrier protein. In some embodiments, the saccharide: carrier protein ratio (w/w) is between 0.2 and 4. In other embodiments, the saccharide: carrier protein ratio (w/w) is between 1.0 and 2.5. In further embodiments, the saccharide: carrier protein ratio (w/w) is between 0.4 and 1.7. In some such embodiments, saccharide is a bacterial capsular polysaccharide, and/or the carrier protein is $CRM_{197}$.

Glycoconjugates may also be characterized by the number of covalent linkages between the carrier protein and the saccharide as a function of repeat units of the saccharide. In one embodiment, the glycoconjugate of the invention comprises at least one covalent linkage between the carrier protein and the polysaccharide for every 4 saccharide repeat units of the polysaccharide. In another embodiment, the covalent linkage between the carrier protein and the polysaccharide occurs at least once in every 10 saccharide repeat units of the polysaccharide. In another embodiment, the covalent linkage between the carrier protein and the polysaccharide occurs at least once in every 15 saccharide repeat units of the polysaccharide. In a further embodiment, the covalent linkage between the carrier protein and the polysaccharide occurs at least once in every 25 saccharide repeat units of the polysaccharide.

In frequent embodiments, the carrier protein is $CRM_{197}$ and the covalent linkage via an oxo-eT spacer between the $CRM_{197}$ and the polysaccharide occurs at least once in every 4, 10, 15 or 25 saccharide repeat units of the polysaccharide.

An important consideration during conjugation is the development of conditions that permit the retention of potentially sensitive non-saccharide substituent functional groups of the individual components, such as O-Acyl, phosphate or glycerol phosphate side chains that may form part of the saccharide epitope.

In one embodiment, the glycoconjugate comprises a saccharide which has a degree of O-acetylation between 10-100%. In some such embodiments, the saccharide has a degree of O-acetylation between 50-100%. In other such embodiments, the saccharide has a degree of O-acetylation between 75-100%. In further embodiments, the saccharide has a degree of O-acetylation greater than or equal to 70% ($\geq 70\%$).

The oxo-eT linked glycoconjugates and immunogenic compositions of the invention may contain free saccharide that is not covalently conjugated to the carrier protein, but is nevertheless present in the glycoconjugate composition. The free saccharide may be non-covalently associated with (i.e., non-covalently bound to, adsorbed to, or entrapped in or with) the glycoconjugate.

In some embodiments, the oxo-eT linked glycoconjugate comprises less than about 45% free saccharide, less than about 40% free saccharide, less than about 35% free saccharide, less than about 30% free saccharide, less than about 25% free saccharide, less than about 20% free saccharide, less than about 15% free saccharide, less than about 10% free saccharide, or less than about 5% free saccharide relative to the total amount of saccharide. Preferably, the glycoconjugate comprises less than 15% free saccharide, more preferably less than 10% free saccharide, and still more preferably, less than 5% of free saccharide.

In certain preferred embodiments, the invention provides an oxo-eT linked glycoconjugate comprising a capsular polysaccharide, preferably a Pn or Mn capsular polysaccharide, covalently conjugated to a carrier protein through an oxo-eT spacer, having one or more of the following features alone or in combination: the polysaccharide has a molecular weight of between 50 kDa and 2,000 kDa; the glycoconjugate has a molecular weight of between 500 kDa to 10,000 KDa; the carrier protein comprises 2 to 20 lysine residues covalently linked to the saccharide; the saccharide:carrier protein ratio (w/w) is between 0.2 and 4; the glycoconjugate comprises at least one covalent linkage between the carrier protein and the polysaccharide for every 4, 10, 15 or 25 saccharide repeat units of the polysaccharide; the saccharide has a degree of 0-acetylation between 75-100%; the conjugate comprises less than about 15% free polysaccharide relative to total polysaccharide; the carrier protein is $CRM_{197}$; the capsular polysaccharide is selected from Pn-serotype 1, 3, 4, 5, 6A, 6B, 7F, 8, 9V, 10A, 11A, 12F, 14, 15B, 18C, 19A, 19F, 22F, 23F or 33F capsular polysaccharides, or the capsular polysaccharide is selected from Mn-serotype A, C, W135 or Y capsular polysaccharides.

In certain preferred embodiments, the invention provides an oxo-eT linked glycoconjugate comprising a capsular polysaccharide, preferably a Pn or Mn capsular polysaccharide, covalently conjugated to a carrier protein through an oxo-eT spacer, having one or more of the following features alone or in combination: the polysaccharide has a molecular weight of between 50 kDa and 2,000 kDa; the glycoconjugate has a molecular weight of between 500 kDa to 10,000 KDa; the carrier protein comprises 2 to 20 lysine residues covalently linked to the saccharide; the saccharide:carrier protein ratio (w/w) is between 0.2 and 4; the glycoconjugate comprises at least one covalent linkage between the carrier protein and the polysaccharide for every 4, 10, 15 or 25 saccharide repeat units of the polysaccharide; the saccharide has a degree of 0-acetylation between 75-100%; the conjugate comprises less than about 15% free polysaccharide relative to total polysaccharide; the carrier protein is $CRM_{197}$; the capsular polysaccharide is selected from GBS-serotype Ia, Ib, II, III or V capsular polysaccharide or *S. aureus* serotype 5 or 8 capsular polysaccharide or *Enterococcus faecalis* or *Enterococcus faecium* capsular polysaccharide.

The oxo-eT linked glycoconjugates may also be characterized by their molecular size distribution ($K_d$). The molecular size of the conjugates is determined by Sepharose CL-4B stationary phase size exclusion chromatography (SEC) media using high pressure liquid chromatography system (HPLC). For $K_d$ determination, the chromatography column is first calibrated to determine $V_0$, which represents the void volume or total exclusion volume, and $V_i$, the volume at which the smallest molecules in the sample elutes, which is also known as interparticle volume. All SEC separation takes place between $V_0$ and $V_i$. The $K_d$ value for each fraction collected is determined by the following expression $K_d=(V_e-V_i)/(V_i-V_0)$, where $V_e$ represents the retention volume of the compound. The % fraction (major peak) that elutes $\leq 0.3$ defines the conjugate $K_d$ (molecular size distribution). In some embodiments, the invention provides oxo-eT linked glycoconjugates having a molecular size distribution ($K_d$) of $\geq 35\%$. In other embodiments, the invention provides oxo-eT linked glycoconjugates having a molecular size distribution ($K_d$) of $\geq 15\%$, $\geq 20\%$, $\geq 25\%$, $\geq 30\%$, $\geq 35\%$, $\geq 40\%$, $\geq 45\%$, $\geq 50\%$, $\geq 60\%$, $\geq 70\%$, $\geq 80\%$, or $\geq 90\%$.

The oxo-eT linked glycoconjugates and immunogenic compositions of the invention may contain free sulfhydryl residues. In some instances, the activated thiolated saccharides formed by the methods provided herein will contain multiple free sulfhydryl residues, some of which may not undergo covalent conjugation to the carrier protein during the conjugation step. Such residual free sulfhydryl residues are capped by reaction with a thiol-reactive capping reagent, for example iodoacetamide (IAA), to cap the potentially reactive functionality. Other thiol-reactive capping reagents, e.g., maleimide containing reagents and the like, are also contemplated.

In addition, the oxo-eT linked glycoconjugates and immunogenic compositions of the invention may contain residual unconjugated carrier protein, which may include activated carrier protein which has undergone modification during the capping process steps.

The glycoconjugates of the invention can be used in the production of immunogenic compositions to protect recipients from bacterial infections, for example by pathogenic bacteria such as *S. pneumonia* or *N. meningitidis* or Group B *Streptococcus* or *S. aureus* or *Enterococcus* bacteria (such as *Enterococcus faecalis* or a *Enterococcus faecium*. Thus, in another aspect, the invention provides an immunogenic composition comprising an oxo-eT linked glycoconjugate and a pharmaceutically acceptable excipient, carrier or diluent, wherein the glycoconjugate comprises a saccharide covalently conjugated to a carrier protein through an oxo-eT spacer, as described herein.

In frequent embodiments, the immunogenic composition comprises an oxo-eT linked glycoconjugate and a pharmaceutically acceptable excipient, carrier or diluent, wherein the glycoconjugate comprises a bacterial capsular polysaccharide.

In some such embodiments, the immunogenic composition comprises an oxo-eT linked glycoconjugate which comprises a Pn capsular polysaccharide derived from *S. pneumoniae*. In some specific embodiments, the Pn capsular polysaccharide is selected from the group consisting of Pn-serotype 1, 3, 4, 5, 6A, 6B, 7F, 8, 9V, 10A, 11A, 12F, 14, 15B, 18C, 19A, 19F, 22F, 23F and 33F capsular polysaccharides.

In other such embodiments, the immunogenic composition comprises an oxo-eT linked glycoconjugate which comprises a Mn capsular polysaccharide derived from *N. meningitidis*. In some specific embodiments, the Mn capsular polysaccharide is selected from the group consisting of Mn-serotype A, C, W135 and Y capsular polysaccharides.

In other such embodiments, the immunogenic composition comprises an oxo-eT linked glycoconjugate which comprises a GBS capsular polysaccharide derived from Group B *Streptococcus*. In some specific embodiments, the GBS capsular polysaccharide is selected from the group consisting of GBS-serotype Ia, Ib, II, III or V capsular polysaccharide. In other such embodiments, the immunogenic composition comprises an oxo-eT linked glycoconjugate which comprises a *S. aureus* capsular polysaccharide. In some specific embodiments, the *S. aureus* capsular polysaccharide is *S. aureus* serotype 5 or 8 capsular polysaccharide.

In other such embodiments, the immunogenic composition comprises an oxo-eT linked glycoconjugate which comprises an *Enterococcus* bacteria capsular polysaccharide. In some specific embodiments, the *Enterococcus* bacteria capsular polysaccharide is *Enterococcus faecalis* or *Enterococcus faecium* capsular polysaccharide.

In particularly preferred embodiments, the immunogenic composition comprises an oxo-eT linked glycoconjugate which comprises a bacterial capsular polysaccharide, such as a Pn or Mn or GBS capsular polysaccharide, covalently conjugated to $CRM_{197}$ through an oxo-eT spacer.

In some embodiments, the immunogenic composition comprises an adjuvant. In some such embodiments, the adjuvant is an aluminum-based adjuvant selected from the group consisting of aluminum phosphate, aluminum sulfate and aluminum hydroxide. In one embodiment, the immunogenic composition comprises the adjuvant aluminum phosphate.

The oxo-eT linked glycoconjugates of the invention and immunogenic compositions comprising them may contain some amount of free saccharide. In some embodiments, the immunogenic composition comprises less than about 45%, less than about 40%, less than about 35%, less than about 30%, less than about 25%, less than about 20%, less than about 15%, less than about 10%, or less than about 5% free polysaccharide compared to the total amount of polysaccharide. Preferably, the immunogenic composition comprises less than 15% free saccharide, more preferably less than 10% free saccharide, and still more preferable, less than 5% of free saccharide.

In another aspect, the glycoconjugates or immunogenic compositions of the invention can be used to generate antibodies that are functional as measured by killing bacteria in an animal efficacy model or via an opsonophagocytic killing assay. Glycoconjugates of the invention comprising a bacterial capsular polysaccharide can be used in the production of antibodies against such a bacterial capsular polysaccharide. Such antibodies subsequently can be used in research and clinical laboratory assays, such as bacterial detectiontion and serotyping. Such antibodies may also be used to confer passive immunity to a subject. In some embodiments, the antibodies produced against bacterial polysaccharides are functional in either an animal efficacy model or in an opsonophagocytic killing assay.

The oxo-eT linked glycoconjugates and immunogenic compositions described herein may also be used in various therapeutic or prophylactic methods for preventing, treating or ameliorating a bacterial infection, disease or condition in a subject. In particular, oxo-eT linked glycoconjugates comprising a bacterial antigen, such as a bacterial capsular polysaccharide from a pathogenic bacteria, may be used to prevent, treat or ameliorate a bacterial infection, disease or condition in a subject caused by pathogenic bacteria.

Thus in one aspect, the invention provides a method of preventing, treating or ameliorating a bacterial infection, disease or condition in a subject, comprising administering to the subject an immunologically effective amount of an immunogenic composition of the invention, wherein said immunogenic composition comprises an oxo-eT linked glycoconjugate comprising a bacterial capsular polysaccharide.

In one embodiment, the infection, disease or condition is associated with *S. pneumonia* bacteria and the glycoconjugate comprises a Pn capsular polysaccharide. In some such embodiments, the infection, disease or condition is selected from the group consisting of pneumonia, sinusitis, otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess.

In another embodiment, the infection, disease or condition is associated with *N. meningitidis* bacteria and the glycoconjugate comprises a Mn capsular polysaccharide. In some such embodiments, the infection, disease or condition is selected from the group consisting of meningitis, meningococcemia, bacteremia and sepsis.

In another embodiment, the infection, disease or condition is associated with Group B *Streptococcus* bacteria and the glycoconjugate comprises a GBS capsular polysaccharide.

In another aspect, the invention provides a method of inducing an immune response in a subject, comprising administering to the subject an immunologically effective amount of an immunogenic composition comprising an oxo-eT linked glycoconjugate and a pharmaceutically acceptable excipient, carrier or diluent, wherein the glycoconjugate comprises a bacterial capsular polysaccharide.

In yet another aspect, the invention provides a method for preventing, treating or ameliorating a disease or condition caused by pathogenic bacteria in a subject, comprising administering to the subject an immunologically effective amount of an immunogenic composition comprising an oxo-eT linked glycoconjugate and a pharmaceutically acceptable excipient, carrier or diluent, wherein the glycoconjugate comprises a bacterial capsular polysaccharide.

In another aspect, the invention provides a method for reducing the severity of at least one symptom of a disease or condition caused by infection with pathogenic bacteria, comprising administering to a subject an immunologically effective amount of an immunogenic composition comprising an oxo-eT linked glycoconjugate and a pharmaceutically acceptable excipient, carrier or diluent, wherein the glycoconjugate comprises a bacterial capsular polysaccharide, e.g., a Pn or Mn or GBS or *S. aureus* or *Enterococcus* capsular polysaccharide.

In another aspect, the invention provides a method of administering an immunologically effective amount of an immunogenic composition comprising an oxo-eT linked glycoconjugate of the invention to a subject to generate a protective immune response in the subject, as further described herein.

In yet another aspect, the invention provides an immunogenic composition comprising an oxo-eT linked glycoconjugate of the present invention, as described herein, for use in the prevention, treatment or amelioration of a bacterial infection, for example an infection by *S. pneumonia* or *N. meningitidis* or Group B *streptococcus* or *S. aureus* or *Enterococcus* bacteria (such as *Enterococcus faecalis* or *Enterococcus faecium*)

In another aspect, the invention provides the use of an immunogenic composition comprising an oxo-eT linked glycoconjugate of the present invention, as described herein, for the preparation of a medicament for the prevention, treatment or amelioration of a bacterial infection, for example infection by *S. pneumonia* or *N. meningitidis* or Group B *Streptococcus* or *S. aureus* or *Enterococcus* bacteria (such as *Enterococcus faecalis* or *Enterococcus faecium*).

In the therapeutic and/or prophylactic methods and uses described above, the immunogenic composition frequently comprises an oxo-eT linked glycoconjugate comprising a bacterial capsular polysaccharide covalently linked to a carrier protein through an oxo-eT spacer. In frequent embodiments of the methods and described herein, the bacterial capsular polysaccharide is a Pn capsular polysaccharide or a Mn capsular polysaccharide or a GBS capsular polysaccharide or *S. aureus* capsular polysaccharide or an *Enterococcus* bacteria capsular polysaccharide (such as *Enterococcus faecalis* or *Enterococcus faecium*). In some such embodiments, the capsular polysaccharide is selected from the group consisting of Pn-serotype 1, 3, 4, 5, 6A, 6B, 7F, 8, 9V, 10A, 11A, 12F, 14, 15B, 18C, 19A, 19F, 22F, 23F and 33F capsular polysaccharides. In other such embodiments, the capsular polysaccharide is selected from the group consisting of Mn-serotype A, C, W135 and Y capsular polysaccharides. In other such embodiments, the capsular polysaccharide is selected from the group consisting of GBS-serotype Ia, Ib, II, III and V capsular polysaccharides.

In other such embodiments, the capsular polysaccharide is selected, the capsular polysaccharide is a *S. aureus* capsular polysaccharide. In other such embodiments, the *S. aureus* capsular polysaccharide is *S. aureus* serotype 5 or 8 capsular polysaccharide.

In other such embodiments, the capsular polysaccharide is an *Enterococcus* bacteria capsular polysaccharide. In other such embodiments, the *Enterococcus* bacteria capsular polysaccharide is *Enterococcus faecalis* or *Enterococcus faecium* capsular polysaccharide.

In certain preferred embodiments, the carrier protein is $CRM_{197}$. In particularly preferred embodiments, the immunogenic composition comprises an oxo-eT linked glycoconjugate which comprises a bacterial capsular polysaccharide, such as a Pn or Mn or GBS or *S. aureus* or *Enterococcus* bacteria capsular polysaccharide, covalently conjugated to $CRM_{197}$ through an oxo-eT spacer.

In addition, the present invention provides methods for inducing an immune response against *S. pneumoniae* or *N. meningitidis* or Group B *Streptococcus* or *S. aureus* or *Enterococcus* (such as *Enterococcus faecalis* or a *Enterococcus faecium*) bacteria in a subject, methods for preventing, treating or ameliorating an infection, disease or condition caused by *S. pneumoniae* or *N. meningitidis* bacteria or Group B *Streptococcus* or *S. aureus* or *Enterococcus* bacteria (such as *Enterococcus faecalis* or a *Enterococcus faecium*) in a subject, and methods for reducing the severity of at least one symptom of an infection, disease or condition caused by infection with *S. pneumoniae* or *N. meningitidis* or Group B *Streptococcus* or *S. aureus* or *Enterococcus* bacteria (such as *Enterococcus faecalis* or a *Enterococcus faecium*) in a subject, in each case by administering to the subject an immunologically effective amount of an immunogenic composition comprising an oxo-eT linked glycoconjugate and a pharmaceutically acceptable excipient, carrier or diluent, wherein the glycoconjugate comprises a bacterial capsular polysaccharide derived from *S. pneumoniae* or *N. meningitidis* or Group B *Streptococcus* or *S. aureus* or *Enterococcus* bacteria (such as *Enterococcus faecalis* or a *Enterococcus faecium*), respectively.

Saccharides

Saccharides may include polysaccharides, oligosaccharides and monosaccharides. In frequent embodiments, the saccharide is a polysaccharide, in particular a bacterial capsular polysaccharide. Capsular polysaccharides are prepared by standard techniques known to those of ordinary skill in the art.

In the present invention, capsular polysaccharides may be prepared, e.g., from Pn-serotypes 1, 3, 4, 5, 6A, 6B, 7F, 8, 9V, 10A, 11A, 12F, 14, 15B, 18C, 19A, 19F, 22F, 23F and 33F of *S. pneumoniae*. In one embodiment, each pneumococcal polysaccharide serotype may be grown in a soy-based medium. Individual polysaccharides are purified through centrifugation, precipitation, ultra-filtration, and/or column chromatography. Purified polysaccharides may be activated to make them capable of reacting with the oxo-eT spacer and then incorporated into glycoconjugates of the invention, as further described herein.

The molecular weight of the capsular polysaccharide is a consideration for use in immunogenic compositions. High molecular weight capsular polysaccharides are able to induce certain antibody immune responses due to a higher valence of the epitopes present on the antigenic surface. The isolation and purification of high molecular weight capsular polysaccharides is contemplated for use in the conjugates, compositions and methods of the present invention.

In some embodiments, the saccharide has a molecular weight of between 10 kDa and 2,000 kDa. In other such embodiments, the saccharide has a molecular weight of between 50 kDa and 2,000 kDa. In further such embodiments, the saccharide has a molecular weight of between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa. In some such embodiments, the saccharide is a bacterial capsular polysaccharide, such as a Pn-serotype 1, 3, 4, 5, 6A, 6B, 7F, 8, 9V, 10A, 11A, 12F, 14, 15B, 18C, 19A, 19F, 22F, 23F or 33F capsular polysaccharide, or a Mn-serotype A, C, W135 or Y capsular polysaccharide, or GBS-serotype Ia, Ib, II, III and V capsular polysaccharides, or a *S. aureus* capsular polysaccharide or an or *Enterococcus* bacteria capsular polysaccharide (such as *Enterococcus faecalis* or *Enterococcus faecium*) wherein the capsular polysaccharide has a molecular weight falling within one of the molecular weight ranges as described.

In some embodiments, the saccharides of the invention are O-acetylated. In some embodiments, the glycoconjugate comprises a saccharide which has a degree of O-acetylation of between 10-100%, between 20-100%, between 30-100%, between 40-100%, between 50-100%, between 60-100%, between 70-100%, between 75-100%, 80-100%, 90-100%, 50-90%, 60-90%, 70-90% or 80-90%. In other embodiments, the degree of O-acetylation is ≥10%, ≥20%, ≥30%, ≥40%, ≥50%, ≥60%, ≥70%, ≥80%, or ≥90%, or about 100%.

In some embodiments, the capsular polysaccharides, glycoconjugates or immunogenic compositions of the invention are used to generate antibodies that are functional as measured by the killing of bacteria in an animal efficacy model or an opsonophagocytic killing assay that demonstrates that the antibodies kill the bacteria.

Capsular polysaccharides can be obtained directly from bacteria using isolation procedures known to one of ordinary skill in the art. See, e.g., Fournier et al. (1984), supra; Fournier et al. (1987) *Ann. Inst. Pasteur/Microbiol.* 138: 561-567; US Patent Application Publication No. 2007/0141077; and Intl Patent Application Publication No. WO 00/56357; each of which is incorporated herein by reference as if set forth in its entirety). In addition, they can be produced using synthetic protocols. Moreover, capsular polysaccharide can be recombinantly produced using genetic engineering procedures also known to one of ordinary skill in the art (see, Sau et al. (1997) *Microbiology* 143:2395-2405; and U.S. Pat. No. 6,027,925; each of which is incorporated herein by reference as if set forth in its entirety).

Bacterial strains of *S. pneumoniae* or *N. meningitidis* or Group B Streptoccus or *S. aureus* or *Enterococcus* bacteria (such as *Enterococcus faecalis* or a *Enterococcus faecium*) used to make the respective polysaccharides that are used in the glycoconjugates of the invention may be obtained from established culture collections or clinical specimens.

Carrier Proteins

Another component of the glycoconjugate of the invention is a carrier protein to which the saccharide is conjugated. The terms "protein carrier" or "carrier protein" or "carrier" may be used interchangeably herein. Carrier proteins are preferably proteins that are non-toxic and non-reactogenic and obtainable in sufficient amount and purity. Carrier proteins should be amendable to standard conjugation procedures. In the novel glycoconjugates of the invention, the carrier protein is covalently linked to the saccharide through an oxo-eT spacer.

Conjugation to a carrier can enhance the immunogenicity of an antigen, for example bacterial antigen such as a bacterial capsular polysaccharide. Preferred protein carriers for the antigens are toxins, toxoids or any mutant cross-reactive material (CRM) of the toxin from tetanus, diphtheria, pertussis, *Pseudomonas, E. coli, Staphylococcus* and *Streptococcus*. In one embodiment, a particularly preferred carrier is of diphtheria toxoid $CRM_{197}$, derived from *C. diphtheriae* strain C7 (β197), which produces $CRM_{197}$ protein. This strain has ATCC accession No. 53281. A method for producing $CRM_{197}$ is described in U.S. Pat. No. 5,614,382, which is incorporated herein by reference as if set forth in its entirety.

Alternatively, a fragment or epitope of the protein carrier or other immunogenic protein can be used. For example, a haptenic antigen can be coupled to a T-cell epitope of a bacterial toxin, toxoid or CRM. See, US Patent Application No. 150,688, filed Feb. 1, 1988, entitled "Synthetic Peptides Representing a T-Cell Epitope as a Carrier Molecule For Conjugate Vaccines"; incorporated herein by reference as if set forth in its entirety. Other suitable carrier proteins include inactivated bacterial toxins such as cholera toxoid (e.g., as described in Int'l Patent Application No. WO 2004/083251), *E. coli* LT, *E. coli* ST, and exotoxin A from *Pseudomonas aeruginosa*. Bacterial outer membrane proteins such as outer membrane complex c (OMPC), porins, transferrin binding proteins, pneumolysin, pneumococcal surface protein A (PspA), pneumococcal adhesion protein (PsaA) or *Haemophilus influenzae* protein D also can be used. Other proteins, such as ovalbumin, keyhole limpet hemocyanin (KLH), bovine serum albumin (BSA) or purified protein derivative of tuberculin (PPD) also can be used as carrier proteins.

In an embodiment, preferred carrier is selected in the group consisting of: DT (Diphtheria toxoid), TT (tetanus toxoid) or fragment C of TT, CRM197 (a nontoxic but antigenically identical variant of diphtheria toxin), other DT mutants (such as CRM176, CRM228, CRM 45 (Uchida et al J. Biol. Chem. 218; 3838-3844, 1973), CRM9, CRM45, CRM102, CRM103 or CRM107; and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or 4,950,740; mutation of at least one or more residues Lys 516, Lys 526, Phe 530 and/or Lys 534 and other mutations disclosed in U.S. Pat. No. 5,917,017 or 6,455,673; or fragment disclosed in U.S. Pat. No. 5,843,711), pneumococcal pneumolysin (Kuo et al (1995) Infect Immun 63; 2706-13) including ply detoxified in some fashion for example dPLY-GMBS (WO 04081515, PCT/EP2005/010258) or dPLY-formol, PhtX, including PhtA, PhtB, PhtD, PhtE (sequences of PhtA, PhtB, PhtD or PhtE are disclosed in WO 00/37105 or WO 00/39299) and fusions of Pht proteins for example PhtDE fusions, PhtBE fusions, Pht A-E (WO 01/98334, WO 03/54007, WO2009/000826), OMPC (meningococcal outer membrane protein—usually extracted from *N. meningitidis* serogroup B—EP0372501), PorB (from *N. meningitidis*), PD (*Haemophilus influenzae* protein D—see, e.g., EP 0 594 610 B), or immunologically functional equivalents thereof, synthetic peptides (EP0378881, EP0427347), heat shock proteins (WO 93/17712, WO 94/03208), pertussis proteins (WO 98/58668, EP0471 177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of *C. difficile* (WO 00/61761), transferrin binding proteins, pneumococcal adhesion protein (PsaA), recombinant *Pseudomonas aeruginosa* exotoxin A (in particular non-toxic mutants thereof (such as exotoxin A bearing a substution at glutamic acid 553 (Uchida Cameron D M, R J Collier. 1987. J. Bacteriol. 169:4967-4971)). Other proteins, such as ovalbumin, keyhole limpet hemocyanin (KLH), bovine serum albumin (BSA) or purified protein derivative of tuberculin (PPD) also can be used as carrier proteins. Other suitable carrier proteins include inactivated bacterial toxins such as cholera toxoid (e.g., as described in Int'l Patent Application No. WO 2004/083251), *E. coli* LT, *E. coli* ST, and exotoxin A from *Pseudomonas aeruginosa*.

In an embodiment, the carrier is selected in the group consisting of TT, DT, DT mutants (such as CRM197), *H. influenzae* protein D, PhtX, PhtD, PhtDE fusions (particularly those described in WO 01/98334 and WO 03/54007), detoxified pneumolysin, PorB, N19 protein, PspA, OMPC, toxin A or B of *C. Difficile* and PsaA.

In a preferred embodiment, the carrier protein of the glycoconjugates of the invention is DT (Diphtheria toxoid). In another embodiment, the carrier protein of the glycoconjugates of the invention is TT (tetanus toxoid). In another embodiment, the carrier protein of the glycoconjugates of the invention is PD (*Haemophilus influenzae* protein D—see, e.g., EP 0 594 610 B).

In a most preferred embodiment, the capsular saccharides of the invention are conjugated to $CRM_{197}$ protein.

Accordingly, in frequent embodiments, the oxo-eT linked glycoconjugates comprise $CRM_{197}$ as the carrier protein, wherein the capsular polysaccharide is covalently linked to the oxo-eT spacer via a carbamate linkage, and wherein the $CRM_{197}$ is covalently linked to the oxo-eT spacer via an amide linkage formed by an activated amino acid residue of the protein, typically through the ε-amine group of one or more lysine residues.

The number of lysine residues in the carrier protein that become conjugated to the saccharide can be characterized as a range of conjugated lysines. For example, in some embodiments of the immunogenic compositions, the $CRM_{197}$ may comprise 4 to 16 lysine residues out of 39 covalently linked to the saccharide. Another way to express this parameter is that about 10% to about 41% of $CRM_{197}$ lysines are covalently linked to the saccharide. In other embodiments, the $CRM_{197}$ may comprise 2 to 20 lysine residues out of 39 covalently linked to the saccharide. Another way to express this parameter is that about 5% to about 50% of $CRM_{197}$ lysines are covalently linked to the saccharide.

The frequency of attachment of the saccharide chain to a lysine on the carrier protein is another parameter for characterizing the glycoconjugates of the invention. For example, in some embodiments, at least one covalent linkage between the carrier protein and the polysaccharide for every 4 saccharide repeat units of the polysaccharide. In another embodiment, the covalent linkage between the carrier protein and the polysaccharide occurs at least once in every 10 saccharide repeat units of the polysaccharide. In another embodiment, the covalent linkage between the carrier protein and the polysaccharide occurs at least once in every 15 saccharide repeat units of the polysaccharide. In a further embodiment, the covalent linkage between the carrier protein and the polysaccharide occurs at least once in every 25 saccharide repeat units of the polysaccharide.

In frequent embodiments, the carrier protein is $CRM_{197}$ and the covalent linkage via an oxo-eT spacer between the $CRM_{197}$ and the polysaccharide occurs at least once in every 4, 10, 15 or 25 saccharide repeat units of the polysaccharide. In some such embodiments, the polysaccharide is a bacterial capsular polysaccharide derived from *S. pneumoniae* or *N. meningitidis* or Group B *Streptococcus* or a *S. aureus* polysaccharide or an *Enterococcus* bacteria polysaccharide (such as *Enterococcus faecalis* or *Enterococcus faecium*).

In other embodiments, the conjugate comprises at least one covalent linkage between the carrier protein and saccharide for every 5 to 10 saccharide repeat units; every 2 to 7 saccharide repeat units; every 3 to 8 saccharide repeat units; every 4 to 9 saccharide repeat units; every 6 to 11 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 11 saccharide repeat units; every 8 to 12 saccharide repeat units; every 9 to 13 saccharide repeat units; every 10 to 14 saccharide repeat units; every 10 to 20 saccharide repeat units; or every 4 to 25 saccharide repeat units.

In another embodiment, at least one linkage between carrier protein and saccharide occurs for every 2, 3, 4, 5, 6, 7, 8, 9, 10, 11, 12, 13, 14, 15, 16, 17, 18, 19, 20, 21, 22, 23, 24 or 25 saccharide repeat units of the polysaccharide.

Methods for Making Oxo-eT Linked Glycoconjugates

Methods for Making Oxo-eTAC Linked Glycoconjugates

The present invention provides methods of making oxo-eTAC linked glycoconjugates comprising a saccharide covalently conjugated to a carrier protein through a (((2-oxoethyl)thio)alkyl)carbamate (oxo-eTAC) spacer. The oxo-eTAC spacer, comprising stable carbamate, thioether and amide bonds, and serves to covalently link the saccharide and carrier protein. One end of the oxo-eTAC spacer is covalently bound to a hydroxyl group of the saccharide through a carbamate linkage. The other end of the oxo-eTAC spacer is covalently bound to an amino-containing residue of the carrier protein, typically an ε-lysine residue, through an amide linkage.

A representative route to the preparation of glycoconjugates of the present invention, comprising a polysaccharide conjugated to the activated carrier protein $CRM_{197}$, is shown in FIG. 1.

Methods for Making Oxo-eTAAN Linked Glycoconjugates

The present invention provides methods of making oxo-eTAAN linked glycoconjugates comprising a saccharide covalently conjugated to a carrier protein through a (((2-oxoethyl)thio)alkyl)amine (oxo-eTAAN) spacer. The oxo-eTAAN spacer contains stable amine, thioether and amide bonds, and serves to covalently link the saccharide and carrier protein. One end of the oxo-eTAAN spacer is covalently bound to a carbon atom of the saccharide through an amine linkage. The other end of the oxo-eTAAN spacer is covalently bound to an amino-containing residue of the carrier protein, typically an ε-lysine residue, through an amide linkage.

Figure 2:
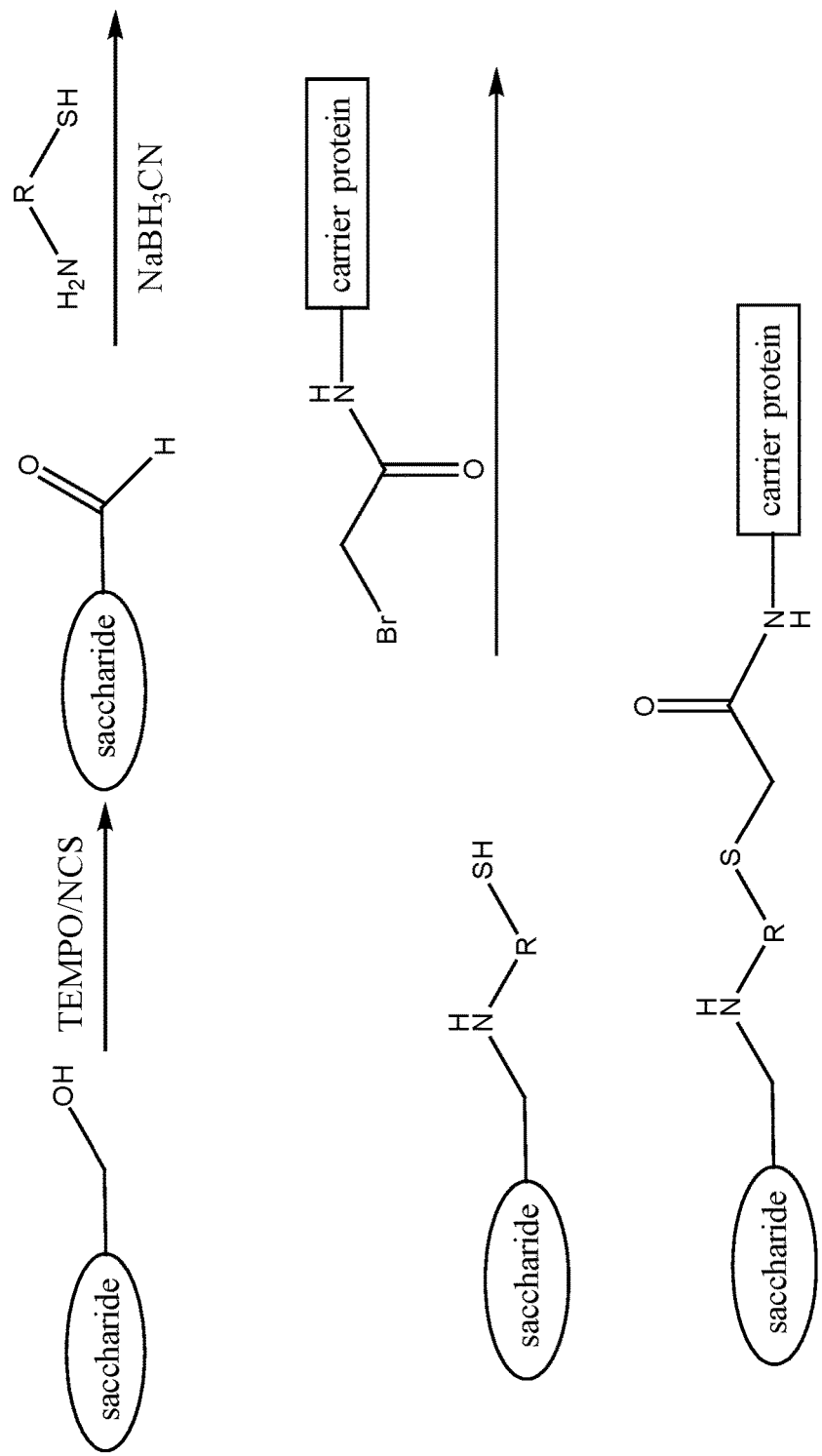
FIG. 2 shows a general scheme for the preparation of oxo-eTAAN linked glycoconjugates of the invention, for a glycoconjugate comprising a polysaccharide covalently conjugated to $CRM_{197}$.

A representative route to the preparation of glycoconjugates of the present invention, comprising a polysaccharide conjugated to the activated carrier protein $CRM_{197}$, is shown in FIG. 2.

Methods for Making Oxo-eTAAD Linked Glycoconjugates

The present invention provides methods of making oxo-eTAAD linked glycoconjugates comprising a saccharide covalently conjugated to a carrier protein through a (((2-oxoethyl)thio)alkyl)amide (oxo-eTAAD) spacer. The oxo-eTAAD spacer contains stable amide, thioether and amide bonds, and serves to covalently link the saccharide and carrier protein. One end of the oxo-eTAAD spacer is covalently bound to a carboxyl group of the saccharide through an amide linkage. The other end of the oxo-eTAAD spacer is covalently bound to an amino-containing residue of the carrier protein, typically an ε-lysine residue, through an amide linkage.

Figure 3:
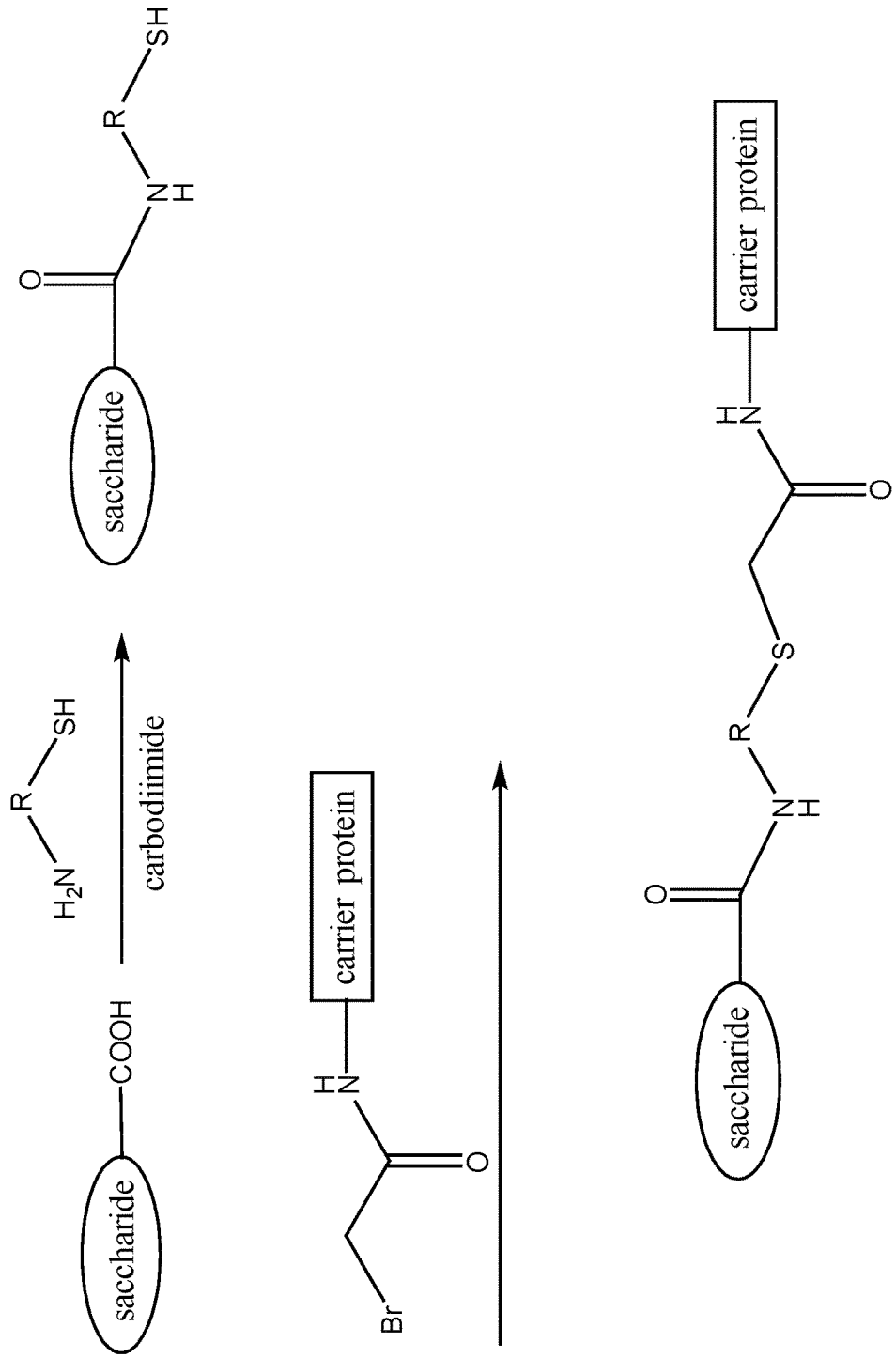
FIG. 3 shows a general scheme for the preparation of oxo-eTAAD linked glycoconjugates of the invention, for a glycoconjugate comprising a polysaccharide covalently conjugated to $CRM_{197}$.

A representative route to the preparation of glycoconjugates of the present invention, comprising a polysaccharide conjugated to the activated carrier protein $CRM_{197}$, is shown in FIG. 3.

Methods for Making Oxo-eTAAD Linked Glycoconjugates Via Thiazolidinone Activation Route The present invention provides methods of making oxo-eTAAD linked glycoconjugates comprising a saccharide covalently conjugated to a carrier protein through a (((2-oxoethyl)thio)alkyl)amide (oxo-eTAAD) spacer. The oxo-eTAAD spacer contains stable amide, thioether and amide bonds, and serves to covalently link the saccharide and carrier protein. One end of the oxo-eTAAD spacer is covalently bound to a carboxyl group of the saccharide through an amide linkage. The other end of the oxo-eTAAD spacer is covalently bound to an amino-containing residue of the carrier protein, typically an ε-lysine residue, through an amide linkage.

Figure 4:
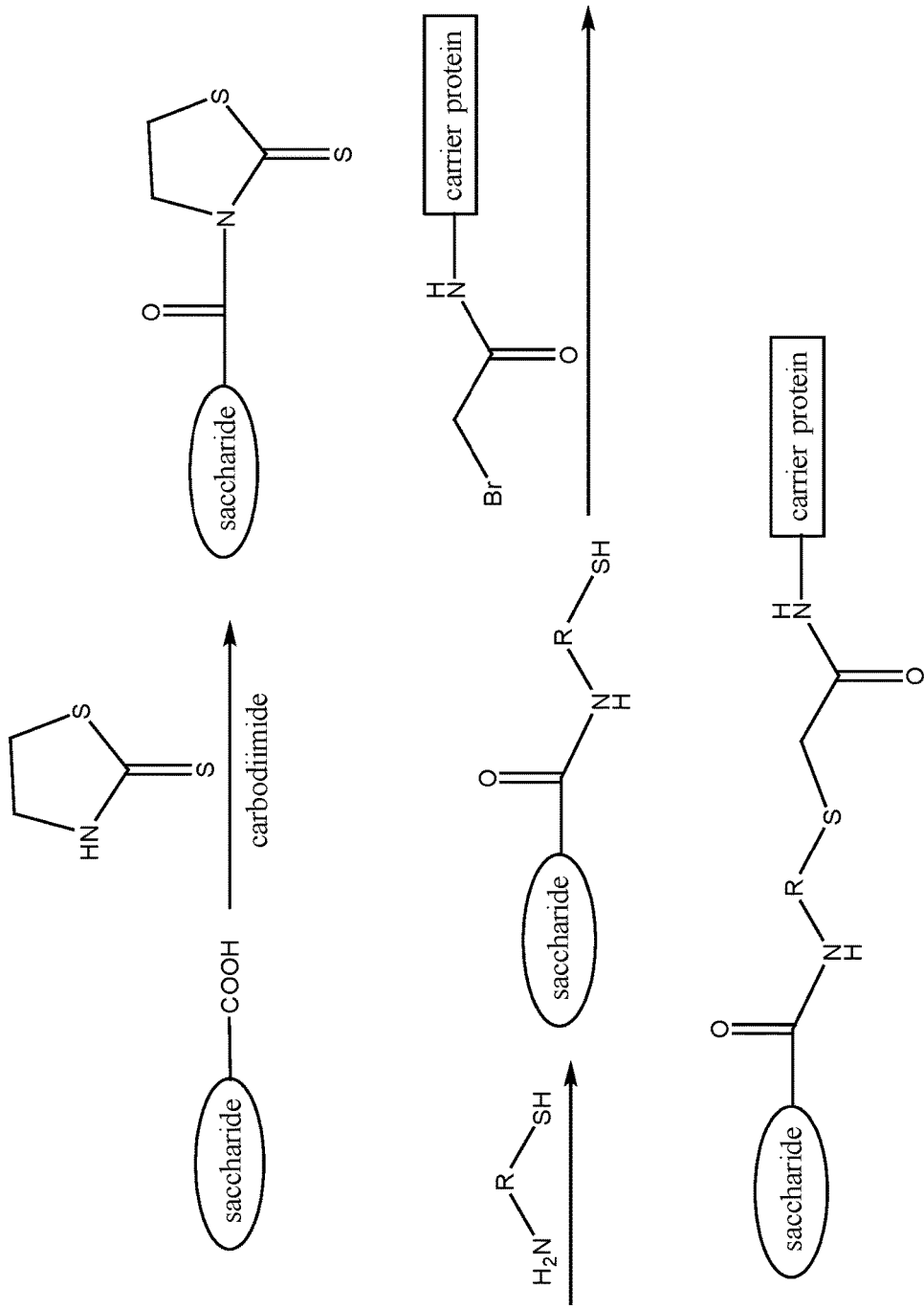
FIG. 4 shows a general scheme for the preparation of oxo-eTAAD linked glycoconjugates of the invention, using thiazolidinonethione derivative, for a glycoconjugate comprising a polysaccharide covalently conjugated to $CRM_{197}$.
Figure 5:
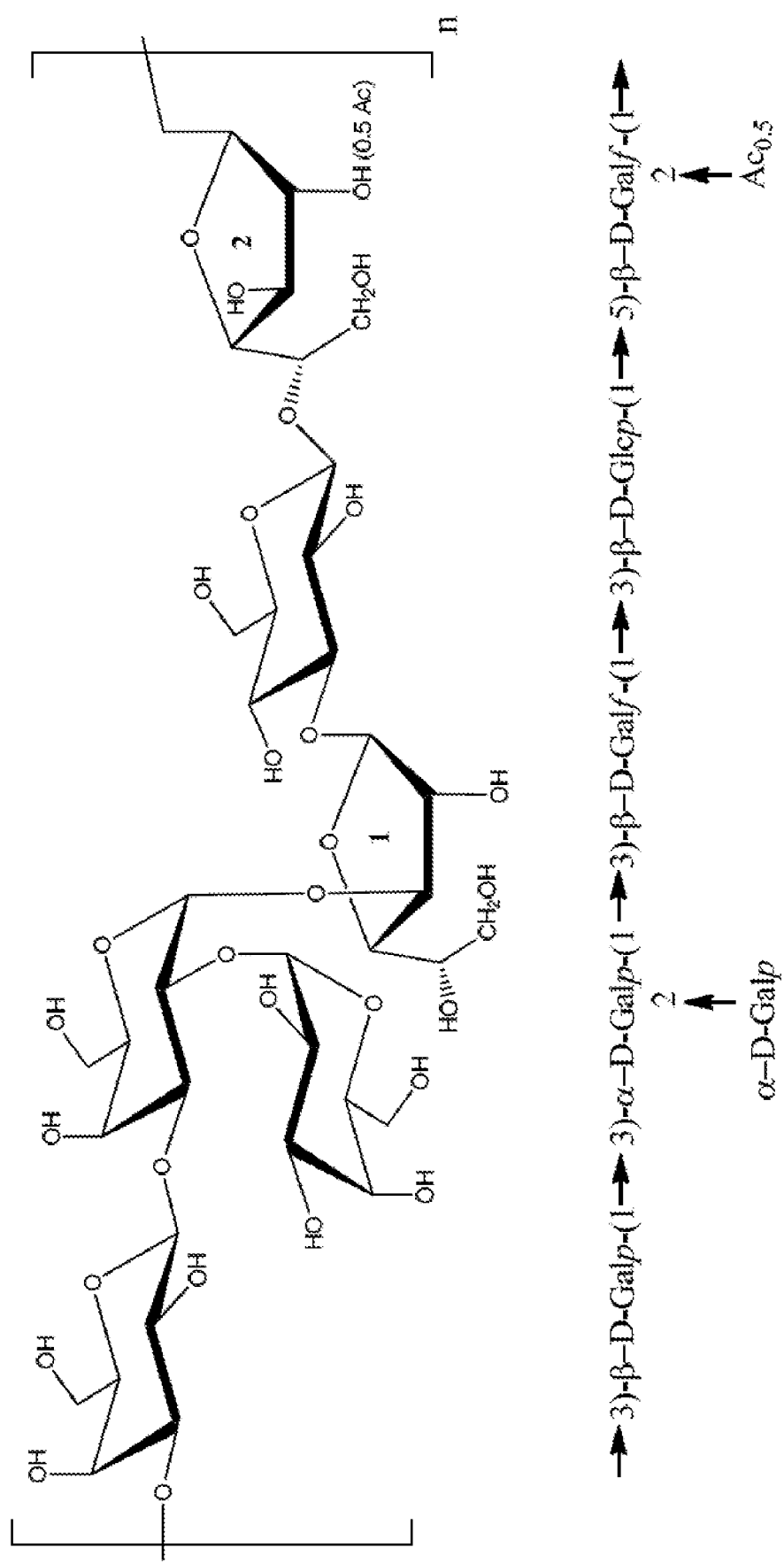
FIG. 5 shows a repeating polysaccharide structure of *S. pneumoniae* serotype 33F (Pn-33F) capsular polysaccharide.
Figure 6:
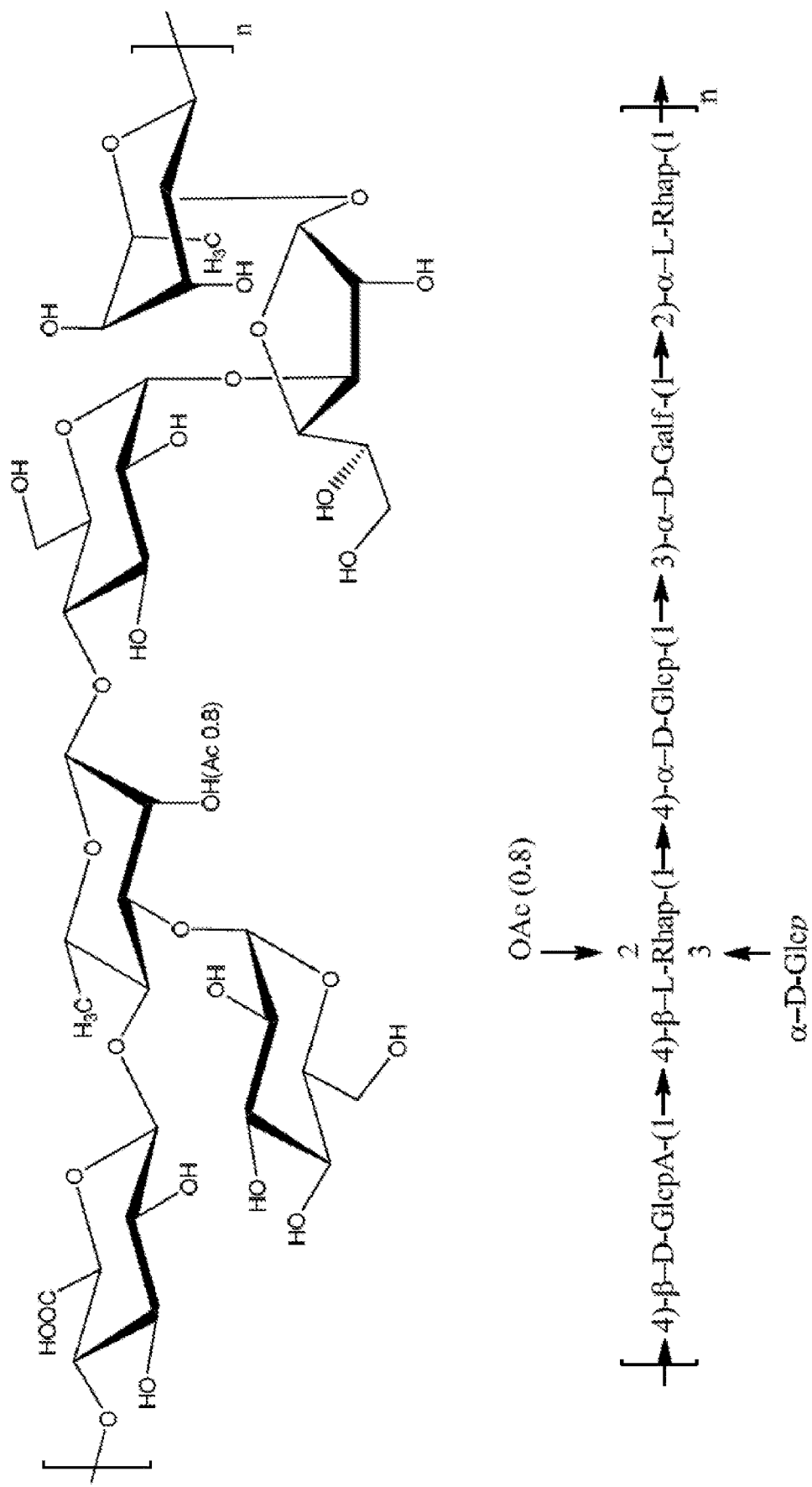
FIG. 6 shows a repeating polysaccharide structure of *S. pneumoniae* serotype 22F (Pn-22F) capsular polysaccharide.
Figure 7:
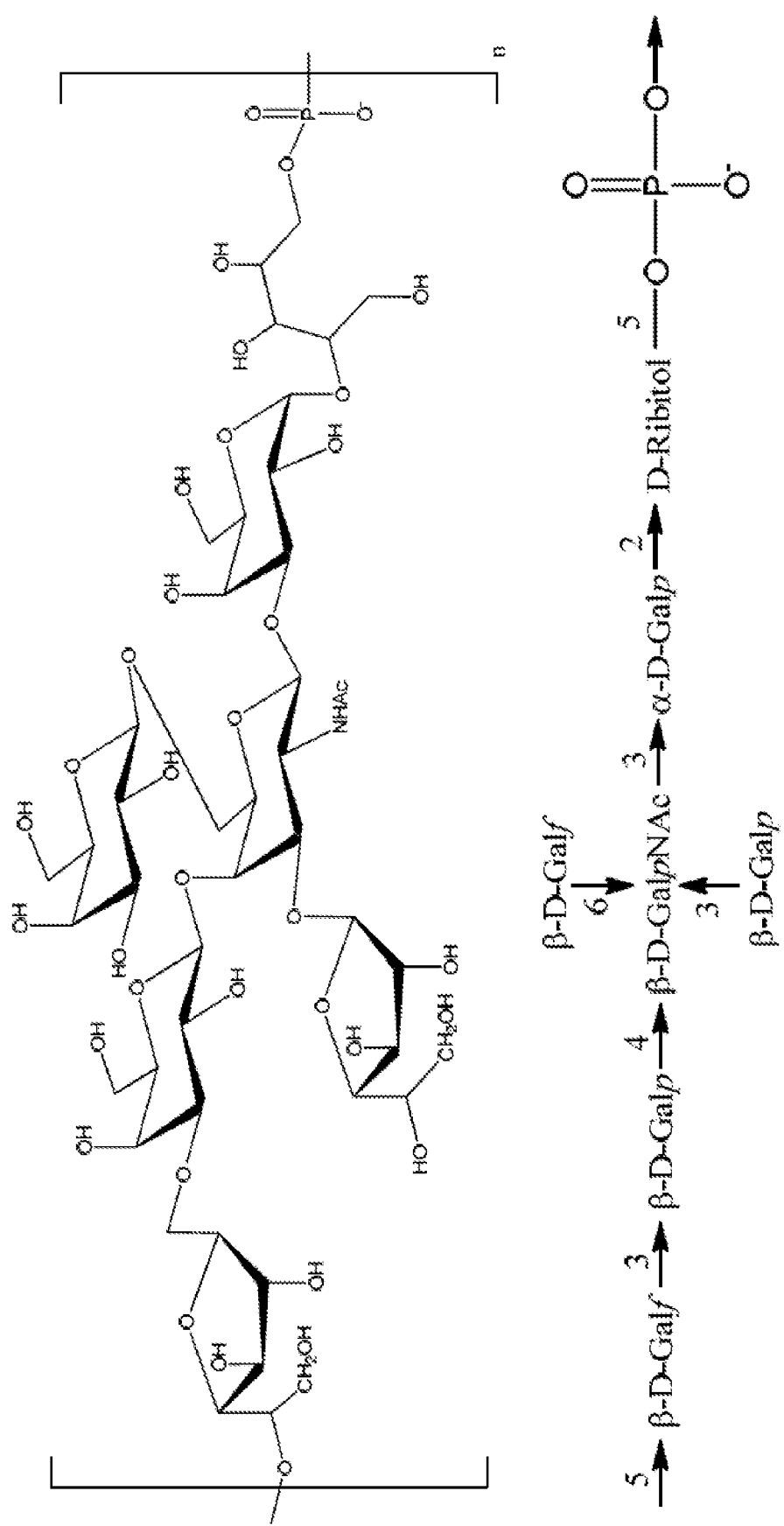
FIG. 7 shows a repeating polysaccharide structure of *S. pneumoniae* serotype 10A (Pn-10A) capsular polysaccharide.
Figure 8:
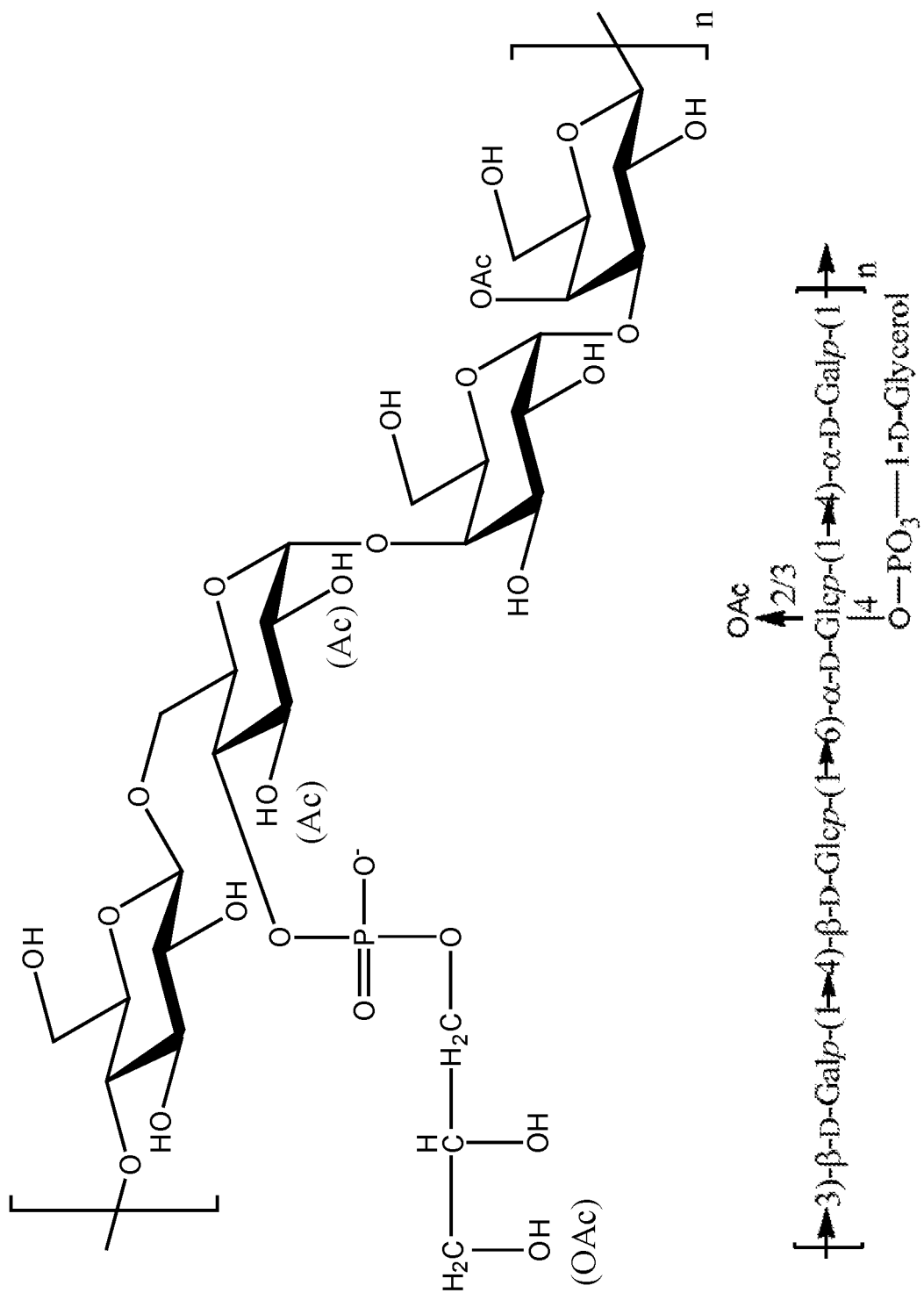
FIG. 8 shows a repeating polysaccharide structure of *S. pneumoniae* serotype 11A (Pn-11A) capsular polysaccharide.

A representative route to the preparation of glycoconjugates of the present invention, via thiazolidinone activation, comprising a polysaccharide conjugated to the activated carrier protein $CRM_{197}$, is shown in FIG. 4.

The chemical structure of a representative bacterial capsular polysaccharide, pneumococcal serotypes 33F, 10A, 11A and 22F polysaccharides derived from *S. pneumoniae*, having potential sites of modification using the oxo-eT spacer process are shown in FIG. 5, FIG. 6, FIG. 7 and FIG. 8, respectively.

In one aspect, the method of making oxo-eTAC linked glycoconjugate comprises the steps of: a) reacting a saccharide with a carbonic acid derivative, such as 1,1'-carbonyl-di-(1,2,4-triazole) (CDT) or 1,1'-carbonyldiimidazole (CDI), in an organic solvent to produce an activated saccharide; b) reacting the activated saccharide with heterobifunctional linker reagent having amine and thiol functionalities or a salt thereof, to produce a thiolated saccharide; c) reacting the thiolated saccharide with a reducing agent to produce an activated thiolated saccharide comprising one or more free sulfhydryl residues; d) reacting the activated thiolated saccharide with an activated carrier protein comprising one or more α-haloacetamide groups, to produce a thiolated saccharide-carrier protein conjugate; and e) reacting the thiolated saccharide-carrier protein conjugate with (i) a first capping reagent capable of capping unconjugated α-haloacetamide groups of the activated carrier protein; and/or (ii) a second capping reagent capable of capping unconjugated free sulfhydryl residues of the activated thiolated saccharide; whereby an oxo-eTAC linked glycoconjugate is produced.

In a particularly preferred embodiment, the method comprises the steps of: a) reacting a Pn-33F capsular polysaccharide with CDT or CDI in an organic solvent to produce an activated Pn-33F polysaccharide; b) reacting the activated Pn-33F polysaccharide with a heterobifunctional linker reagent having amine and thiol functionalities or a salt thereof, to produce a thiolated Pn-33F polysaccharide; c) reacting the thiolated Pn-33F polysaccharide with a reducing agent to produce an activated thiolated Pn-33F polysaccharide comprising one or more free sulfhydryl residues; d) reacting the activated thiolated Pn-33F polysaccharide with an activated $CRM_{197}$ carrier protein comprising one or more α-bromoacetamide groups, to produce a thiolated Pn-33F polysaccharide-$CRM_{197}$ conjugate; and e) reacting the thiolated Pn-33F polysaccharide-$CRM_{197}$ conjugate with (i) N-acetyl-L-cysteine as a first capping reagent capable of capping unconjugated α-bromoacetamide groups of the activated carrier protein; and (ii) iodoacetamide as a second capping reagent capable of capping unconjugated free sulfhydryl residues of the activated thiolated Pn-33F polysaccharide; whereby an oxo-eTAC linked Pn-33F polysaccharide-$CRM_{197}$ glycoconjugate is produced.

In frequent embodiments, the carbonic acid derivative is CDT or CDI or DSC or N-hydroxysuccinimidyl chloroformate. Preferably the carbonic acid derivative is CDT, and the organic solvent is a polar aprotic solvent, such as dimethylsulfoxide (DMSO). Lyophilization of the activated saccharide is not required prior to the thiolation and/or conjugation steps.

In a preferred embodiment, the thiolated saccharide is produced by reaction of the activated saccharide with the bifunctional symmetric thioalkylamine reagent, in the disulfide form, or a salt thereof. A potential advantage to this reagent is that the symmetrical thioalkylamine linker, in the disulfide form, can react with two molecules of activated saccharide, thus forming two molecules of thiolated saccharide per molecule of thioalkylamine upon reduction of the disulfide bond. Alternatively, the thiolated saccharide may be formed by reaction of the activated saccharide with thioalkylamine in the monomeric form, or a salt thereof. The oxo-eT linked glycoconjugates produced by the methods of the invention may be represented by general formula (I).

In some embodiments of this aspect, step d) further comprises providing an activated carrier protein comprising one or more α-haloacetamide groups, prior to reacting the activated thiolated saccharide with the activated carrier protein, to produce a thiolated saccharide-carrier protein conjugate. In frequent embodiments, the activated carrier protein comprises one or more α-bromoacetamide groups.

The thiolated saccharide-carrier protein conjugate may be treated with one or more capping reagents capable of reacting with residual activated functional groups present in the reaction mixture. Such residual reactive groups may be present on unreacted saccharide or carrier protein components, due to incomplete conjugation or from the presence of an excess of one of the components in the reaction mixture. In that case, capping may aid in the purification or isolation of the glycoconjugate. In some cases, residual activated functional groups may be present in the glycoconjugate.

For example, excess α-haloacetamide groups on the activated carrier protein may be capped by reaction with a low molecular weight thiol, such as N-acetyl-L-cysteine, which may be used in excess to ensure complete capping. Capping with N-acetyl-L-cysteine also permits confirmation of the conjugation efficiency, by detection of the unique amino acid S-carboxymethylcysteine (CMC) from the cysteine residues at the capped sites, which can be determined by acidic hydrolysis and amino acid analysis of the conjugation products. Detection of this amino acid confirms successful capping of the reactive bromoacetamide groups, thus making them unavailable for any unwanted chemical reactions. Acceptable levels of covalency and capping are between about 1-15 for CMCA/Lys and about 0-5 for CMC/Lys. Similarly, excess free sulfhydryl residues can be capped by reaction with a low molecular weight electrophilic reagent, such as iodoacetamide. A portion of the CMCA may be derived from the polysaccharide thiols capped directly by iodoacetamide that were not involved in conjugation with the haloacyl groups of the carrier protein. Therefore, post-conjugation reaction samples (prior to capping by iodoacetamide) need to be examined by amino acid analysis (CMCA) to determine the accurate levels of thiols involved directly in conjugation. For a thiolated saccharide containing 10-12 thiols, typically 5-6 thiols are determined to be involved directly in the conjugation between the polysaccharide thiol and bromoacetylated protein and 4-5 thiols are capped by iodoacetamide.

In preferred embodiments, the first capping reagent is N-acetyl-L-cysteine, which reacts with unconjugated α-haloacetamide groups on the carrier protein. In other embodiments, the second capping reagent is iodoacetamide (IAA), which reacts with unconjugated free sulfhydryl groups of the activated thiolated saccharide. Frequently, step e) comprises capping with N-acetyl-L-cysteine as the first capping reagent and IAA as the second capping reagent. In some embodiments, the capping step e) further comprises reaction with a reducing agent, for example, DTT, TCEP, or mercaptoethanol, after reaction with the first and/or second capping reagent.

In some embodiments, the method further comprises a step of purifying the oxo-eT linked glycoconjugate, for example, by ultrafiltration/diafiltration.

In a preferred embodiment, the bifunctional symmetric thioalkylamine reagent is cystamine or a salt thereof is reacted with the activated saccharide to provide a thiolated saccharide or a salt thereof which contains a disulfide moiety.

Reaction of such thiolated saccharide derivatives with a reducing agent produces an activated thiolated polysaccharide comprising one or more free sulfhydryl residues (if thiol is protected). Such activated thiolated saccharides can be isolated and purified, for example, by ultrafiltration/diafiltration. Alternatively, the activated thiolated saccharides can be isolated and purified, for example, by standard size exclusion chromatographic (SEC) methods or ion exchange chromatographic methods such as DEAE known in the art.

In the case of cystamine-derived, thiolated saccharides, reaction with a reducing agent cleaves the disulfide bond to provide an activated thiolated saccharide comprising one or more free sulfhydryl residues. In the case of cysteamine-derived, thiolated saccharides, reaction with a reducing agent is optional and may be used to reduce disulfide bonds formed by oxidation of the reagent or product.

Reducing agents used in the methods of the invention include, for example, tris(2-carboxyethyl)phosphine (TCEP), dithiothreitol (DTT) or mercaptoethanol. However, any suitable disulfide reducing agent may be used.

In some embodiments, the methods further comprise providing an activated carrier protein comprising one or more α-haloacetamide groups, preferably one or more α-bromoacetamide groups.

Reaction of the activated thiolated saccharide with an activated carrier protein comprising one or more α-haloacetamide moieties results in nucleophilic displacement of the α-halo group of the activated carrier protein by the one or more free sulfhydryl groups of the activated thiolated saccharide, forming the thioether bond of the oxo-eT spacer.

The α-haloacetylated amino acid residues of the carrier protein are typically attached to the ε-amino groups of one or more lysine residues of the carrier protein. In frequent embodiments, the carrier protein contains one or more α-bromoacetylated amino acid residues. In one embodiment, the carrier protein is activated with a bromoacetic acid reagent, such as the N-hydroxysuccinimide ester of bromoacetic acid (BAANS).

In one embodiment, the method includes the step of providing an activated carrier protein comprising one or more α-haloacetamide groups and reacting the activated thiolated polysaccharide with the activated carrier protein to produce a thiolated polysaccharide-carrier protein conjugate, whereby a glycoconjugate comprising a polysaccharide conjugated to a carrier protein through an oxo-eT spacer is produced.

In some preferred embodiments of the methods herein, the bacterial capsular polysaccharide is a Pn capsular polysaccharide derived from S. pneumoniae. In some such embodiments, the Pn capsular polysaccharide is selected from the group consisting of Pn-serotype 1, 3, 4, 5, 6A, 6B, 7F, 8, 9V, 10A, 11A, 12F, 14, 15B, 18C, 19A, 19F, 22F, 23F and 33F capsular polysaccharides. In certain preferred embodiments, the carrier protein is $CRM_{197}$ and the Pn capsular polysaccharide is selected from the group consisting of Pn-serotype 1, 3, 4, 5, 6A, 6B, 7F, 8, 9V, 10A, 11A, 12F, 14, 15B, 18C, 19A, 19F, 22F, 23F and 33F capsular polysaccharides.

In other preferred embodiments of the methods provided herein, the bacterial capsular polysaccharide is a Mn capsular polysaccharide derived from N. meningitidis. In some such embodiments, the Mn capsular polysaccharide is selected from the group consisting of Mn-serotype A, C, W135 and Y capsular polysaccharides. In certain preferred embodiments, the carrier protein is $CRM_{197}$ and the capsular polysaccharide is selected from the group consisting of Mn-serotype A, C, W135 and Y capsular polysaccharides.

In other preferred embodiments of the methods provided herein, the bacterial capsular polysaccharide is a GBS capsular polysaccharide derived from Group B *Streptococcus*. In some such embodiments, the GBS capsular polysaccharide is selected from the group consisting of GBS-serotype Ia, Ib, II, III and V capsular polysaccharides. In certain preferred embodiments, the carrier protein is $CRM_{197}$ and the capsular polysaccharide is selected from the group consisting of GBS-serotype Ia, Ib, II, III and V capsular polysaccharides.

In some embodiments of each of methods provided herein, the saccharide was compounded with imidazole or triazole and then reacted with a carbonic acid derivative, such as CDT, in an organic solvent (e.g., DMSO) containing about 0.2% w/v water to produce activated saccharides. Use of the compounded saccharide in the activation step increases the solubility of the saccharide in the organic solvent. Typically, the saccharide was compounded with 10 grams of 1,2,4-triazole excipient per gram of polysaccharide followed by mixing at ambient temperature to provide a compounded saccharide.

Thus, in certain embodiments the methods further comprise a step of compounding the saccharide with triazole or imidazole to give a compounded saccharide prior to the activation step a). In some such embodiments, the compounded saccharide is shell-frozen, lyophilized and reconstituted in an organic solvent (such as DMSO) and about 0.2% w/v water is added before activation with the carbonic acid derivative, e.g., CDT.

In one embodiment, the thiolated saccharide reaction mixture is optionally treated with N-acetyl-lysine methyl ester to cap any unreacted activated saccharide. In some such embodiments, the capped thiolated saccharide mixture is purified by ultrafiltration/diafiltration.

In frequent embodiments, the thiolated saccharide is reacted with a reducing agent to produce an activated thiolated saccharide. In some such embodiments, the reducing agent is tris(-2-carboxyethyl)phosphine (TCEP), dithiothreitol (DTT) or mercaptoethanol. In some such embodiments, the activated thiolated saccharide is purified by ultrafiltration/diafiltration.

In one embodiment the method of producing an oxo-eT linked glycoconjugate comprises the step of adjusting and maintaining the pH of the reaction mixture of activated thiolated saccharide and carrier protein to a pH of about 8 to about 9 for about 20 hours at about 5° C.

In one embodiment, the method of producing a glycoconjugate of the invention comprises the step of isolating the thiolated saccharide-carrier protein conjugate after it is produced. In frequent embodiments, the glycoconjugate is isolated by ultrafiltration/diafiltration.

In another embodiment, the method of producing an oxo-eT linked glycoconjugate of the invention comprises the step of isolating the isolated saccharide-carrier protein conjugate after it is produced. In frequent embodiments, the glycoconjugate is isolated by ultrafiltration/diafiltration.

In yet another embodiment, the method of producing the activated saccharide comprises the step of adjusting the water concentration of the reaction mixture comprising saccharide and CDT in an organic solvent to between about 0.1 and 0.4%. In one embodiment, the water concentration of the reaction mixture comprising saccharide and CDT in an organic solvent is adjusted to about 0.2%.

In one embodiment, the step of activating the saccharide comprises reacting the polysaccharide with an amount of CDT that is about a 5 molar excess to the amount of polysaccharide present in the reaction mixture comprising capsular polysaccharide and CDT in an organic solvent.

In another embodiment, the method of producing the glycoconjugate of the invention comprises the step of determining the water concentration of the reaction mixture comprising saccharide. In one such embodiment, the amount of CDT added to the reaction mixture to activate the saccharide is provided in about an amount of CDT that is equimolar to the amount of water present in the reaction mixture comprising saccharide and CDT in an organic solvent.

In another embodiment, the amount of CDT added to the reaction mixture to activate the saccharide is provided in about an amount of CDT that is at a molar ratio of about 0.5:1 compared to the amount of water present in the reaction mixture comprising saccharide and CDT in an organic solvent. In one embodiment, the amount of CDT added to the reaction mixture to activate the saccharide is provided in about an amount of CDT that is at a molar ratio of 0.75:1 compared to the amount of water present in the reaction mixture comprising saccharide and CDT in an organic solvent.

In one embodiment, the method comprises the step of isolating the thiolated polysaccharide by diafiltration. In another embodiment, the method comprises the step of isolating the activated thiolated polysaccharide by diafiltration.

In one embodiment, the carrier protein used in the method of producing an isolated Pn capsular polysaccharide-carrier protein conjugate comprises $CRM_{197}$. In another embodiment, the carrier protein used in the method of producing an isolated Mn capsular polysaccharide-carrier protein conjugate comprises $CRM_{197}$.

In some embodiments, the saccharide:activated carrier protein ratio (w/w) is between 0.2 and 4. In other embodiments, the saccharide:activated carrier protein ratio (w/w) is between 1.0 and 2.5. In further embodiments, the saccharide:activated carrier protein ratio (w/w) is between 0.4 and 1.7. In other embodiments, the saccharide:activated carrier protein ratio (w/w) is about 1:1. In some such embodiments, the saccharide is a bacterial capsular polysaccharide and the activated carrier protein is generated by the activation (bromoacetylation) of $CRM_{197}$.

In another embodiment, the method of producing the activated saccharide comprises the use of an organic solvent. In frequent embodiments, the organic solvent is a polar aprotic solvent. In some embodiments, the polar aprotic solvent is selected from the group consisting of dimethyl sulfoxide (DMSO), dimethylformamide (DMF), dimethylacetamide (DMA), N-methyl-2-pyrrolidone (NMP), acetonitrile, 1,3-Dimethyl-3,4,5,6-tetrahydro-2(1H)-pyrimidinone (DMPU) and hexamethylphosphoramide (HMPA), or a mixture thereof. In a preferred embodiment, the organic solvent is DMSO.

In frequent embodiments, isolation of the oxo-eT linked glycoconjugate comprises a step of ultrafiltration/diafiltration.

In one embodiment, the saccharide used in the method of producing the glycoconjugate of the invention has a molecular weight between about 10 kDa and about 2,000 kDa. In another embodiment, the saccharide used in the method of producing the glycoconjugate of the invention has a molecular weight between about 50 kDa and about 2,000 kDa.

In one embodiment, glycoconjugate produced in the method of producing capsular polysaccharide-carrier protein glycoconjugate has a size between about between 50 kDa and about 20,000 kDa. In another embodiment, glycoconjugate produced in the method of producing capsular polysaccharide-carrier protein glycoconjugate has a size between about between 500 kDa and about 10,000 kDa. In one embodiment, glycoconjugate produced in the method of producing capsular polysaccharide-carrier protein glycoconjugate has a size between about between 1,000 kDa and about 3,000 kDa.

In another aspect, the invention provides an oxo-eT linked glycoconjugate comprising a saccharide conjugated to a carrier protein through an oxo-eT spacer, produced by any of the methods disclosed herein.

In another aspect, the invention provides an immunogenic composition comprising an oxo-eT linked glycoconjugate produced by any of the methods described herein.

The degree of 0-acetylation of the saccharide can be determined by any method known in the art, for example, by proton NMR (Lemercinier and Jones (1996) *Carbohydrate Research* 296; 83-96, Jones and Lemercinier (2002) *J. Pharmaceutical and Biomedical Analysis* 30; 1233-1247, WO 05/033148 or WO 00/56357). Another commonly used method is described by Hestrin (1949) *J. Biol. Chem.* 180; 249-261. Yet another method is based on HPLC-ion-exclusion chromatography. The degree of O-acetylation is determined by assessing the amount of free acetate present in a sample and comparing that value to the amount of released acetate following a mild base hydrolysis. Acetate is resolved from other components of the sample and quantitated with a Ultra-Violet (UV) detection at 210 nm. Another method is based on HPLC-ion-exclusion chromatography. O-Acetyl is determined by assessing the amount of free acetate present in a sample and comparing that value to the amount of released acetate following a mild base hydrolysis. Acetate is resolved from other components of the sample and quantitated with a Ultra-Violet (UV) detection at 210 nm.

Degree of Conjugation Determined by Amino Acid Analysis

Acid hydrolysis of the "pre-IAA capped" conjugate samples generated using bromoacetyl activation chemistry resulted in the formation of acid stable carboxymethylthioalkylamine (CMTA) from the conjugated sites and acid stable S-carboxymethylcysteine (CMC) from the cysteines at the capped sites. Acid hydrolysis of the "post-IAA capped" conjugates (final) generated using the bromoacetyl activation chemistry also resulted in the formation of acid stable (CMTA) from the conjugated sites and IAA capped sites as well and acid stable S-carboxymethylcysteine (CMC) from the cysteines at the capped sites. All of the unconjugated and uncapped lysines were converted back to lysine and detected as such. All other amino acids were hydrolyzed back to free amino acids except for tryptophan and cysteine, which were destroyed by the hydrolysis conditions. Asparagine and glutamine were converted to aspartic acid and glutamic acid respectively.

The amino acids of each hydrolyzed sample and control were separated using ion exchange chromatography followed by reaction with Beckman Ninhydrin NinRX solution at 135° C. The derivatized amino acids were then detected in the visible range at 570 nm and 440 nm (see Table 1). A standard set of amino acids [Pierce Amino Acid Standard H] containing 500 picomoles of each amino acid was run along with the samples and controls for each set of analysis. S-carboxymethylcysteine [Sigma-Aldrich] was added to the standard.

TABLE 1

Retention Times for Amino Acids Using Gradient Program 1 on the Beckman 6300 Amino Acid Analyzer

| RETENTION TIME (MIN.) | AMINO ACID | | WAVELENGTH USED FOR DETECTION |
|---|---|---|---|
| 8.3 | Carboxymethylcysteine | CMC | 570 |
| 9.6 | Aspartic Acid & Asparagine | Asx | 570 |
| 11.3 | Threonine | Thr | 570 |
| 12.2 | Serine | Ser | 570 |
| 15.8 | Glutamic Acid & Glutamine | Glx | 570 & 440 |
| 18.5 | Proline | Pro | 440 |
| 21.8 | Glycine | Gly | 570 |
| 23.3 | Alanine | Ala | 570 |
| 29.0 | Valine | Val | 570 |
| 32.8 | Methionine | Met | 570 |
| 35.5 | Isoleucine | Ile | 570 |
| 36.8 | Leucine | Leu | 570 |
| 40.5 | Tyrosine | Tyr | 570 |
| 42.3 | Phenylalanine | Phe | 570 |
| 45.4 | Carboxymethylcysteamine | CMCA | 570 |
| 48.8 | Histidine | His | 570 |
| 53.6 | Lysine | Lys | 570 |
| 70.8 | Arginine | Arg | 570 |

Lysine was chosen for the evaluation based on its covalent attachment to Cysteine and Cysteamine and the expected similar hydrolysis. The resulting numbers of moles of amino acids were then compared to the amino acid composition of the protein and reported along with the values for CMC, CMTA or CMCA (in case of Cysteamine linker). The pre-IAA-CMTA value was used directly for evaluation of the degree of conjugation, the CMC value was used directly for evaluation of the degree of first capping and the Post-IAA-CMTA value was used for evaluation of the degree of IAA (second) capping.

In one embodiment, the glycoconjugate is characterized by its molecular size distribution ($K_d$). The molecular size of the conjugates is determined by Sepharose CL-4B stationary phase size exclusion chromatography (SEC) media using high pressure liquid chromatography system (HPLC). For $K_d$ determination, the chromatography column is first calibrated to determine $V_0$, which represents the void volume or total exclusion volume and $V_i$, the volume at which the smallest molecules in the sample elute, also known as interparticle volume. All SEC separation takes place between $V_0$ and $V_i$. $K_d$ value for each fraction collected is determined by the following expression $K_d=(V_e-V_i)/(V_i-V_0)$ where $V_e$ represents the retention volume of the compound. The % fraction (major peak) that elutes ≤0.3 defines the conjugate $K_d$ (molecular size distribution).

Immunogenic Compositions

The term "immunogenic composition" relates to any pharmaceutical composition containing an antigen (e.g., a microorganism or a component thereof) which can be used to elicit an immune response in a subject.

As used herein, "immunogenic" means an ability of an antigen (or an epitope of the antigen), such as a bacterial capsular polysaccharide, or a glycoconjugate or immunogenic composition comprising a bacterial capsular polysaccharide, to elicit an immune response in a host subject, such as a mammal, either humorally or cellularly mediated, or both.

The glycoconjugate may serve to sensitize the host by the presentation of the antigen in association with MHC molecules at a cell surface. In addition, antigen-specific T-cells or antibodies can be generated to allow for the future protection of an immunized host. Glycoconjugates thus can protect the host from one or more symptoms associated with infection by the bacteria, or may protect the host from death due to the infection with the bacteria associated with the capsular polysaccharide. Glycoconjugates may also be used to generate polyclonal or monoclonal antibodies, which may be used to confer passive immunity to a subject. Glycoconjugates may also be used to generate antibodies that are functional as measured by the killing of bacteria in either an animal efficacy model or via an opsonophagocytic killing assay.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, unless otherwise indicated by context, the term is intended to encompass not only intact polyclonal or monoclonal antibodies, but also engineered antibodies (e.g., chimeric, humanized and/or derivatized to alter effector functions, stability and other biological activities) and fragments thereof (such as Fab, Fab', F(ab')2, Fv), single chain (ScFv) and domain antibodies, including shark and camelid antibodies), and fusion proteins comprising an antibody portion, multivalent antibodies, multispecific antibodies (e.g., bispecific antibodies so long as they exhibit the desired biological activity) and antibody fragments as described herein, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2 in humans. The heavy-chain constant domains that correspond to the different classes of immunoglobulins are called alpha, delta, epsilon, gamma, and mu, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody.

The term "antigen" generally refers to a biological molecule, usually a protein, peptide, polysaccharide or conjugate in an immunogenic composition, or immunogenic substance that can stimulate the production of antibodies or T-cell responses, or both, in a subject, including compositions that are injected or absorbed into the subject. The immune response may be generated to the whole molecule, or to a various portions of the molecule (e.g., an epitope or hapten). The term may be used to refer to an individual molecule or to a homogeneous or heterogeneous population of antigenic molecules. An antigen is recognized by antibodies, T-cell receptors or other elements of specific humoral and/or cellular immunity. "Antigen" also includes all related antigenic epitopes. Epitopes of a given antigen can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715; each of which is incorporated herein by reference as if set forth in its entirety. Similarly, conformational epitopes may be identified by determining spatial conformation of amino acids such as by, e.g., x-ray crystallography and 2-dimensional nuclear magnetic resonance See, e.g., Epitope Mapping Protocols, supra. Furthermore, for purposes of the present invention, "antigen" also can be used to refer to a protein that includes modifications, such as deletions, additions and substitutions (generally conservative in nature, but they may be non-conservative), to the native sequence, as long as the protein maintains the ability to elicit an immunological response. These modifications may be deliberate, as through site-directed mutagenesis, or through particular synthetic procedures, or through a genetic engineering approach, or may be accidental, such as through mutations of hosts, which produce the antigens. Furthermore, the antigen can be derived, obtained, or isolated from a microbe, e.g., a bacterium, or can be a whole organism. Similarly, an oligonucleotide or polynucleotide, which expresses an antigen, such as in nucleic acid immunization applications, is also included in the definition. Synthetic antigens are also included, e.g., polyepitopes, flanking epitopes, and other recombinant or synthetically derived antigens (Bergmann et al. (1993) Eur. J. Immunol. 23:2777 2781; Bergmann et al. (1996) J. Immunol. 157:3242-3249; Suhrbier (1997) Immunol. Cell Biol. 75:402 408; Gardner et al. (1998) 12th World AIDS Conference, Geneva, Switzerland, Jun. 28 to Jul. 3, 1998).

A "protective" immune response refers to the ability of an immunogenic composition to elicit an immune response, either humoral or cell mediated, or both, which serves to protect a subject from an infection. The protection provided need not be absolute, i.e., the infection need not be totally prevented or eradicated, if there is a statistically significant improvement compared with a control population of subjects, e.g. infected animals not administered the vaccine or immunogenic composition. Protection may be limited to mitigating the severity or rapidity of onset of symptoms of the infection. In general, a "protective immune response" would include the induction of an increase in antibody levels specific for a particular antigen in at least 50% of subjects, including some level of measurable functional antibody responses to each antigen. In particular situations, a "protective immune response" could include the induction of a two fold increase in antibody levels or a fourfold increase in antibody levels specific for a particular antigen in at least 50% of subjects, including some level of measurable functional antibody responses to each antigen. In certain embodiments, opsonising antibodies correlate with a protective immune response. Thus, protective immune response may be assayed by measuring the percent decrease in the bacterial count in an opsonophagocytosis assay, for instance those described below. Preferably, there is a decrease in bacterial count of at least 10%, 25%, 50%, 65%, 75%, 80%, 85%, 90%, 95% or more.

The terms an "immunogenic amount," and an "immunologically effective amount," which are used interchangeably herein, refers to the amount of antigen or immunogenic composition sufficient to elicit an immune response, which may be a cellular (T-cell) or humoral (B-cell or antibody) response, or both, where such an immune response may be measured by standard assays known to one skilled in the art. Typically, an immunologically effective amount will elicit a protective immune response in a subject.

The immunogenic compositions of the present invention can be used to prophylactically or therapeutically, to protect or treat a subject susceptible to bacterial infection, e.g., by S. pneumonia or N. meningitidis or Group B Streptococcus or S. aureus or Enterococcus bacteria (such as Enterococcus faecalis or a Enterococcus faecium) bacteria, by means of administering the immunogenic compositions via a systemic, dermal or mucosal route, or can be used to generate a polyclonal or monoclonal antibody preparation that could be used to confer passive immunity on another subject. These administrations can include injection via the intramuscular, intraperitoneal, intradermal or subcutaneous routes; or via mucosal administration to the oral/alimentary, respiratory or genitourinary tracts. Immunogenic compositions may also be used to generate antibodies that are functional as measured by the killing of bacteria in either an animal efficacy model or via an opsonophagocytic killing assay.

Optimal amounts of components for a particular immunogenic composition can be ascertained by standard studies involving observation of appropriate immune responses in subjects. Following an initial vaccination, subjects can receive one or several booster immunizations adequately spaced.

In certain embodiments, the immunogenic composition will comprise one or more adjuvants. As defined herein, an "adjuvant" is a substance that serves to enhance the immunogenicity of an immunogenic composition of this invention. Thus, adjuvants are often given to boost the immune response and are well known to the skilled artisan. Suitable adjuvants to enhance effectiveness of the composition include, but are not limited to:

(1) aluminum salts (alum), such as aluminum hydroxide, aluminum phosphate, aluminum sulfate, etc.;
(2) oil-in-water emulsion formulations (with or without other specific immunostimulating agents such as muramyl peptides (defined below) or bacterial cell wall components), such as, for example,
   (a) MF59 (PCT Publ. No. WO 90/14837), containing 5% Squalene, 0.5% Tween 80, and 0.5% Span 85 (optionally containing various amounts of MTP-PE (see below, although not required)) formulated into submicron particles using a microfluidizer such as Model 110Y micro fluidizer (Microfluidics, Newton, Mass.),
   (b) SAF, containing 10% Squalene, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Corixa, Hamilton, Mont.) containing 2% Squalene, 0.2% Tween 80, and one or more bacterial cell wall components from the group consisting of 3-O-deacylated monophosphorylipid A (MPL™) described in U.S. Pat. No. 4,912,094 (Corixa), trehalose dimycolate (TDM), and cell wall skeleton (CWS), preferably MPL+ CWS (Detox™);

(3) saponin adjuvants, such as Quil A or STIMULON' QS-21 (Antigenics, Framingham. Mass.) (U.S. Pat. No. 5,057,540) may be used or particles generated therefrom such as ISCOMs (immunostimulating complexes);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-Tetradecanoyloxytetradecanoylamino]ethyl 2-Deoxy-4-O-phosphono-3-[(R)-3-tetradecanoyloxytetradecanoyl]-2-[(R)-3-tetradecanoyloxytetradecanoylamino]-b-D-glucopyranoside, which is also known as 529 (formerly known as RC529), which is formulated as an aqueous form or as a stable emulsion, synthetic polynucleotides such as oligonucleotides containing CpG motif(s) (U.S. Pat. No. 6,207,646);

(5) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2. etc.;

(6) detoxified mutants of a bacterial ADP-ribosylating toxin such as a cholera toxin (CT) either in a wild-type or mutant form, for example, where the glutamic acid at amino acid position 29 is replaced by another amino acid, preferably a histidine, in accordance with published international patent application number WO 00/18434 (see also WO 02/098368 and WO 02/098369), a pertussis toxin (PT), or an $E.$ $coli$ heat-labile toxin (LT), particularly LT-K63, LT-R72, CT-S109, PT-K9/G129 (see, e.g., WO 93/13302 and WO 92/19265); and (7) other substances that act as immunostimulating agents to enhance the effectiveness of the composition.

Muramyl peptides include, but are not limited to, N-acetylmuramyl-L-threonyl-D-isoglutamine (thr-MDP), N-acetylnormuramyl-L-alanine-2-(1'-2' dipalmitoyl-sn-glycero-3-hydroxyphosphoryloxy)-ethylamine (MTP-PE), etc.

In certain embodiments, the adjuvant is an aluminum-based adjuvant, such as an aluminum salt. In specific embodiments, the aluminum-based adjuvant is selected from the group consisting of aluminum phosphate, aluminum sulfate and aluminum hydroxide. In a specific embodiment, the adjuvant is aluminum phosphate.

The immunogenic composition optionally can comprise a pharmaceutically acceptable carrier. Pharmaceutically acceptable carriers include carriers approved by a regulatory agency of a Federal, a state government, or other regulatory agency, or listed in the U.S. Pharmacopeia or other generally recognized pharmacopeia for use in subjects, including humans as well as non-human mammals. The term carrier may be used to refer to a diluent, excipient, or vehicle with which the pharmaceutical composition is administered.

Water, saline solutions and aqueous dextrose and glycerol solutions can be employed as liquid carriers, particularly for injectable solutions. Examples of suitable pharmaceutical carriers are described in "Remington's Pharmaceutical Sciences" by E. W. Martin. The formulation should suit the mode of administration.

The immunogenic compositions of the invention may further comprise one or more preservatives in addition to a plurality of capsular polysaccharide-protein conjugates. The FDA requires that biological products in multiple-dose (multi-dose) vials contain a preservative, with only a few exceptions. Vaccine products containing preservatives include vaccines containing benzethonium chloride (anthrax), 2-phenoxyethanol (DTaP, HepA, Lyme, Polio (parenteral)), phenol (Pneumo, Typhoid (parenteral), Vaccinia) and thimerosal (DTaP, DT, Td, HepB, Hib, Influenza, JE, Mening, Pneumo, Rabies). Preservatives approved for use in injectable drugs include, e.g., chlorobutanol, m-cresol, methylparaben, propylparaben, 2-phenoxyethanol, benzethonium chloride, benzalkonium chloride, benzoic acid, benzyl alcohol, phenol, thimerosal and phenylmercuric nitrate.

In certain embodiments, a formulation of the invention which is compatible with parenteral administration comprises one or more non-ionic surfactants, including but not limited to polyoxyethylene sorbitan fatty acid esters, Polysorbate-80 (Tween 80), Polysorbate-60 (Tween 60), Polysorbate-40 (Tween 40) and Polysorbate-20 (Tween 20), polyoxyethylene alkyl ethers, including but not limited to Brij 58, Brij 35, as well as others such as Triton X-100; Triton X-114, NP40, Span 85 and the Pluronic series of non-ionic surfactants (e.g., Pluronic 121), with preferred components Polysorbate-80 at a concentration from about 0.001% to about 2% (with up to about 0.25% being preferred) or Polysorbate-40 at a concentration from about 0.001% to 1% (with up to about 0.5% being preferred).

Packaging and Dosing Forms

Direct delivery of immunogenic compositions of the present invention to a subject may be accomplished by parenteral administration (intramuscularly, intraperitoneally, intradermally, subcutaneously, intravenously, or to the interstitial space of a tissue); or via mucosal administration to the oral/alimentary, respiratory or genitourinary tracts; or by topical, transdermal, intranasal, ocular, aural, pulmonary or other mucosal administration.

In one embodiment, parenteral administration is by intramuscular injection, e.g., to the thigh or upper arm of the subject. Injection may be via a needle (e.g. a hypodermic needle), but needle free injection may alternatively be used. A typical intramuscular dose is 0.5 mL. In another embodiment, intranasal administration is used for the treatment of pneumonia or otitis media (as nasopharyngeal carriage of pneumococci can be more effectively prevented, thus attenuating infection at its earliest stage).

Compositions of the invention may be prepared in various forms, e.g., for injection either as liquid solutions or suspensions. In certain embodiments, the composition may be prepared as a powder or spray for pulmonary administration, e.g. in an inhaler. In other embodiments, the composition may be prepared as a suppository or pessary, or for nasal, aural or ocular administration, e.g., as a spray, drops, gel or powder.

The amount of glycoconjugate in each immunogenic composition dose is selected as an amount that induces an immunoprotective response without significant, adverse effects. Such amount can vary depending upon the bacterial serotype present in the glycoconjugate. Generally, each dose will comprise 0.1 to 100 µg of polysaccharide, particularly 0.1 to 10 µg, and more particularly 1 to 5 µg.

In a particular embodiment of the present invention, the immunogenic composition is a sterile liquid formulation of a Pn or Mn capsular polysaccharide individually conjugated to $CRM_{197}$ via an oxo-eT linker, wherein each 0.5 mL dose is formulated to contain 1-5 µg of polysaccharide, which may further contain 0.125 mg of elemental aluminum (0.5 mg aluminum phosphate) adjuvant; and sodium chloride and sodium succinate buffer as excipients.

Optimal amounts of components for a particular immunogenic composition may be ascertained by standard studies involving observation of appropriate immune responses in subjects. Following an initial vaccination, subjects can receive one or several booster immunizations adequately spaced.

Immunogenic compositions of the invention may be packaged in unit dose or multi-dose form (e.g., 2 doses, 4 doses, or more). For multi-dose forms, vials are typically but not necessarily preferred over pre-filled syringes. Suitable multi-dose formats include but are not limited to: 2 to 10 doses per container at 0.1 to 2 mL per dose. In certain embodiments, the dose is a 0.5 mL dose. See, e.g., International Patent Application WO 2007/127668, which is incorporated by reference herein.

Compositions may be presented in vials or other suitable storage containers, or may be presented in pre-filled delivery devices, e.g., single or multiple component syringes, which may be supplied with or without needles. A syringe typically but need not necessarily contains a single dose of the preservative-containing immunogenic composition of the invention, although multi-dose, pre-filled syringes are also envisioned. Likewise, a vial may include a single dose but may alternatively include multiple doses.

Effective dosage volumes can be routinely established, but a typical dose of the composition for injection has a volume of 0.5 mL. In certain embodiments, the dose is formulated for administration to a human subject. In certain embodiments, the dose is formulated for administration to an adult, teen, adolescent, toddler or infant (i.e., no more than one year old) human subject and may in preferred embodiments be administered by injection.

Liquid immunogenic compositions of the invention are also suitable for reconstituting other immunogenic compositions which are presented in lyophilized form. Where an immunogenic composition is to be used for such extemporaneous reconstitution, the invention provides a kit with two or more vials, two or more ready-filled syringes, or one or more of each, with the contents of the syringe being used to reconstitute the contents of the vial prior to injection, or vice versa.

In yet another embodiment, a container of the multi-dose format is selected from one or more of the group consisting of, but not limited to, general laboratory glassware, flasks, beakers, graduated cylinders, fermentors, bioreactors, tubings, pipes, bags, jars, vials, vial closures (e.g., a rubber stopper, a screw on cap), ampoules, syringes, dual or multi-chamber syringes, syringe stoppers, syringe plungers, rubber closures, plastic closures, glass closures, cartridges and disposable pens and the like. The container of the present invention is not limited by material of manufacture, and includes materials such as glass, metals (e.g., steel, stainless steel, aluminum, etc.) and polymers (e.g., thermoplastics, elastomers, thermoplastic-elastomers). In a particular embodiment, the container of the format is a 5 mL Schott Type 1 glass vial with a butyl stopper. The skilled artisan will appreciate that the format set forth above is by no means an exhaustive list, but merely serve as guidance to the artisan with respect to the variety of formats available for the present invention. Additional formats contemplated for use in the present invention may be found in published catalogues from laboratory equipment vendors and manufacturers such as United States Plastic Corp. (Lima, Ohio), VWR.

Methods for Inducing an Immune Response and Protecting Against Infection

The present invention also includes methods for using oxo-eT linked glycoconjugates and immunogenic compositions comprising them, either prophylactically or therapeutically. For example, one aspect of the invention provides a method of inducing an immune response against a pathogenic bacteria, for example pneumococcal or meningococcal bacteria, comprising administering to a subject an immunologically effective amount of any of the immunogenic compositions described herein comprising a bacterial antigen, such as a bacterial capsular polysaccharide derived from pathogenic bacteria. One embodiment of the invention provides a method of protecting a subject against an infection by pathogenic bacteria, or a method of preventing, treating or ameliorating an infection disease or condition associated with a pathogenic bacteria, or a method of reducing the severity of or delaying the onset of at least one symptom associated with an infection caused by pathogenic bacteria, in each case the methods comprising administering to a subject an immunologically effective amount of any of the immunogenic compositions described herein comprising a bacterial antigen, such as a bacterial capsular polysaccharide derived from the pathogenic bacteria.

One embodiment of the invention provides a method of preventing, treating or ameliorating a bacterial infection, disease or condition in a subject, comprising administering to the subject an immunologically effective amount of an immunogenic composition of the invention, wherein said immunogenic composition comprises an oxo-eT linked glycoconjugate comprising a bacterial antigen, such as a bacterial capsular polysaccharide.

In some embodiments, the method of preventing, treating or ameliorating a bacterial infection, disease or condition comprises human, veterinary, animal, or agricultural treatment. Another embodiment provides a method of preventing, treating or ameliorating a bacterial infection, disease or condition associated with pathogenic bacteria in a subject, the method comprising generating a polyclonal or monoclonal antibody preparation from the immunogenic composition described herein, and using said antibody preparation to confer passive immunity to the subject. One embodiment of the invention provides a method of preventing a bacterial infection in a subject undergoing a surgical procedure, the method comprising the step of administering a prophylactically effective amount of an immunogenic composition described herein to the subject prior to the surgical procedure.

In preferred embodiments of each of the foregoing methods, the pathogenic bacteria are pneumococcal or meningococcal bacteria, such as *S. pneumoniae* or *N. meningitis* bacteria. In some such embodiments, the bacterial antigen is a capsular polysaccharide selected from the group consisting of Pn-serotype 1, 3, 4, 5, 6A, 6B, 7F, 8, 9V, 10A, 11A, 12F, 14, 15B, 18C, 19A, 19F, 22F, 23F and 33F capsular polysaccharides. In other such embodiments, the bacterial antigen is a capsular polysaccharide selected from the group consisting of Mn-serotype A, C, W135 and Y capsular polysaccharides. In other such embodiments, the bacterial antigen is a capsular polysaccharide selected from the group consisting of GBS-serotype Ia, Ib, II, III and V capsular polysaccharides. In other such embodiments, the capsular polysaccharide is a capsular polysaccharide from *Staphylococcus aureus* (e.g. *S. aureus* serotype 5 or 8 capsular polysaccharide) or a capsular polysaccharide from an *Enterococcus* bacteria (such as *Enterococcus faecalis* or *Enterococcus faecium* capsular polysaccharide).

An immune response to an antigen or immunogenic composition is characterized by the development in a subject of a humoral and/or a cell-mediated immune response to molecules present in the antigen or immunogenic composition of interest. For purposes of the present invention, a "humoral immune response" is an antibody-mediated immune response and involves the induction and generation of antibodies that recognize and bind with some affinity for the antigen in the immunogenic composition of the invention, while a "cell-mediated immune response" is one mediated by T-cells and/or other white blood cells. A "cell-mediated immune response" is elicited by the presentation of antigenic epitopes in association with Class I or Class II molecules of the major histocompatibility complex (MHC), CD1 or other non-classical MHC-like molecules. This activates antigen-specific CD4+ T helper cells or CD8+ cytotoxic T lymphocyte cells ("CTLs"). CTLs have specificity for peptide antigens that are presented in association with proteins encoded by classical or non-classical MHCs and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide or other antigens in association with classical or non-classical MHC molecules on their surface. A "cell-mediated immune response" also refers to the production of cytokines, chemokines and other such molecules produced by activated T-cells and/or other white blood cells, including those derived from CD4+ and CD8+ T-cells. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to re-stimulation with antigen. Such assays are well known in the art. See, e.g., Erickson et al. (1993) *J. Immunol.* 151:4189-4199; and Doe et al. (1994) *Eur. J. Immunol.* 24:2369-2376.

The immunogenic compositions and methods of the invention may be useful for one or more of the following: (i) the prevention of infection or re-infection, as in a traditional vaccine, (ii) the reduction in the severity of, or, in the elimination of symptoms, and/or (iii) the substantial or complete elimination of the pathogen or disorder in question. Hence, treatment may be effected prophylactically (prior to infection) or therapeutically (following infection). In the present invention, prophylactic treatment is the preferred mode. According to a particular embodiment of the present invention, compositions and methods are provided that treat, including prophylactically and/or therapeutically immunize, a host subject against bacterial infection, e.g., by *S. pneumoniae* or *N. meningitidis*, GBS or *S. aureus* or *Enterococcus* bacteria (such as *Enterococcus faecalis* or a *Enterococcus faecium*. The methods of the present invention are useful for conferring prophylactic and/or therapeutic immunity to a subject. The methods of the present invention can also be practiced on subjects for biomedical research applications.

As used herein, the term "subject" means a human or non-human animal. More particularly, subject refers to any animal classified as a mammal, including humans, domestic and farm animals, and research, zoo, sports and pet companion animals such as a household pet and other domesticated animals including, but not limited to, cattle, sheep, ferrets, swine, horses, rabbits, goats, dogs, cats, and the like. Preferred companion animals are dogs and cats. Preferably, the subject is human.

The amount of a particular conjugate in a composition is generally calculated based on total amount of polysaccharide, both conjugated and non-conjugated for that conjugate. For example, a conjugate with 20% free polysaccharide will have about 80 µg of conjugated polysaccharide and about 20 µg of non-conjugated polysaccharide in a 100 µg polysaccharide dose. The protein contribution to the conjugate is usually not considered when calculating the dose of a conjugate. The immunogenic amount of a conjugate or immunogenic composition may vary depending upon the bacterial serotype. Generally, each dose will comprise 0.1 to 100 µg of polysaccharide, particularly 0.1 to 10 µg, and more particularly 1 to 10 µg. The immunogenic amount of the different polysaccharide components in an immunogenic composition may diverge and each may comprise 1 µg, 2 µg, 3 µg, 4 µg, 5 µg, 6 µg, 7 µg, 8 µg, 9 µg, 10 µg, 15 µg, 20 µg, 30 µg, 40 µg, 50 µg, 60 µg, 70 µg, 80 µg, 90 µg, or about 100 µg of any particular polysaccharide antigen.

The term "invasive disease" refers to the isolation of bacteria from a normally sterile site, where there are associated clinical signs/symptoms of disease. Normally sterile body sites include blood, CSF, pleural fluid, pericardial fluid, peritoneal fluid, joint/synovial fluid, bone, internal body site (lymph node, brain, heart, liver, spleen, vitreous fluid, kidney, pancreas, ovary) or other normally sterile sites. Clinical conditions characterizing invasive diseases include bacteremia, pneumonia, cellulitis, osteomyelitis, endocarditis, septic shock and more.

The effectiveness of an antigen as an immunogen can be measured either by proliferation assays, by cytolytic assays, such as chromium release assays to measure the ability of a T-cell to lyse its specific target cell, or by measuring the levels of B-cell activity by measuring the levels of circulating antibodies specific for the antigen in serum. An immune response may also be detected by measuring the serum levels of antigen specific antibody induced following administration of the antigen, and more specifically, by measuring the ability of the antibodies so induced to enhance the opsonophagocytic ability of particular white blood cells, as described herein. The level of protection of the immune response may be measured by challenging the immunized host with the antigen that has been administered. For example, if the antigen to which an immune response is desired is a bacterium, the level of protection induced by the immunogenic amount of the antigen is measured by detecting the percent survival or the percent mortality after challenge of the animals with the bacterial cells. In one embodiment, the amount of protection may be measured by measuring at least one symptom associated with the bacterial infection, e.g., a fever associated with the infection. The amount of each of the antigens in the multi-antigen or multi-component vaccine or immunogenic compositions will vary with respect to each of the other components and can be determined by methods known to the skilled artisan.

Such methods would include procedures for measuring immunogenicity and/or in vivo efficacy.

In another aspect, the invention provides antibodies and antibody compositions which bind specifically and selectively to the capsular polysaccharides or glycoconjugates of the present invention. In some such embodiments, the invention provides antibodies and antibody compositions which bind specifically and selectively to the Pn-serotype 1, 3, 4, 5, 6A, 6B, 7F, 8, 9V, 10A, 11A, 12F, 14, 15B, 18C, 19A, 19F, 22F, 23F or 33F capsular polysaccharides or glycoconjugates comprising them. In other such embodiments, the invention provides antibodies and antibody compositions which bind specifically and selectively to the Mn-serotype A, C, W135 or Y capsular polysaccharides or glycoconjugates comprising them. In other such embodiments, the invention provides antibodies and antibody compositions which bind specifically and selectively to the GBS-serotype Ia, Ib, II, III and V capsular polysaccharides or glycoconjugates comprising them. In other such embodiments, the invention provides antibodies and antibody compositions which bind specifically and selectively to the *S. aureus* serotype 5 or 8 capsular polysaccharide or *Enterococcus faecalis* or *Enterococcus faecium* capsular polysaccharides or glycoconjugates comprising them. In some embodiments, antibodies are generated upon administration to a subject of the capsular polysaccharides or glycoconjugates of the present invention. In some embodiments, the invention provides purified or isolated antibodies directed against one or more of the capsular polysaccharides or glycoconjugates of the present invention. In some embodiments, the antibodies of the present invention are functional as measured by killing bacteria in either an animal efficacy model or via an opsonophagocytic killing assay. Antibodies or antibody compositions of the invention may be used in a method of treating or preventing a bacterial infection, disease or condition associated with pathogenic bacteria in a subject, e.g., *S. pneumoniae* or *N. meningitidis* or Group B Streptoccus or *S. aureus* or *Enterococcus* bacteria, the method comprising generating a polyclonal or monoclonal antibody preparation, and using said antibody or antibody composition to confer passive immunity to the subject. Antibodies of the invention may also be useful for diagnostic methods, e.g., detecting the presence of or quantifying the levels of capsular polysaccharide or a glycoconjugate thereof. For example, antibodies of the invention may also be useful for detecting the presence of or quantifying the levels of a Pn or Mn or GBS or *S. aureus* or *Enterococcus* capsular polysaccharide or a glycoconjugate thereof, wherein the glycoconjugate comprises the bacterial capsular polysaccharide conjugated to a carrier protein through an oxo-eT spacer.

Several assays and animal models known in the art may be used to assess the efficacy of any one of the immunogenic compositions described herein. For example, Chiavolini et al. *Clin. Microbiol. Rev.* (2008), 21(4):666-685) describe animal models of *S. pneumoniae* diseases. Gorringe et al. METHODS IN MOLECULAR MEDICINE, vol. 66 (2001), Chapter 17, Pollard and Maiden eds. (Humana Press Inc.) describe animal models for meningococcal diseases.

Opsonophagocytic Activity (OPA) Assay

OPA assay procedures were based on the methods previously described by Hu, et al. (*Clin. Diagn. Lab. Immunol.* 2005; 12(2):287-95), with the following modifications. Heat-inactivated sera were serially diluted 2.5-fold in buffer. Target bacteria were added to assay plates and were incubated for 30 min at 25° C. on a shaker. Baby rabbit complement (3- to 4-weekold, Pel-Freez, 12.5% final concentration) and differentiated HL-60 cells, were then added to each well at an approximate effector to target ratio of 200:1. Assay plates were incubated for 45 min at 37° C. on a shaker. To terminate the reaction, 80 µL of 0.9% NaCl was added to all wells, mixed, and a 10-4 aliquot were transferred to the wells of Millipore, MultiScreenHTS HV filter plates containing 200 µL of water. Liquid was filtered through the plates under vacuum, and 150 µL of HySoy medium was added to each well and filtered through. The filter plates were then incubated at 37° C., 5% $CO_2$ overnight and were then fixed with Destain Solution (Bio-Rad). The plates were then stained with Coomassie Blue and destained once. Colonies were imaged and enumerated on a Cellular Technology Limited (CTL) ImmunoSpot Analyzer®. The OPA antibody titer was interpolated from the reciprocal of the two serum dilutions encompassing the point of 50% reduction in the number of bacterial colonies when compared to the control wells that did not contain immune serum.

Particular Embodiments of the Invention are Set Forth in the Following Numbered Paragraphs:

1. A glycoconjugate comprising a saccharide covalently conjugated to a carrier protein through a spacer containing ((2-oxoethyl)thio).

2. The glycoconjugate of paragraph 1 having the general formula (I):

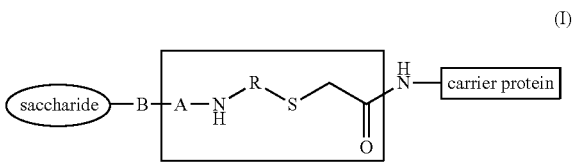

wherein:

A is a group (C=X)m wherein X is S or O and m is 0 or 1;
B is a bond, O, or $CH_2$; and when m is 0, B can also be (C=O);
R is a $C_2$-$C_{16}$ alkylene, $C_2$-$C_{16}$ heteroalkylene, NH—C(=O)—$C_2$-$C_{16}$ alkylene, or NH—C(=O)—$C_2$-$C_{16}$ heteroalkylene, wherein said alkylene and heteroalkylene are optionally substituted by 1, 2 or 3 groups independently selected from COOR' where R' is selected from H, methyl, ethyl or propyl.

3. The glycoconjugate of paragraph 2 wherein X is O and m is 1.

4. The glycoconjugate of paragraph 2 wherein X is S and m is 1.

5. The glycoconjugate of paragraph 2 wherein m is 0.

6. The glycoconjugate of anyone of paragraphs 2 to 5 wherein B is a bond.

7. The glycoconjugate of anyone of paragraphs 2 to 5 wherein B is O.

8. The glycoconjugate of anyone of paragraphs 2 to 5 wherein B is $CH_2$.

9. The glycoconjugate of paragraph 2 wherein m is 0 and B is (C=O).

10. The glycoconjugate of anyone of paragraphs 2 to 9 wherein R is selected from the groups consisting of $(CH_2)_2$, $(CH_2)_3$, $(CH_2)_4$, $(CH_2)_5$, $(CH_2)_6$, $(CH_2)_7$, $(CH_2)_8$, $(CH_2)_9$ or $(CH_2)_{10}$.

11. The glycoconjugate of anyone of paragraphs 2 to 9 wherein R is a $C_2$-$C_{16}$ heteroalkylene.

12. The glycoconjugate of anyone of paragraphs 2 to 9 wherein R is selected from the groups consisting of O—$CH_2$, O—$CH_2$—$CH_2$, $CH_2$—$CH_2$—O—$CH_2$—$CH_2$, O—CH₂—CH₂—O—CH₂—CH₂, O—CH₂—CH₂—O—CH₂—CH₂—O—CH₂—CH₂, O—CH₂—CH₂—(N—CH₃)—CH₂—CH₂—O—CH₂—CH₂, CH₂—CH₂—(N—CH₃)—CH₂—CH₂ and CH₂—CH₂—S—CH₂—CH₂.

13. The glycoconjugate of anyone of paragraphs 1 to 12 with the provisio that said spacer is not the (2-((2-oxoethyl)thio)ethyl)carbamate (eTEC) spacer.

14. The glycoconjugate of paragraph 1 having the general formula (II):

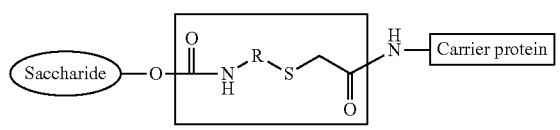

(II)

wherein R is $(CH_2)_n$ where n is 3 to 10.

15. The glycoconjugate of paragraph 14 wherein n is 3.
16. The glycoconjugate of paragraph 14 wherein n is 4.
17. The glycoconjugate of paragraph 14 wherein n is 5.
18. The glycoconjugate of paragraph 14 wherein n is 6.
19. The glycoconjugate of paragraph 1 having the general formula (III):

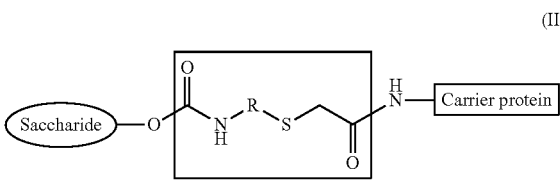

(III)

wherein R is selected from $(CH_2CH_2O)_m CH_2CH_2$, $CH(COOH)(CH_2)_n$, $NHCO(CH_2)_n$, $NHCO(CH_2CH_2O)_m CH_2CH_2$, $OCH_2(CH_2)_n$ or $O(CH_2CH_2O)_m CH_2CH_2$;
wherein n is selected from 1 to 10 and m is selected from 1 to 4.

20. The glycoconjugate of paragraph 19 wherein R is $CH(COOH)(CH_2)_n$ and wherein n is selected from 1 to 10.
21. The glycoconjugate of paragraph 19 wherein R is $NHCO(CH_2)_n$ and wherein n is selected from 1 to 10.
22. The glycoconjugate of paragraph 19 wherein R is $OCH_2(CH_2)_n$ and wherein n is selected from 1 to 10.
23. The glycoconjugate of paragraph 19 wherein R is $(CH_2CH_2O)_m CH_2CH_2$ and wherein m is selected from 1 to 4.
24. The glycoconjugate of paragraph 19 wherein R is $NHCO(CH_2CH_2O)_m CH_2CH_2$ and wherein m is selected from 1 to 4.
25. The glycoconjugate of paragraph 19 wherein R is $O(CH_2CH_2O)_m CH_2CH_2$ and wherein m is selected from 1 to 4.
26. The glycoconjugate of anyone of paragraphs 19 to 22 wherein n is 1 to 5.
27. The glycoconjugate of anyone of paragraphs 19 to 22 wherein n is 1 to 4.
28. The glycoconjugate of anyone of paragraphs 19 to 22 wherein n is 1 to 3.
29. The glycoconjugate of anyone of paragraphs 19 to 22 wherein n is 1 or 2.
30. The glycoconjugate of anyone of paragraphs 19 or 23 to 25 wherein m is 1 to 3.
31. The glycoconjugate of anyone of paragraphs 19 or 23 to 25 wherein m is 1 or 2.
32. The glycoconjugate of anyone of paragraphs 19 or 23 to 25 wherein m is 1.
33. The glycoconjugate of paragraph 1 having the general formula (IV):

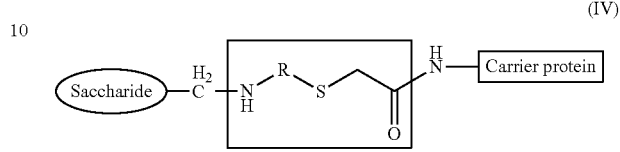

(IV)

wherein R is selected from $CH_2(CH_2)_n$, $(CH_2CH_2O)_m CH_2CH_2$, $CH(COOH)(CH_2)_n$, $NHCO(CH_2)_n$, $NHCO(CH_2CH_2O)_m CH_2CH_2$, $OCH_2(CH_2)_n$ or $O(CH_2CH_2O)_m CH_2CH_2$;
wherein n is selected from 1 to 10 and m is selected from 1 to 4.

34. The glycoconjugate of paragraph 33 wherein R is $CH_2(CH_2)_n$ and wherein n is selected from 1 to 10.
35. The glycoconjugate of paragraph 33 wherein R is $CH(COOH)(CH_2)_n$ and wherein n is selected from 1 to 10.
36. The glycoconjugate of paragraph 33 wherein R is $NHCO(CH_2)_n$ and wherein n is selected from 1 to 10.
37. The glycoconjugate of paragraph 33 wherein R is $OCH_2(CH_2)_n$ and wherein n is selected from 1 to 10.
38. The glycoconjugate of paragraph 33 wherein R is $(CH_2CH_2O)_m CH_2CH_2$ and wherein m is selected from 1 to 4.
39. The glycoconjugate of paragraph 33 wherein R is $NHCO(CH_2CH_2O)_m CH_2CH_2$ and wherein m is selected from 1 to 4.
40. The glycoconjugate of paragraph 33 wherein R is $O(CH_2CH_2O)_m CH_2CH_2$ and wherein m is selected from 1 to 4.
41. The glycoconjugate of anyone of paragraphs 33 to 37 wherein n is 1 to 5.
42. The glycoconjugate of anyone of paragraphs 33 to 37 wherein n is 1 to 4.
43. The glycoconjugate of anyone of paragraphs 33 to 37 wherein n is 1 to 3.
44. The glycoconjugate of anyone of paragraphs 33 to 37 wherein n is 1 or 2.
45. The glycoconjugate of anyone of paragraphs 33 or 38 to 40 wherein m is 1 to 3.
46. The glycoconjugate of anyone of paragraphs 33 or 38 to 40 wherein m is 1 or 2.
47. The glycoconjugate of anyone of paragraphs 33 or 38 to 40 wherein m is 1.
48. The glycoconjugate of paragraph 1 having the general formula (V):

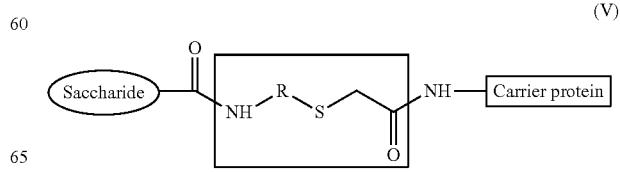

(V)

wherein R is selected from $CH_2(CH_2)_1$, $(CH_2CH_2O)_mCH_2CH_2$, $CH(COOH)(CH_2)_1$, $NHCO(CH_2)_1$, $NHCO(CH_2CH_2O)_mCH_2CH_2$, $OCH_2(CH_2)_n$ or $O(CH_2CH_2O)_mCH_2CH_2$;

wherein n is selected from 1 to 10 and m is selected from 1 to 4.

49. The glycoconjugate of paragraph 48 wherein R is $CH_2(CH_2)_n$ and wherein n is selected from 1 to 10.

50. The glycoconjugate of paragraph 48 wherein R is $CH(COOH)(CH2)_n$ and wherein n is selected from 1 to 10.

51. The glycoconjugate of paragraph 48 wherein R is $NHCO(CH2)_n$ and wherein n is selected from 1 to 10.

52. The glycoconjugate of paragraph 48 wherein R is $OCH_2(CH_2)n$ and wherein n is selected from 1 to 10.

53. The glycoconjugate of paragraph 48 wherein R is $(CH_2CH_2O)_mCH_2CH_2$ and wherein m is selected from 1 to 4.

54. The glycoconjugate of paragraph 48 wherein R is $NHCO(CH_2CH_2O)_mCH2CH2$ and wherein m is selected from 1 to 4.

55. The glycoconjugate of paragraph 48 wherein R is $O(CH_2CH_2O)_mCH_2CH_2$ and wherein m is selected from 1 to 4.

56. The glycoconjugate of anyone of paragraphs 48 to 52 wherein n is 1 to 5.

57. The glycoconjugate of anyone of paragraphs 48 to 52 wherein n is 1 to 4.

58. The glycoconjugate of anyone of paragraphs 48 to 52 wherein n is 1 to 3.

59. The glycoconjugate of anyone of paragraphs 48 to 52 wherein n is 1 or 2.

60. The glycoconjugate of anyone of paragraphs 48 or 53 to 55 wherein m is 1 to 3.

61. The glycoconjugate of anyone of paragraphs 48 or 53 to 55 wherein m is 1 or 2.

62. The glycoconjugate of anyone of paragraphs 48 or 53 to 55 wherein m is 1.

63. The glycoconjugate of paragraph 1 comprising a saccharide conjugated to a carrier protein through an oxo-eTAC spacer, wherein the saccharide is covalently linked to the oxo-eTAC spacer through a carbamate linkage, and wherein the carrier protein is covalently linked to the oxo-eTAC spacer through a thioether and amide linkage.

64. The glycoconjugate of paragraph 1 comprising a saccharide conjugated to a carrier protein through an oxo-eTAAN spacer, wherein the saccharide is covalently linked to the oxo-eTAAN spacer through an amine linkage, and wherein the carrier protein is covalently linked to the oxo-eTAAN spacer through a thioether and amide linkage.

65. The glycoconjugate of paragraph 1 comprising a saccharide conjugated to a carrier protein through an oxo-eTAAD spacer, wherein the saccharide is covalently linked to the oxo-eTAAD spacer through an amide linkage, and wherein the carrier protein is covalently linked to the oxo-eTAAD spacer through a thioether and amide linkage.

66. The glycoconjugate of anyone of paragraphs 1 to 65, wherein the saccharide is a polysaccharide or an oligosaccharide.

67. The glycoconjugate of anyone of paragraphs 1 to 65, wherein the saccharide is a capsular polysaccharide derived from bacteria.

68. The glycoconjugate of paragraph 67, wherein said capsular polysaccharide is derived from S. pneumoniae.

69. The glycoconjugate of paragraph 68, wherein said capsular polysaccharide is selected from the group consisting of Pn-serotype 1, 2, 3, 4, 5, 6A, 6B, 7F, 8, 9V, 9N, 10A, 11A, 12F, 14, 15A, 15B, 17F, 18C, 19A, 19F, 20, 22F, 23A, 23B, 23F, 33F and 35B capsular polysaccharides.

70. The glycoconjugate of paragraph 68, wherein said capsular polysaccharide is selected from the group consisting of Pn-serotype 2, 9N, 15A, 17F, 20, 23A, 23B, and 35B capsular polysaccharides.

71. The glycoconjugate of paragraph 68, wherein said capsular polysaccharide is selected from the group consisting of Pn-serotype 1, 3, 4, 5, 8, 9V, 9N, 12F and 22F.

72. The glycoconjugate of paragraph 68, wherein said capsular polysaccharide is a Pn-serotype 33F capsular polysaccharide.

73. The glycoconjugate of paragraph 68, wherein said capsular polysaccharide is a Pn-serotype 22F capsular polysaccharide.

74. The glycoconjugate of paragraph 68, wherein said capsular polysaccharide is a Pn-serotype 10A capsular polysaccharide.

75. The glycoconjugate of paragraph 68, wherein said capsular polysaccharide is a Pn-serotype 11A capsular polysaccharide.

76. The glycoconjugate of anyone of paragraphs 1 to 65, wherein the saccharide is a capsular saccharide derived from N. meningitidis.

77. The glycoconjugate of paragraph 75, wherein the saccharide is a polysaccharide.

78. The glycoconjugate of paragraph 75, wherein the saccharide is an oligosaccharide.

79. The glycoconjugate of paragraphs 75 to 78, wherein the capsular saccharide is selected from the group consisting of Mn-serotype A, C, W135 and Y capsular saccharides, preferably from the group consisting of Mn-serotype C, W135 and Y capsular saccharides.

80. The glycoconjugate of paragraphs 75 to 78, wherein the capsular saccharide is of Mn-serotype X capsular saccharide 81. The glycoconjugate of paragraph 67, wherein said capsular polysaccharide is derived from Group B *Streptococcus*.

82. The glycoconjugate of paragraph 81, wherein said Group B *Streptococcus* capsular polysaccharide is selected from the group consisting of serotype Ia, Ib, II, III or V capsular polysaccharides 83. The glycoconjugate of paragraph 67, wherein said capsular polysaccharide is derived from *Staphylococcus aureus*.

84. The glycoconjugate of paragraph 83, wherein said *S. aureus* capsular polysaccharide is *S. aureus* serotype 5 or 8 capsular polysaccharide.

85. The glycoconjugate of paragraph 67, wherein said capsular polysaccharide is derived from an *Enterococcus* bacteria.

86. The glycoconjugate of paragraph 85, wherein said *Enterococcus* capsular polysaccharide is *Enterococcus faecalis* or *Enterococcus faecium* capsular polysaccharide.

87. The glycoconjugate of paragraph 67, wherein said capsular polysaccharide is derived from a sialic acid and/or uronic acid containing bacterial polysaccharide.

88. The glycoconjugate of any one of paragraphs 1 to 87, wherein the saccharide has a molecular weight of between 10 kDa and 2,000 kDa.

89. The glycoconjugate of paragraph 88, wherein the polysaccharide has a molecular weight of between 50 kDa and 2,000 kDa.

90. The glycoconjugate of any one of paragraphs 1 to 89, wherein the glycoconjugate has a molecular weight of between 50 kDa and 20,000 kDa.

91. The glycoconjugate of paragraph 90, wherein the glycoconjugate has a molecular weight of between 500 kDa and 10,000 kDa.

92. The glycoconjugate of any one of paragraphs 1 to 91, wherein the polysaccharide has a degree of 0-acetylation between 75-100%.

93. The glycoconjugate of any one of paragraphs 1 to 92, wherein the carrier protein is selected in the group consisting of TT, DT, DT mutants (such as $CRM_{197}$), *H. influenzae* protein D, PhtX, PhtD, PhtDE fusions, detoxified pneumolysin, PorB, N19 protein, PspA, OMPC, toxin A or B of *C. Difficile* and PsaA.

94. The glycoconjugate of any one of paragraphs 1 to 92, wherein the carrier protein is selected in the group consisting of TT, DT, $CRM_{197}$ and *H. influenzae* protein D.

95. The glycoconjugate of any one of paragraphs 1 to 92, wherein the carrier protein is $CRM_{197}$.

96. The glycoconjugate of paragraph 95, wherein the $CRM_{197}$ comprises 2 to 20 lysine residues covalently linked to the polysaccharide through an oxo-eT spacer.

97. The glycoconjugate of paragraph 95, wherein the $CRM_{197}$ comprises 4 to 16 lysine residues covalently linked to the polysaccharide through an oxo-eT spacer.

98. The glycoconjugate of any one of paragraphs 1 to 97, wherein the saccharide:carrier protein ratio (w/w) is between 0.2 and 4.

99. The glycoconjugate of paragraph 98, wherein the saccharide:carrier protein ratio (w/w) is between 0.4 and 1.7.

100. The glycoconjugate of any one of paragraphs 1 to 99, wherein at least one linkage between the carrier protein and saccharide occurs at every 25 saccharide repeat units of the saccharide.

101. The glycoconjugate of paragraph 100, wherein at least one linkage between the carrier protein and saccharide occurs at every 15 saccharide repeat units of the saccharide.

102. The glycoconjugate of paragraph 100, wherein at least one linkage between the carrier protein and saccharide occurs at every 10 saccharide repeat units of the saccharide.

103. The glycoconjugate of paragraph 100, wherein at least one linkage between the carrier protein and saccharide occurs at every 4 saccharide repeat units of the saccharide.

104. The glycoconjugate of any one of paragraphs 98 to 103, wherein said carrier protein is $CRM_{197}$.

105. The glycoconjugate of any one of paragraphs 1 to 104, which comprises less than 15% free saccharide compared to the total amount of saccharide.

106. The glycoconjugate of any one of paragraphs 1 to 105, having a molecular size distribution (Kd) of ≥35% at ≤0.3.

107. An immunogenic composition comprising at least one glycoconjugate as defined in anyone of paragraphs 1 to 106.

108. An immunogenic composition comprising at least one glycoconjugate as defined in anyone of paragraphs 1 to 106 and a pharmaceutically acceptable excipient, carrier or diluents 109. The immunogenic composition of paragraph 107 or 108, further comprising an additional antigen.

110. The immunogenic composition of paragraph 109, wherein the additional antigen comprises a protein antigen or a glycoconjugate of a capsular polysaccharide derived from *S. pneumonia*.

111. The immunogenic composition of paragraph 110, wherein the additional antigen comprises a glycoconjugate of a capsular polysaccharide selected from the group consisting of Pn-serotype 1, 3, 4, 5, 6A, 6B, 7F, 8, 9V, 10A, 11A, 12F, 14, 15B, 18C, 19A, 19F, 22F, 23F and 33F capsular polysaccharides.

112. The immunogenic composition of paragraph 109, wherein the additional antigen comprises a protein antigen or a glycoconjugate of a capsular polysaccharide derived from *N. meningitidis*.

113. The immunogenic composition of paragraph 109, wherein the additional antigen comprises a glycoconjugate of a capsular polysaccharide selected from the group consisting of serotype A, C, W135 and Y capsular polysaccharides.

114. The immunogenic composition of any one of paragraphs 107 to 113, further comprising an adjuvant.

115. The immunogenic composition of paragraph 114, wherein the adjuvant is an aluminum-based adjuvant.

116. The immunogenic composition of paragraph 114, wherein the adjuvant is an aluminum phosphate.

117. The immunogenic composition of paragraph 114, wherein the adjuvant is an aluminum hydroxide.

118. A container filled with any of the immunogenic composition defined at any of one of paragraphs 107 to 117.

119. The container of paragraph 118 selected from the group consisting of a vial, a syringe, a flask, a fermentor, a bioreactor, a bag, a jar, an ampoule, a cartridge and a disposable pen.

120. A method of making a glycoconjugate comprising a saccharide conjugated to a carrier protein through a (((2-oxoethyl)thio)alkyl)carbamate (oxo-eTAC) spacer, comprising the steps of:
   a) reacting a saccharide with a carbonic acid derivative or cyanogen derivative, to produce an activated saccharide;
   b) reacting the activated saccharide with a bifunctional linker containing amine and thiol functionalities or a salt thereof, to produce a thiolated saccharide;
   c) reacting the thiolated saccharide with a deprotecting or reducing agent to produce an activated thiolated saccharide comprising one or more free sulfhydryl residues;
   d) reacting the activated thiolated saccharide with an activated carrier protein comprising one or more α-haloacetamide groups, to produce a thiolated saccharide-carrier protein conjugate; and
   e) reacting the thiolated saccharide-carrier protein conjugate with (i) a first capping reagent capable of capping unconjugated α-haloacetamide groups of the activated carrier protein; and/or (ii) a second capping reagent capable of capping unconjugated free sulfhydryl residues of the activated thiolated saccharide;
   whereby an oxo-eTAC linked glycoconjugate is produced 121. The method of paragraph 120, wherein the carbonic acid derivative of step a) is 1,1'-carbonyl-di-(1,2,4-triazole) (CDT) or 1,1'-carbonyldiimidazole (CDI) or disuccinimidyl carbonate (DSC) or N-hydroxysuccinimidyl chloroformate.

122. The method of paragraph 121, wherein the carbonic acid derivative of step a) is 1,1'-carbonyl-di-(1,2,4-triazole) (CDT).

123. The method of anyone of paragraphs 120 to 122, wherein step a) is done in an organic solvent.

124. The method of paragraph 123, wherein said organic solvent is a polar aprotic solvent, such as dimethylsulfoxide (DMSO).

125. The method of anyone of paragraphs 120 to 124, wherein the thiolated saccharide is produced by reaction of the activated saccharide with a heterobifunctional thioalkylamine reagent or a salt thereof.

126. The method of anyone of paragraphs 120 to 125, wherein the first capping reagent is N-acetyl-L-cysteine.

127. The method of anyone of paragraphs 120 to 126, wherein the second capping reagent is iodoacetamide (IAA).

128. The method of anyone of paragraphs 120 to 127, wherein step e) comprises capping with both a first capping reagent and a second capping reagent.

129. The method of anyone of paragraphs 120 to 125, wherein step e) comprises capping with N-acetyl-L-cysteine as the first capping reagent and IAA as the second capping reagent.

130. The method of anyone of paragraphs 120 to 129, wherein the capping step e) further comprises reaction with a reducing agent, for example, DTT, TCEP, or mercaptoethanol, after reaction with the first and/or second capping reagent.

131. The method of anyone of paragraphs 120 to 129, wherein step d) further comprises providing an activated carrier protein comprising one or more α-haloacetamide groups prior to reacting the activated thiolated saccharide with the activated carrier protein.

132. The method of anyone of paragraphs 131, wherein the activated carrier protein comprises one or more α-bromoacetamide groups.

133. The method of anyone of paragraphs 120 to 132, wherein said activated carrier protein is activated CRM197 carrier protein comprising one or more α-bromoacetamide groups.

134. A method of making a glycoconjugate comprising a saccharide conjugated to a carrier protein through an (((2-oxoethyl)thio)alkyl)amine (oxo-eTAAN) spacer, comprising the steps of:
  a) reacting a saccharide with an oxidizing reagent to generate aldehyde groups to produce an activated saccharide;
  b) reacting the activated saccharide with a bifunctional linker containing amine and thiol functionalities (in protected or free forms) from the amino end of the linker, to produce a thiolated saccharide by reductive amination;
  c) reacting the thiolated saccharide with a deprotecting agent or reducing agent (if thiol is protected) to produce an activated thiolated saccharide comprising one or more free sulfhydryl residues;
  d) reacting the activated thiolated saccharide with an activated carrier protein comprising one or more α-haloacetamide groups, to produce a thiolated saccharide-carrier protein conjugate; and
  e) reacting the thiolated saccharide-carrier protein conjugate with (i) a first capping reagent capable of capping unconjugated α-haloacetamide groups of the activated carrier protein; and/or (ii) a second capping reagent capable of capping unconjugated free sulfhydryl residues of the activated thiolated saccharide;
  whereby an oxo-eTAAN linked glycoconjugate is produced.

135. The method of paragraph 134 wherein the saccharide of step a) is oxidized by 2,2,6,6-Tetramethyl-1-piperidinyloxy (TEMPO)/N-Chlorosuccinimide (NCS) reagent system.

136. A method of making a comprising a carboxyl containing saccharide conjugated to a carrier protein through an (((2-oxoethyl)thio)alkyl)amide (oxo-eTAAD) spacer, comprising the steps of:
  a) first reacting the carboxyl group containing saccharide to generated an activated saccharide with a carbodiimide or a derivative thereof;
  b) reacting the activated saccharide with a heterobifunctional linker containing amine and thiol functionalities (in protected or free form) from the amino end, to produce a thiolated saccharide;
  c) reacting the thiolated saccharide with a deprotecting or reducing agent (if protected) to produce an activated thiolated saccharide comprising one or more free sulfhydryl residues;
  d) reacting the activated thiolated saccharide with an activated carrier protein comprising one or more α-haloacetamide groups, to produce a thiolated saccharide-carrier protein conjugate; and
  e) reacting the thiolated saccharide-carrier protein conjugate with (i) a first capping reagent capable of capping unconjugated α-haloacetamide groups of the activated carrier protein; and/or (ii) a second capping reagent capable of capping unconjugated free sulfhydryl residues of the activated thiolated saccharide;
  whereby an oxo-eTAAD linked glycoconjugate is produced.

137. The method of paragraph 136 wherein the carbodiimide derivative is 1-ethyl-3-(3-dimethylaminopropyl)carbodiimide (EDC), or N,N'-dicyclohexylcarbodiimide (DCC), or 1-cyclohexyl-3-(2-morpholinoethyl)carbodiimide.

138. The method of paragraph 136 wherein the carbodiimide derivative is 1-ethyl-3-(3-dimethylaminopropyl)carbodiimide (EDC).

139. The method of anyone of paragraphs 136 to 138, wherein step a) is done in an organic solvent.

140. The method of paragraph 139, wherein said organic solvent is a polar aprotic solvent, such as dimethylsulfoxide (DMSO).

141. The method of anyone of paragraphs 136 to 140 wherein the carboxylic acid activation step a) is accomplished by carbodiimide and thiazolidinone thione.

142. The method of anyone of paragraphs 136 to 140 wherein the carboxylic acid activation step a) is accomplished by N-ethyl-3-phenylisoxazolium-3'-sulfonate (Woodward's reagent K).

143. The method of anyone of paragraphs 120 to 142, further comprising purification of the thiolated polysaccharide produced in step c), wherein the purification step comprises diafiltration.

144. The method of any one of paragraphs 120 to 143, wherein the carrier protein is activated with an activated bromoacetic acid derivative.

145. The method of paragraph 144, wherein the bromoacetic acid derivative is the N-hydroxysuccinimide ester of bromoacetic acid (BAANS).

146. The method of any one of paragraphs 120 to 145, wherein the method further comprises purification of the glycoconjugate by diafiltration.

147. The method of any one of paragraphs 120 to 146, wherein step a) is conducted in a polar aprotic solvent selected from the group consisting of dimethyl sulfoxide (DMSO), dimethylformamide (DMF), dimethylacetamide (DMA), N-methyl-2-pyrrolidone (NMP), acetonitrile, 1,3-Dimethyl-3,4,5,6-tetrahydro-2(1H)-pyrimidinone (DMPU) and hexamethylphosphoramide (HMPA), or a mixture thereof.

148. The method of any one of paragraphs 120 to 147, wherein the saccharide:carrier protein ratio (w/w) is between 0.2 and 4.

149. The method of paragraph 148, wherein the saccharide:carrier protein ratio (w/w) is between 0.4 and 1.7.

150. The method of any one of paragraphs 120 to 149, wherein the saccharide is a capsular polysaccharide derived from *S. pneumoniae*.

151. The method of paragraph 150, wherein the capsular polysaccharide is selected from the group consisting of pneumococcal (Pn) serotype 1, 3, 4, 5, 6A, 6B, 7F, 8, 9V, 10A, 11A, 12F, 14, 15B, 18C, 19A, 19F, 22F, 23F and 33F capsular polysaccharides.

152. The method of paragraph 150, wherein the capsular polysaccharide is a Pn-serotype 33F capsular polysaccharide.

153. The method of paragraph 150, wherein the capsular polysaccharide is a Pn-serotype 22F capsular polysaccharide.

154. The method of paragraph 150, wherein the capsular polysaccharide is a Pn-serotype 10A capsular polysaccharide.

155. The method of paragraph 150, wherein the capsular polysaccharide is a Pn-serotype 11A capsular polysaccharide.

156. The method of any one of paragraphs 120 to 149, wherein the saccharide is a capsular polysaccharide derived from *N. meningitidis*.

157. The method of any one of paragraphs 120 to 156, wherein the carrier protein is $CRM_{197}$.

158. A glycoconjugate produced by the method of any one of paragraphs 120 to 157.

159. An immunogenic composition comprising the glycoconjugate of paragraph 158 and a pharmaceutically acceptable excipient, carrier or diluent.

160. The immunogenic composition of paragraph 159 further comprising an adjuvant.

161. The immunogenic composition of paragraph 160, wherein the aluminum-based adjuvant is selected from the group consisting of aluminum phosphate, aluminum sulfate, and aluminum hydroxide 162. A method of preventing, treating or ameliorating a bacterial infection, disease or condition in a subject, comprising administering to the subject an immunologically effective amount of an immunogenic composition of any one of paragraphs 107 to 117 or 159 to 161.

163. A method of inducing a protective immune response in a subject, comprising administering to the subject an immunologically effective amount of an immunogenic composition of any one of paragraphs 107 to 117 or 159 to 161.

164. The glycoconjugates of anyone of paragraph 1 to 106 or the immunogenic composition of any one of paragraphs 107 to 117 or 159 to 161 for use as a medicament.

165. The glycoconjugates of anyone of paragraph 1 to 106 or the immunogenic composition of any one of paragraphs 107 to 117 or 159 to 161 for use as a vaccine.

166. The glycoconjugates of anyone of paragraph 1 to 106 or the immunogenic composition of any one of paragraphs 107 to 117 or 159 to 161 for use in a method of preventing, treating or ameliorating a bacterial infection, disease or condition in a subject.

167. The glycoconjugates of anyone of paragraph 1 to 106 or the immunogenic composition of any one of paragraphs 107 to 117 or 159 to 161 for use in a method of preventing, a bacterial infection in a subject.

The above disclosure generally describes the present invention. A more complete understanding can be obtained by reference to the following specific examples. These examples are described solely for the purpose of illustration and are not intended to limit the scope of the invention.

EXAMPLES

Example 1. General Process for Preparation of eTEC Linked Glycoconjugates Activation of Saccharide and Thiolation with Cystamine Dihydrochloride The saccharide is reconstituted in anhydrous dimethylsulfoxide (DMSO). Moisture content of the solution is determined by Karl Fischer (KF) analysis and adjusted to reach a moisture content of 0.1 and 0.4%, typically 0.2%.

To initiate the activation, a solution of 1,1'-carbonyl-di-1,2,4-triazole (CDT) or 1,1'-carbonyldiimidazole (CDI) is freshly prepared at a concentration of 100 mg/mL in DMSO. The saccharide is activated with various amounts of CDT/CDI (1-10 molar equivalents) and the reaction is allowed to proceed for 1 hour at 23±2° C. The activation level may be determined by HPLC. Cystamine dihydrochloride is freshly prepared in anhydrous DMSO at a concentration of 50 mg/mL. The activated saccharide is reacted with 1 mol. eq. of cystamine dihydrochloride. Alternatively, the activated saccharide is reacted with 1 mol. eq. of cysteamine hydrochloride. The thiolation reaction is allowed to proceed for 21±2 hours at 23±2° C., to produce a thiolated saccharide. The thiolation level is determined by the added amount of CDT/CDI.

Residual CDT/CDI in the activation reaction solution is quenched by the addition of 100 mM sodium tetraborate, pH 9.0 solution. Calculations are performed to determine the added amount of tetraborate and to adjust the final moisture content to be up to 1-2% of total aqueous.

Reduction and Purification of Activated Thiolated Saccharide

The thiolated saccharide reaction mixture is diluted 10-fold by addition to pre-chilled 5 mM sodium succinate in 0.9% saline, pH 6.0 and filtered through a 5 μm filter. Diafiltration of thiolated saccharide is performed against 40-fold diavolume of WFI. To the retentate a solution of tris(2-carboxyethyl)phosphine (TCEP), 1-5 mol. eq., is added after dilution by 10% volume of 0.1M sodium phosphate buffer, pH 6.0. This reduction reaction is allowed to proceed for 20±2 hours at 5±3° C. Purification of the activated thiolated saccharide is performed preferably by ultrafiltration/dialfiltration of against pre-chilled 10 mM sodium phosphate monobasic, pH 4.3. Alternatively, the thiolated saccharide is purified by standard size exclusion chromatographic (SEC) procedures or ion exchange chromatographic methods. An aliquot of activated thiolated saccharide retentate is pulled to determine the saccharide concentration and thiol content (Ellman) assays.

Alternative Reduction and Purification of Activated Thiolated Saccharide

As an alternative to the purification procedure described above, activated thiolated saccharide was also purified as below.

To the thiolated saccharide reaction mixture a solution of tris(2-carboxyethyl)phosphine (TCEP), 5-10 mol. eq., was added and allowed to proceed for 3±1 hours at 23±2° C. The reaction mixture was then diluted 5-fold by addition to pre-chilled 5 mM sodium succinate in 0.9% saline, pH 6.0 and filtered through a 5 μm filter. Dialfiltration of thiolated saccharide was performed using 40-fold diavolume of pre-chilled 10 mM sodium phosphate monobasic, pH 4.3. An aliquot of activated thiolated saccharide retentate was pulled to determine the saccharide concentration and thiol content (Ellman) assays.

Activation and Purification of Bromoacetylated Carrier Protein

Free amino groups of the carrier protein are bromoacteylated by reaction with a bromoacetylating agent, such as bromoacetic acid N-hydroxysuccinimide ester (BAANS), bromoacetylbromide, or another suitable reagent.

The carrier protein (in 0.1M Sodium Phosphate, pH 8.0±0.2) is first kept at 8±3° C., at about pH 7 prior to activation. To the protein solution, the N-hydroxysuccinimide ester of bromoacetic acid (BAANS) as a stock dimethylsulfoxide (DMSO) solution (20 mg/mL) is added in a ratio of 0.25-0.5 BAANS: protein (w/w). The reaction is gently mixed at 5±3° C. for 30-60 minutes. The resulting bromoacetylated (activated) protein is purified, e.g., by ultrafiltration/diafiltration using 10 kDa MWCO membrane using 10 mM phosphate (pH 7.0) buffer. Following purification, the protein concentration of the bromoacetylated carrier protein is estimated by Lowry protein assay.

The extent of activation is determined by total bromide assay by ion-exchange liquid chromatography coupled with suppressed conductivity detection (ion chromatography). The bound bromide on the activated bromoacetylated protein is cleaved from the protein in the assay sample preparation and quantitated along with any free bromide that may be present. Any remaining covalently bound bromine on the protein is released by conversion to ionic bromide by heating the sample in alkaline 2-mercaptoethanol.

Activation and Purification of Bromoacetylated $CRM_{197}$ $CRM_{197}$ was diluted to 5 mg/mL with 10 mM phosphate buffered 0.9% NaCl pH 7 (PBS) and then made 0.1 M $NaHCO_3$ pH 7.0 using 1 M stock solution. BAANS was added at a $CRM_{197}$: BAANS ratio 1:0.35 (w:w) using a BAANS stock solution of 20 mg/mL DMSO. The reaction mixture was incubated at between 3° C. and 11° C. for 30 mins-1 hour then purified by ultrafiltration/diafiltration using a 10K MWCO membrane and 10 mM Sodium Phosphate/0.9% NaCl, pH 7.0. The purified activated $CRM_{197}$ was assayed by the Lowry assay to determine the protein concentration and then diluted with PBS to 5 mg/mL. Sucrose was added to 5% wt/vol as a cryoprotectant and the activated protein was frozen and stored at −25° C. until needed for conjugation.

Bromoacetylation of lysine residues of $CRM_{197}$ was very consistent, resulting in the activation of 15 to 25 lysines from 39 lysines available. The reaction produced high yields of activated protein.

Conjugation of Activated Thiolated Saccharide to Bromoacetylated Carrier Protein Before starting the conjugation reaction, the reaction vessels are pre-cooled to 5° C. Bromoacetylated carrier protein and activated thiolated saccharide are subsequently added and mixed at an agitation speed of 150-200 rpm. The saccharide/protein input ratio is 0.9±0.1. The reaction pH is adjusted to 8.0±0.1 with 1 M NaOH solution. The conjugation reaction is allowed to proceed at 5° C. for 20±2 hours.

Capping of Residual Reactive Functional Groups

The unreacted bromoacetylated residues on the carrier protein are quenched by reacting with 2 mol. eq. of N-acetyl-L-cysteine as a capping reagent for 3 hours at 5° C. Residual free sulfhydryl groups are capped with 4 mol. eq. of iodoacetamide (IAA) for 20 hours at 5° C.

Purification of eTEC-Linked Glycoconjugate

The conjugation reaction (post-IAA-capped) mixture is filtered through 0.45 μm filter. Ultrafiltration/diafiltration of the glycoconjugate is performed against 5 mM succinate-0.9% saline, pH 6.0. The glycoconjugate retentate is then filtered through 0.2 μm filter. An aliquot of glycoconjugate is pulled for assays. The remaining glycoconjugate is stored at 5° C.

Example 2. Preparation of Pn-33F eTEC Conjugates Activation Process

Activation of Pn33F Polysaccharide

Pn-33F polysaccharide was compounded with 500 mM of 1,2,4-triazole (in WFI) to obtain 10 grams of triazole per gram of polysaccharide. The mixture was shell-frozen in dry ice-ethanol bath and then lyophilized to dryness. The lyophilized 33F polysaccharide was reconstituted in anhydrous dimethylsulfoxide (DMSO). Moisture content of the lyophilized 33F/DMSO solution was determined by Karl Fischer (KF) analysis. The moisture content was adjusted by adding WFI to the 33F/DMSO solution to reach a moisture content of 0.2%.

To initiate the activation, 1,1'-carbonyl-di-1,2,4-triazole (CDT) was freshly prepared as 100 mg/mL in DMSO solution. Pn33F polysaccharide was activated with various amounts of CDT prior to the thiolation step. The CDT activation was carried out at 23±2° C. for 1 hour. The activation level was determined by HPLC (A220/A205). Sodium tetraborate, 100 mM, pH 9.0 solution was added to quench any residual CDT in the activation reaction solution. Calculations are performed to determine the added amount of tetraborate and to allow the final moisture content to be 1.2% of total aqueous. The reaction was allowed to proceed for 1 hour at 23±2° C.

Thiolation of Activated Pn-33F Polysaccharide

Cystamine-dihydrochloride was freshly prepared in anhydrous DMSO and 1 mol. eq. of cystamine dihydrochloride was added to the activated polysaccharide reaction solution. The reaction was allowed to proceed for 21±2 hours at 23±2° C. The thiolated saccharide solution was diluted 10-fold by addition to pre-chilled 5 mM sodium succinate in 0.9% saline, pH 6.0. The diluted reaction solution was filtered through a 5 μm filter. Dialfiltration of thiolated Pn-33F polysaccharide was carried out with 100K MWCO ultrafilter membrane cassettes, using Water for Injection (WFI).

Reduction and Purification of Activated Thiolated Pn-33F Polysaccharide

To the retentate a solution of tris(2-carboxyethyl)phosphine (TCEP), 5 mol. eq., was added after dilution by 10% volume of 0.1M sodium phosphate buffer, pH 6.0. This reduction reaction was allowed to proceed for 2±1 hours at 23±2° C. Dialfiltration of thiolated 33F polysaccharide was carried out with 100K MWCO ultrafilter membrane cassettes. Diafiltration was performed against pre-chilled 10 mM sodium phosphate, pH 4.3. The thiolated 33F polysaccharide retentate was pulled for both saccharide concentration and thiol (Ellman) assays.

Alternative Reduction and Purification of Activated Thiolated Pn-33F Polysaccharide As an alternative to the purification procedure described above, 33F activated thiolated saccharide was also purified as follows.

To the thiolated saccharide reaction mixture a solution of tris(2-carboxyethyl)phosphine (TCEP), 5 mol. eq., was added and allowed to proceed for 3±1 hours at 23±2° C. The reaction mixture was then diluted 5-fold by addition to pre-chilled 5 mM sodium succinate in 0.9% saline, pH 6.0 and filtered through a 5 μm filter. Dialfiltration of thiolated saccharide was performed using 40-fold diavolume of pre-chilled 10 mM sodium phosphate monobasic, pH 4.3 with 100K MWCO ultrafilter membrane cassettes. The thiolated 33F polysaccharide retentate was pulled for both saccharide concentration and thiol (Ellman) assays.

Conjugation Process

Conjugation of Thiolated Pn33F Polysaccharide to Bromoacetylated $CRM_{197}$

The $CRM_{197}$ carrier protein was activated separately by bromoacetylation, as described in Example 1, and then reacted with the activated Pn-33F polysaccharide for the conjugation reaction. Before starting the conjugation reaction, the reaction vessel was pre-cooled to 5° C. Bromoacetylated $CRM_{197}$ and thiolated 33F polysaccharide were mixed together in a reaction vessel at an agitation speed of 150-200 rpm. The saccharide/protein input ratio was 0.9±0.1. The reaction pH was adjusted to 8.0-9.0. The conjugation reaction was allowed to proceed at 5° C. for 20±2 hours.

Capping of Reactive Groups on Bromoacetylated $CRM_{197}$ and Thiolated Pn33F Polysaccharide The unreacted bromoacetylated residues on $CRM_{197}$ proteins were capped by reacting with 2 mol. eq. of N-acetyl-L-cysteine for 3 hours at 5° C., followed by capping any residual free sulfhydryl groups of the thiolated 33F-polysaccharide with 4 mol. eq. of iodoacetamide (IAA) for 20 hours at 5° C.

Purification of eTEC-Linked Pn-33F Glycoconjugate

The conjugation solution was filtered through a 0.45 μm or 5 μm filter. Dialfiltration of the 33F glycoconjugate was carried out with 300K MWCO ultrafilter membrane cassettes. Diafiltration was performed against 5 mM succinate-0.9% saline, pH 6.0. The Pn-33F glycoconjugate 300K retentate was then filtered through a 0.22 μm filter and stored at 5° C.

Results

The reaction parameters and characterization data for several batches of Pn-33F eTEC glycoconjugates are shown in Table 2. The CDT activation-thiolation with cystamine dihydrochloride generated glycoconjugates having from 63 to 90% saccharide yields and <1% to 13% free saccharides.

TABLE 3

Pn-33F OPA Titers (GMT with 95% CI)

| 33F Pn Conjugate | 0.001 μg | 0.01 μg | 0.1 μg |
|---|---|---|---|
| week 4 | 4 (4, 5) | 37 (17, 82) | 414 (234, 734) |
| week 7 | 8 (5, 13) | 131 (54, 314) | 17567 (9469, 32593) |

Example 3. Preparation of Pn-22F eTEC Conjugates

Activation Process

Activation of Pn-22F Polysaccharide

Pn-22F polysaccharide was compounded with 500 mM of 1,2,4-triazole (in WFI) to obtain 10 grams of triazole per gram of polysaccharide. The mixture was shell-frozen in dry ice-ethanol bath and then lyophilized to dryness. The lyophilized 22F polysaccharide was reconstituted in anhydrous dimethylsulfoxide (DMSO). Moisture content of the lyophilized 22F/DMSO solution was determined by Karl Fischer (KF) analysis. The moisture content was adjusted by adding WFI to the Pn-22F/DMSO solution to reach a moisture content of 0.2%.

To initiate the activation, 1,1'-carbonyl-di-1,2,4-triazole (CDT) was freshly prepared as 100 mg/mL in DMSO solution. Pn-22F polysaccharide was activated with various amounts of CDT followed by thiolation with 1 mol. eq. of cystamine dihydrochloride. The CDT activation was carried out at 23±2° C. for 1 hour. The activation level was determined by HPLC (A220/A205). Sodium tetraborate, 100 mM, pH 9.0 solution was added to quench any residual CDT in the activation reaction solution. Calculations are performed to determine the added amount of tetraborate and to allow the final moisture content to be 1.2% of total aqueous. The reaction was allowed to proceed for 1 hour at 23±2° C.

Thiolation of Activated Pn-22F Polysaccharide

Cystamine-dihydrochloride was freshly prepared in anhydrous DMSO and added to the reaction solution. The reaction was allowed to proceed for 21±2 hours at 23±2° C. The thiolated saccharide solution was diluted 10-fold by addition to pre-chilled 5 mM sodium succinate in 0.9% saline, pH 6.0. The diluted reaction solution was filtered through a 5 μm filter. Dialfiltration of thiolated Pn-22F polysaccharide was carried out with 100K MWCO ultrafilter membrane cassettes, using Water for Injection (WFI).

TABLE 2

Experimental Parameters and Characterization Data of Pn33F eTEC Conjugates

| Conjugate Batch | 33F-1A | 33F-2B | 33F-3C | 33F-4D | 33F-5E | 33F-6F | 33F-7G |
|---|---|---|---|---|---|---|---|
| Activation level (mol of thiol/mol of polysaccharide) | 0.21 | 0.13 | 0.164 | 0.103 | 0.183 | 0.22 | 0.19 |
| Activation level (% Thiol) | 21 | 13 | 16.4 | 10.3 | 18.3 | 22 | 19 |
| Saccharide/Protein (Input) ratio | 0.75 | 1.0 | 0.75 | 1.0 | 1.0 | 0.75 | 0.80 |
| Saccharide yield (%) | 69% | 63% | 71% | 63% | 69% | 82% | 90% |
| Saccharide/Protein Ratio | 1.3 | 1.7 | 1.2 | 1.9 | 1.6 | 1.1 | 1.5 |
| Free Saccharide | 12.9% | 7.7% | 4.4% | 7.2% | 7.3% | <4% | <4% |
| MW by SEC-MALLS (kDa) | 2627 | 2561 | 4351 | 2981 | 3227 | 3719 | 5527 |
| CMCA/CMC | 14.4/0 | 13.4/0 | 6.8/1.9 | 2.7/0.6 | 5.9/0.6 | 8.2/0 | 11.4/0.6 |
| % Kd (≤0.3) | N/A | 85% | 88% | 75% | 68% | 67% | 76% |
| Acetylation level (mol of acetate/mol of polysaccharide) | 0.89 | 1.16 | 0.99 | 0.85 | 0.81 | 0.85 | 1.01 |

OPA Titers of Pn-33F eTEC Glycoconjugates to $CRM_{197}$

Pn-33F OPA titers in mice were determined under standard conditions. OPA titers (GMT with 95% CI) at four and seven weeks are shown in Table 3, demonstrating that the serotype 33F Pn glycoconjugate elicited OPA titers in a murine immunogenicity model.

Reduction and Purification of Activated Thiolated Pn-22F Polysaccharide

To the retentate a solution of tris(2-carboxyethyl)phosphine (TCEP), 5-10 mol. eq., was added after dilution by 10% volume of 0.1 M sodium phosphate buffer, pH 6.0. This reduction reaction was allowed to proceed for 2±1 hours at 23±2° C. Diafiltration of thiolated 22F polysaccharide was carried out with 100K MWCO ultrafilter membrane cassettes. Diafiltration was performed against pre-chilled 10 mM sodium phosphate, pH 4.3. The thiolated 22F polysaccharide retentate was pulled for both saccharide concentration and thiol (Ellman) assays.

Conjugation, Capping and Purification of Pn-22F eTEC Glycoconjugates

Conjugation of the activated thiolated Pn22F polysaccharide to activated $CRM_{197}$, capping, and purification of the Pn-22F eTEC glycoconjugates were performed according to the processes described in Example 2.

Results

Characterization and process data for representative Pn-22F eTEC glycoconjugates to $CRM_{197}$ is provided in Table 4.

TABLE 4

Experimental Parameters and Characterization Data for Pn-22F eTEC conjugates

| | Conjugate Batch | | | |
|---|---|---|---|---|
| | Pn-22F-1A | Pn-22F-1B | Pn-22F-1C | Pn-22F-1D |
| Polysaccharide MW (kDa) | 638.5 kDa | 638.5 kDa | 638.5 kDa | 638.5 kDa |
| Poly Activation | | | | |
| Mol. Eq. of CDT | 0.6 mol. equiv. | 0.9 mol. equiv. | 1.2 mol. equiv. | 1.5 mol. equiv. |
| Mol. Eq. of Thiol | 1 mol. eq of cystamine•2HCl | 1 mol. eq of cystamine•2HCl | 1 mol. eq of cystamine•2HCl | 1 mol. eq of cystamine•2HCl |
| Mol. Eq. of Reductant | 10 mol. eq. of TCEP | 10 mol. eq. of TCEP | 10 mol. eq. of TCEP | 10 mol. eq. of TCEP |
| Yield | 86% | 89% | 71% | 86% |
| Thiol (Activation) level (mol of thiol/mol of polysaccharide) | 0.05 | 0.09 | 0.12 | 0.16 |
| Activation level (% Thiol) | 5 | 9 | 12 | 16 |
| Conjugation to CRM197 | | | | |
| Input Ratio | 0.75 | 0.75 | 0.75 | 0.75 |
| Conjugation Results | | | | |
| Saccharide Yield (%) | 55% | 48% | 56% | 35% |
| Saccharide/Protein Ratio | 1.4 | 1.2 | 1.1 | 1.1 |
| Free Saccharide | 29.7% | 16.8% | 9.1% | 10.1% |
| Free Protein | <1% | <1% | <1% | <1% |
| Mw by SEC-MALLS | 1808 kDa | 1787 kDa | 1873 kDa | 2248 kDa |

TABLE 5

Experimental Parameters and Characterization Data for Pn-10A Glycoconjugates

| | Conjugation Batch | | | | |
|---|---|---|---|---|---|
| | Pn-10A-1 | Pn-10A-2 | Pn-10A-3 | Pn-10A-4 | Pn-10A-5 |
| Saccharide MW (kDa) | 538 | 128 | 128 | 128 | 128 |
| Activation level (mol of thiol/mol of polysaccharide) | 0.13 | 0.18 | 0.29 | 0.34 | 0.43 |
| Activation level (% Thiol) | 13 | 18 | 29 | 34 | 43 |
| Conjugate MW (kDa) | 2510 | 950 | 800 | 909 | 1090 |
| % Yield (saccharide) | 67% | 42% | 53% | 55% | 50% |
| % Free Saccharide | 20 | 4.5 | <4 | <4 | <4 |
| Kd (% ≤ 0.3) | 71% | 36% | 38% | 35% | 37% |
| Free Protein | <1% | <1% | <1% | <1% | <1% |
| CMCA residues | N/A | 9.8 | 14.6 | 15.9 | 18.5 |

Example 4. Preparation of Pn-10A eTEC Conjugates to $CRM_{197}$

Preparation of Pn-10A eTEC Glycoconjugates

Glycoconjugates comprising pneumococcal capsular polysaccharide serotype 10A (Pn-10A) conjugated to $CRM_{197}$ via the eTEC spacer were prepared according to the processes described in Example 2.

Characterization of Pn-10A eTEC Glycoconjugates

Characterization and process data for representative Pn-10A eTEC glycoconjugates to $CRM_{197}$ is provided in Table 5.

Pn-10A OPA Titers

OPA titers against the Pn-10A eTEC conjugate to $CRM_{197}$ in mice were determined under standard conditions. OPA titers as a function of dose are shown in Table 6. The OPA titers were significantly higher for the conjugate in relation to the unconjugated Serotype 10A polysaccharide.

TABLE 6

| Pn-10A OPA Titers (GMT with 95% CI) | | | |
|---|---|---|---|
| 10A Pn Variant | 0.001 µg | 0.01 µg | 0.1 µg |
| Pn-10A eTEC conjugate | 691 (389, 1227) | 1208 (657, 2220) | 3054 (1897, 4918) |

TABLE 6-continued

Pn-10A OPA Titers (GMT with 95% CI)

| 10A Pn Variant | 0.001 µg | 0.01 µg | 0.1 µg |
|---|---|---|---|
| Unconjugated PS | | | 602 (193, 1882) |

Example 5. Preparation of Pn-11A eTEC Conjugates to $CRM_{197}$

Preparation of Pn-11A eTEC Glycoconjugates

Glycoconjugates comprising pneumococcal capsular polysaccharide serotype 11A (Pn-11A) conjugated to $CRM_{197}$ via the eTEC spacer were prepared according to the processes described in Example 2.

Characterization of Pn-11A eTEC Glycoconjugates

Characterization and process data for representative Pn-11A eTEC glycoconjugates to $CRM_{197}$ is provided in Table 7.

TABLE 7

Experimental Parameters and Characterization Data for Pn-11A Glycoconjugates

| | Conjugation Batch | | | |
|---|---|---|---|---|
| | Pn-11A-1A | Pn-11A-1B | Pn-11A-2A | Pn-11A-2B |
| Polysaccharide MW | 113 kDa | 113 kDa | 230 kDa | 230 kDa |
| Mol. Eq of CDT | 5 | 5 | 2 | 2 |
| Mol. Eq of Thiol | 0.25 | 0.07 | 1 | 1 |
| Mol. Eq of TCEP | 10 | 10 | 10 | 10 |
| Yield | 62% | 51% | 86% | 82% |
| Activation Level (mol of thiol/mol of polysaccharide) | 0.46 | 0.14 | 0.13 | 0.10 |
| Activation level (% Thiol) | 46 | 14 | 13 | 10 |
| Conjugation to $CRM_{197}$ | | | | |
| Saccharide/Protein Input Ratio | 0.75 | 0.75 | 0.75 | 0.75 |
| Saccharide Yield | 46.4% | 60.4% | 73.3% | 73.9% |
| Saccharide/Protein Ratio | 0.96 | 1.9 | 1.18 | 1.23 |
| Free Saccharide | <4% | 55% | 16% | 23% |
| Free Protein | <1% | <1% | <1% | <1% |
| MW by SEC-MALLS (kDa) | 1203 | 1074 | 1524 | 1884 |

Pn-11A OPA Titers

OPA titers against the Pn-11A eTEC conjugate to $CRM_{197}$ in mice were determined under standard conditions. OPA titers as a function of dose are shown in Table 8.

TABLE 8

Pn-11A OPA Titers (GMT with 95% CI)

| 11A Pn Variant | 0.001 µg | 0.01 µg | 0.1 µg |
|---|---|---|---|
| Pn-11A eTEC conjugate | 206 (166, 256) | 906 (624, 1316) | 5019 (3648, 6904) |

Example 6. Preparation of Pn-33F RAC/Aqueous Conjugates to $CRM_{197}$

Preparation of Pn-33F RAC/Aqueous Glycoconjugates

Pn-33F glycoconjugates were prepared using Reductive Amination in Aqueous Phase (RAC/Aqueous), which has been successfully applied to produce pneumococcal conjugate vaccine (see e.g. WO 2006/110381). This approach includes two steps. The first step is oxidation of polysaccharide to generate aldehyde functionality from vicinal diols. The second step is to conjugate activated polysaccharide to the lysine (Lys) residues of $CRM_{197}$. Briefly, frozen polysaccharide was thawed and oxidation was carried out in sodium phosphate buffer at pH 6.0 by the addition of different amount of sodium periodate (NaIO4). Concentration and diafiltration of the activated polysaccharide was carried out and the purified activated polysaccharide was stored at 4° C. Activated polysaccharide was compounded with $CRM_{197}$ protein. Thoroughly mixing polysaccharide and $CRM_{197}$ is conducted before placing the bottle in dry ice/ethanol bath, followed by lyophilization of the polysaccharide/$CRM_{197}$ mixture. The lyophilized mixture was reconstituted in 0.1 M sodium phosphate buffer. Conjugation reaction was initiated by the addition of 1.5 molar equivalents of sodium cyanoborohydride and incubation for 20 hrs at 23° C. and additional 44 hrs at 37° C. The reactions were diluted with 1× volume of 0.9% saline and capped using 2 MEq of sodium borohydride for 3 hrs at 23° C. The reaction mixture was diluted with 1× volume of 0.9% saline and then filtered through 0.45 µm filter prior to purification. Concentration and diafiltration of the conjugate was carried out using 100K MWCO UF membrane cassettes.

Several conjugates were obtained using the above described process by varying different parameters (e.g. pH, temperature of the reactions and concentration of polysaccharide).

The typical polysaccharide yield was approximately 50% for these conjugates and 15% of free saccharide with conjugate MW in the range 2000-3500 kDa.

However, native serotype 33F polysaccharide bears an O-Acetyl group on its C2 of 5-galactofuranosyl residue and it was found that ~80% of the acetyl functional group is removed throughout conjugation process using Reductive Amination in Aqueous Phase. It was observed that the O-Acetyl group on the five member ring structure (5-galactofuranoside) can migrate and be removed with ease using Reductive Amination Chemistry in Aqueous Phase process.

Evaluation of Pn-33F RAC/Aqueous Glycoconjugate Stability

Aliquots of representative RAC/Aqueous conjugate prepared by the above process were dispensed into polypropylene tubes. These tubes were stored either at 25° C. or at 37° C. and stability was monitored up to 3.5 months. At each stability time point, % free saccharide levels were evaluated. The stability data at both temperatures are summarized in Table 9. As shown in Table 9, the % free saccharide levels increased significantly at 25° C. and 37° C. Increase in % free saccharide levels during storage is a potential indicator for polysaccharide degradation in the conjugate.

TABLE 9

Stability Data for RAC/Aqueous Conjugate at 25° C. and 37° C.

| | Time | | | |
|---|---|---|---|---|
| Lot# | 0 | 2 wks | 1 M | 3.5 Ms |
| Free Saccharide (%) at 25° C. | | | | |
| 1-B | 8.5 | 14 | 14 | 20 |

TABLE 9-continued

Stability Data for RAC/Aqueous Conjugate at 25° C. and 37° C.

| Lot# | Time | | | |
|---|---|---|---|---|
| | 0 | 2 wks | 1 M | 3.5 Ms |
| Free Saccharide (%) at 37° C. | | | | |
| 1-B | 8.5 | 17 | 21 | 38 | wk = week;
M = month.

Although, serotype 33F polysaccharide was successfully activated by the reaction with sodium periodate and subsequently conjugated to $CRM_{197}$ exploiting aqueous reductive amination chemistry, the % free saccharide stability results under accelerated conditions combined with the inability to preserve the acetyl functionality (a key polysaccharide epitope for immunogenicity) during conjugation suggested that the RAC/aqueous process is not the optimal process for serotype 33F conjugation.

Example 7. Preparation of Pn-33F RAC/DMSO Conjugates to $CRM_{197}$

Preparation of Pn-33F RAC/DMSO Glycoconjugates

Compared to RAC/aqueous process, conjugation conducted via reductive amination in an DMSO (RAC/DMSO) generally has a significantly lower chance of de-O-acetylation. In view of the challenges associated with the preservation of O-acetyl functionality using RAC/aqueous process described in Example 6, an alternative approach using RAC/DMSO solvent, which has been successfully applied to produce pneumococcal conjugate vaccine (see e.g. WO 2006/110381) was evaluated.

Activated polysaccharide was compounded with sucrose (50% w/v in WFI) using a ratio of 25 grams of sucrose per gram of activated polysaccharide. The components were well mixed prior to shell freezing in dry ice/ethanol bath. The shell-frozen bottle of compounded mixture was then lyophilized to dryness.

Lyophilized activated polysaccharide was reconstituted in dimethyl sulfoxide (DMSO). DMSO was added to lyophilized $CRM_{197}$ for reconstitution. Reconstituted activated polysaccharide was combined with reconstituted $CRM_{197}$ in the reaction vessel. Conjugation was initiated by adding NaCNBH3 to the reaction mixture. The reaction was incubated at 23° C. for 20 hrs. Termination of the conjugation (capping) reaction was achieved by adding NaBH4 and the reaction was continued for another 3 hrs. The reaction mixture was diluted with 4-fold volume of 5 mM succinate-0.9% saline, pH 6.0 buffer and then filtered through 5 μm filter prior to purification. Concentration and diafiltration of the conjugate was carried out using 100K MWCO membranes. Diafiltration was performed against 40-fold diavolume of 5 mM succinate-0.9% saline, pH 6.0 buffer. The retentate was filtered through 0.45 and 0.22 μm filters and analyzed.

Several conjugates were obtained using the above described process by varying different parameters (e.g. saccharide-protein input ratio, reaction concentration, Meq of sodium cyanoborohydride, and water content). The overall data generated from conjugates prepared by RAC/DMSO process were demonstrated to be superior compared to RAC/aqueous process and allowed to prepare conjugates with good conjugation yield, low % free saccharide (<5%) and higher degree of conjugation (conjugated lysines). Additionally, it was possible to preserve more than 80% of acetyl functionality throughout the RAC/DMSO conjugation process.

Evaluation of Pn-33F RAC/DMSO Glycoconjugates Stability

Aliquots of representative RAC/DMSO conjugates prepared by the above process were dispensed into polypropylene tubes, which were stored either at 4° C. or at 25° C. and stability was monitored for 3 months for free saccharide. As shown at Table 10, the samples stored at 4° C. showed free saccharide increase by 4.8% in 3 months. However the samples stored at 25° C. showed 15.4% increase in the % free saccharide in three months. The increase in % Free Saccharide in the RAC conjugates is attributed to the degradation of the conjugate, particularly at 25° C.

TABLE 10

Stability Results for RAC/DMSO Conjugate at 4° C. and 25° C.

| Time | | | |
|---|---|---|---|
| 0 | 3 wks | 2 M | 3 M |
| Free Saccharide (%) at 4° C. | | | |
| 4.5 | 7.9 | NA | 9.3 |
| Free Saccharide (%) at 25° C. | | | |
| 4.5 | 12 | 15.7 | 19.9 | wk = week;
M = month.

The stability of another lot of RAC/DMSO conjugate was also studied at 4° C., 25° C. and 37° C. Aliquots were dispensed into polypropylene tubes and monitored for potential trends in % free saccharide. As shown at Table 11 the samples stored at 4° C. showed 4.7% increase in % free saccharide in 2 months. The increase in free saccharide was significantly higher at 25° C. and 37° C., indicating potential degradation of the conjugate.

TABLE 11

Stability Results for RAC/DMSO Conjugate at 4° C., 25° C. and 37° C.

| Time | | | | |
|---|---|---|---|---|
| 0 | 1 wk | 2 wks | 1 M | 2 M |
| Free Saccharide (%) at 4° C. | | | | |
| 7.1 | 9.5 | NA | NA | 11.7 |
| Free Saccharide (%) at 25° C. | | | | |
| 7.1 | 9.3 | 12.7 | 14.5 | NA |
| Free Saccharide (%) at 37° C. | | | | |
| 7.1 | 14 | 19.1 | 23.6 | NA | wk = week;
M = month.

Even though the conjugates generated by the RAC/DMSO process preserved the O-Acetyl group, the increase in % free saccharide observed, particularly at 25° C. and above indicated potential instability using this route. In view of this observation of potential instability of RAC/DMSO conjugates, RAC/DMSO was not seen as optimal for serotype 33F conjugation and an alternative chemistry route was developed to generate more stable conjugates (the eTEC conjugates).

Example 8. Preparation of Additional Pn-33F eTEC Conjugates

Additional Pn-33F eTEC Conjugates were generated using the process described in Example 2. The reaction parameters and characterization data for these additional batches of Pn-33F eTEC glycoconjugates are shown in Table 12.

TABLE 12

Experimental Parameters and Characterization Data of further Pn33F eTEC Conjugates

| Conjugate Batch | 33F-8H | 33F-9I | 33F-10J | 33F-11K | 33F-12L | 33F-13M | 33F-14N | 33F-15O | 33F-16P |
|---|---|---|---|---|---|---|---|---|---|
| Activation level (mol of thiol/mol of polysaccharide) | 0.22 | 0.11 | 0.11 | 0.13 | 0.14 | 0.13 | 0.06 | 0.13 | 0.11 |
| Saccharide/Protein (Input) ratio | 0.75 | 0.8 | 0.8 | 0.8 | 0.8 | 0.8 | 0.8 | 0.8 | 0.8 |
| Saccharide yield (%) | 78% | 88% | 89% | 67% | 69% | 86% | 81% | 91% | 88% |
| Saccharide/Protein Ratio | 1.0 | 2.2 | 2.1 | 1.4 | 1.4 | 1.4 | 2.2 | 1.9 | 1.9 |
| Free Saccharide | <1% | 6.8% | 5.9% | 2.3% | 3.6% | LOQ | 8.2% | 3.6% | 6.6% |
| MW by SEC-MALLS (kDa) | 4729 | 3293 | 3295 | 2246 | 2498 | 5539 | 3070 | 6009 | 3789 |
| CMCA/CMC | 6.6/LOQ | 14.2/2.1 | 15.4/2.1 | 5.5/1 | 5.4/1.1 | NA/LOQ | 1.7/1.2 | 4.1/12.2 | 2.2/1.2 |
| % Kd (≤0.3) | 69% | NA | NA | NA | NA | 88% | 87% | 87% | 85% |
| Acetylation level (mol of acetate/mol of polysaccharide) | 0.86 | 0.93 | 0.87 | 1.01 | 0.99 | 0.71 | 0.78 | 0.8 | 0.82 |

LOQ = limit of quantitation.

As shown above and in Table 12, several Pn33F conjugates were obtained using the eTEC conjugation above. The eTEC chemistry allowed preparation of conjugates with high yield, low % free saccharide and high degree of conjugation (conjugated lysines). Additionally, it was possible to preserve more than 80% of acetyl functionality using the eTEC conjugation process.

Example 9. Evaluation of Pn-33F eTEC Glycoconjugates Stability: % Free Saccharide Trends Aliquots of conjugate batch 33F-2B (see table 2) were dispensed into polypropylene tubes and stored at 4° C., 25° C., and 37° C., respectively and monitored for trends in % free saccharide. The data (% free saccharide) are shown in Table 13. As shown in this Table, there were no significant changes in the % free saccharide.

TABLE 13

% Free Saccharide Stability for Pn-33F eTEC Glycoconjugate at 4° C., 25° C. and 37° C.

| | Free Saccharide (%) Time | | | | | |
|---|---|---|---|---|---|---|
| Lot# | 0 | 1 wk | 3 wks | 1 M | 2 M | 3 M | 6 M |
| | 4° C. | | | | | | |
| 33F-2B | 7.7 | NA | 8.3 | NA | 9.7 | 11.2 | 13 |
| | 25° C. | | | | | | |
| | 7.7 | NA | 10.8 | NA | 11.8 | NA | NA |
| | 37° C. | | | | | | |
| | 7.7 | 12.1 | NA | 13.4 | NA | NA | NA | wk = week;
M = month.

The accelerated stability of another conjugate lot (Batch 33F-3C) was also conducted at 37° C. up to 1 month. As shown in Table 14, there was no significant change to % free saccharide at 37° C., up to 1 month.

TABLE 14

% Free Saccharide Stability for Pn-33F eTEC Glycoconjugate at 37° C.

| | Free Saccharide (%) Time | | | | |
|---|---|---|---|---|---|
| Lot# | 0 | 1 day | 1 wk | 2 wks | 1 M |
| | | | 37° C. | | |
| 33F-3C | 4.4 | 5.9 | 6.4 | 7.1 | 7.2 |

To further confirm the stability of eTEC conjugates, additional conjugate batches (33F-3C and 33F-5E (see Table 2 and Table 12)) stored at 4° C. were monitored up to approximately one year, for potential trends in % free saccharide. As shown in Table 15, there were no significant changes in % free saccharide levels for the conjugates stored at 4° C. for an extended period up to approximately one year.

TABLE 15

% Free Saccharide Stability Results for Pn-33F eTEC Glycoconjugates at 4° C.

| | Free Saccharide (%) Time | | | | |
|---|---|---|---|---|---|
| Lot# | 0 | 3 M | 4 M | 12 M | 14 M |
| | | | 4° C. | | |
| 33F-3C | 4.4 | NA | 5.3 | NA | 7.6 |
| 33F-5E | 7.3 | 6.3 | NA | 7.4 | NA |

M = month

In contrast to the RAC/aqueous and RAC/DMSO conjugates, the Serotype 33F conjugates generated by 33F eTEC chemistry were demonstrated to be significantly more stable without noticeable degradation as monitored by the free saccharide trends at various temperatures (real time and accelerated).

Example 10. General Process for Preparation of (((2-oxoethyl)thio)alkyl)carbamate (oxo-eTAC) Linked Glycoconjugate Activation of Saccharide and Thiolation with Mercaptopropionylhydrazide (MPH) Spacer The saccharide is reconstituted in anhydrous dimethylsulfoxide (DMSO). Moisture content of the solution is determined by Karl Fischer (KF) analysis and adjusted to reach a moisture content of 0.1 and 0.4%, typically 0.2%.

To initiate the activation, a solution of 1,1'-carbonyl-di-1,2,4-triazole (CDT) or 1,1'-carbonyldiimidazole (CDI) is freshly prepared at a concentration of 100 mg/mL in DMSO. The saccharide is activated with various amounts of CDT/CDI (1-10 molar equivalents) and the reaction is allowed to proceed for 1 hour at 23±2° C. The activation level may be determined by HPLC. MPH is freshly prepared in anhydrous DMSO at a concentration of 50 mg/mL. The activated saccharide is reacted with 1-3 mol. eq. of MPH. The thiolation reaction is allowed to proceed for 21±2 hours at 23±2° C., to produce a thiolated saccharide. The thiolation level is determined by the added amount of CDT/CDI.

Residual CDT/CDI in the activation reaction solution is quenched by the addition of 100 mM sodium tetraborate, pH 9.0 solution. Calculations are performed to determine the added amount of tetraborate and to adjust the final moisture content to be up to 1-2% of total aqueous.

Purification of Activated Thiolated Saccharide

To the thiolated saccharide reaction mixture a solution of tris(2-carboxyethyl)phosphine (TCEP), 1-5 mol. eq., is added and allowed to proceed for 3±1 hours at 23±2° C. The reaction mixture is then diluted 5-fold by addition to pre-chilled 5 mM sodium succinate in 0.9% saline, pH 6.0 and filtered through a 5 μm filter. Dialfiltration of thiolated saccharide is performed using 40-fold diavolume of pre-chilled 10 mM sodium phosphate monobasic, pH 4.3. An aliquot of activated thiolated saccharide retentate is pulled to determine the saccharide concentration and thiol content (Ellman) assays.

Activation and Purification of Bromoacetylated Carrier Protein

Free amino groups of the carrier protein are bromoactey-lated by reaction with a bromoacetylating agent, such as bromoacetic acid N-hydroxysuccinimide ester (BAANS), bromoacetylbromide, or another suitable reagent.

The carrier protein (in 0.1M Sodium Phosphate, pH 8.0±0.2) is first kept at 8±3° C., at about pH 7 prior to activation. To the protein solution, the N-hydroxysuccinimide ester of bromoacetic acid (BAANS) as a stock dimethylsulfoxide (DMSO) solution (20 mg/mL) is added in a ratio of 0.25-0.5 BAANS: protein (w/w). The reaction is gently mixed at 5±3° C. for 30-60 minutes. The resulting bromoacetylated (activated) protein is purified, e.g., by ultrafiltration/diafiltration using 10 kDa MWCO membrane using 10 mM phosphate (pH 7.0) buffer. Following purification, the protein concentration of the bromoacetylated carrier protein is estimated by Lowry protein assay.

The extent of activation is determined by total bromide assay by ion-exchange liquid chromatography coupled with suppressed conductivity detection (ion chromatography). The bound bromide on the activated bromoacetylated protein is cleaved from the protein in the assay sample preparation and quantitated along with any free bromide that may be present. Any remaining covalently bound bromine on the protein is released by conversion to ionic bromide by heating the sample in alkaline 2-mercaptoethanol.

Activation and Purification of Bromoacetylated $CRM_{197}$ $CRM_{197}$ is diluted to 5 mg/mL with 10 mM phosphate buffered 0.9% NaCl pH 7 (PBS) and then made 0.1 M $NaHCO_3$ pH 7.0 using 1 M stock solution. BAANS is added at a $CRM_{197}$: BAANS ratio 1:0.35 (w:w) using a BAANS stock solution of 20 mg/mL DMSO. The reaction mixture is incubated at between 3° C. and 11° C. for 30 mins-1 hour then purified by ultrafiltration/diafiltration using a 10K MWCO membrane and 10 mM Sodium Phosphate/0.9% NaCl, pH 7.0. The purified activated $CRM_{197}$ is assayed by the Lowry assay to determine the protein concentration and then diluted with PBS to 5 mg/mL. Sucrose is added to 5% wt/vol as a cryoprotectant and the activated protein is frozen and stored at −25° C. until needed for conjugation.

Bromoacetylation of lysine residues of $CRM_{197}$ is very consistent, resulting in the activation of 15 to 25 lysines from 39 lysines available. The reaction produced high yields of activated protein.

Conjugation of Activated Thiolated Saccharide to Bromoacetylated Carrier Protein Before starting the conjugation reaction, the reaction vessels are pre-cooled to 5±3° C. Bromoacetylated carrier protein and activated thiolated saccharide are subsequently added and mixed at an agitation speed of 150-200 rpm. The saccharide/protein input ratio is 0.9±0.1. The reaction pH is adjusted to 8.0±0.1 with 1 M NaOH solution. The conjugation reaction is allowed to proceed at 5±3° C. for 20±2 hours.

Capping of Residual Reactive Functional Groups

The unreacted bromoacetylated residues on the carrier protein are quenched by reacting with 2 mol. eq. of N-Acetyl-L-Cysteine hydrochloride as a capping reagent for 3 hours at 5±3° C. Residual free sulfhydryl groups are capped with 4 mol. eq. of iodoacetamide (IAA) for 20 hours at 5±3° C.

Purification of Oxo-eTAC-Linked Glycoconjugate

The conjugation reaction (post-IAA-capped) mixture is filtered through 0.45 μm filter. Ultrafiltration/dialfiltration of the glycoconjugate is performed against 5 mM succinate-0.9% saline, pH 6.0. The glycoconjugate retentate is then filtered through 0.2 μm filter. An aliquot of glycoconjugate is pulled for assays. The remaining glycoconjugate is stored at 5±3° C.

Example 11. Preparation of (((2-oxoethyl)thio) alkyl)carbamate (oxo-eTAC) Linked Glycoconjugate Through Activation of Saccharide and Thiolation with L-Cystine Dimethylester Dihydrochloride Spacer The saccharide is reconstituted in anhydrous dimethylsulfoxide (DMSO). Moisture content of the solution is determined by Karl Fischer (KF) analysis and adjusted to reach a moisture content of 0.1 and 0.4%, typically 0.2%.

To initiate the activation, a solution of 1,1'-carbonyl-di-1,2,4-triazole (CDT) or 1,1'-carbonyldiimidazole (CDI) is freshly prepared at a concentration of 100 mg/mL in DMSO. The saccharide is activated with various amounts of CDT/CDI (1-10 molar equivalents) and the reaction is allowed to proceed for 1 hour at 23±2° C. The activation level may be determined by HPLC. L-Cystine dimethylester dihydrochloride is freshly prepared in anhydrous DMSO at a concentration of 50 mg/mL. The activated saccharide is reacted with 1-2 mol. eq. of L-Cystine dimethylester dihydrochloride. The thiolation reaction is allowed to proceed for 21±2 hours at 23±2° C., to produce a thiolated saccharide. The thiolation level is determined by the added amount of CDT/CDI.

Residual CDT/CDI in the activation reaction solution is quenched by the addition of 100 mM sodium tetraborate, pH 9.0 solution. Calculations are performed to determine the added amount of tetraborate and to adjust the final moisture content to be up to 1-2% of total aqueous.

Purification of Activated Thiolated Saccharide

To the thiolated saccharide reaction mixture a solution of tris(2-carboxyethyl)phosphine (TCEP), 5-10 mol. eq., is added and allowed to proceed for 3±1 hours at 23±2° C. The reaction mixture is then diluted 5-fold by addition to pre-chilled 5 mM sodium succinate in 0.9% saline, pH 6.0 and filtered through a 5 μm filter. Dialfiltration of thiolated saccharide is performed using 40-fold diavolume of pre-chilled 10 mM sodium phosphate monobasic, pH 4.3. An aliquot of activated thiolated saccharide retentate is pulled to determine the saccharide concentration and thiol content (Ellman) assays.

Conjugation of Activated Thiolated Saccharide to Bromoacetylated Carrier Protein, Capping and purification of the eTAC conjugate follows the general procedure described in example 10, as above.

Example 12. Preparation of (((2-oxoethyl)thio) alkyl)carbamate (oxo-eTAC) Linked Glycoconjugate Through Activation of Saccharide and Thiolation with 2-(2-Aminoethoxy)Ethane-1-Thiol (AEET) Spacer The saccharide is reconstituted in anhydrous dimethylsulfoxide (DMSO). Moisture content of the solution is determined by Karl Fischer (KF) analysis and adjusted to reach a moisture content of 0.1 and 0.4%, typically 0.2%.

To initiate the activation, a solution of 1,1'-carbonyl-di-1,2,4-triazole (CDT) or 1,1'-carbonyldiimidazole (CDI) is freshly prepared at a concentration of 100 mg/mL in DMSO. The saccharide is activated with various amounts of CDT/CDI (1-10 molar equivalents) and the reaction is allowed to proceed for 1 hour at 23±2° C. The activation level may be determined by HPLC. AEET is freshly prepared in anhydrous DMSO at a concentration of 50 mg/mL. The activated saccharide is reacted with 1-2 mol. eq. of AEET. The thiolation reaction is allowed to proceed for 21±2 hours at 23±2° C., to produce a thiolated saccharide. The thiolation level is determined by the added amount of CDT/CDI.

Residual CDT/CDI in the activation reaction solution is quenched by the addition of 100 mM sodium tetraborate, pH 9.0 solution. Calculations are performed to determine the added amount of tetraborate and to adjust the final moisture content to be up to 1-2% of total aqueous.

Purification of Activated Thiolated Saccharide

To the thiolated saccharide reaction mixture a solution of tris(2-carboxyethyl)phosphine (TCEP), 1-5 mol. eq., is added and allowed to proceed for 3±1 hours at 23±2° C. The reaction mixture is then diluted 5-fold by addition to pre-chilled 5 mM sodium succinate in 0.9% saline, pH 6.0 and filtered through a 5 μm filter. Dialfiltration of thiolated saccharide is performed using 40-fold diavolume of pre-chilled 10 mM sodium phosphate monobasic, pH 4.3. An aliquot of activated thiolated saccharide retentate is pulled to determine the saccharide concentration and thiol content (Ellman) assays.

Conjugation of Activated Thiolated Saccharide to Bromoacetylated Carrier Protein, Capping and purification of the eTAC conjugate follows the general procedure described in example 10, as above.

Example 13. Preparation of (((2-Oxoethyl)Thio) Alkyl)Carbamate (Oxo-eTAC) Linked Glycoconjugate Through Activation of Saccharide and Thiolation with 4-Amino-1-Butanethiol Hydrochloride Spacer The saccharide is reconstituted in anhydrous dimethylsulfoxide (DMSO). Moisture content of the solution is determined by Karl Fischer (KF) analysis and adjusted to reach a moisture content of 0.1 and 0.4%, typically 0.2%.

To initiate the activation, a solution of 1,1'-carbonyl-di-1,2,4-triazole (CDT) or 1,1'-carbonyldiimidazole (CDI) is freshly prepared at a concentration of 100 mg/mL in DMSO. The saccharide is activated with various amounts of CDT/CDI (1-10 molar equivalents) and the reaction is allowed to proceed for 1 hour at 23±2° C. The activation level may be determined by HPLC. 4-Amino-1-butanethiol hydrochloride is freshly prepared in anhydrous DMSO at a concentration of 50 mg/mL. The activated saccharide is reacted with 1-2 mol. eq. of 4-Amino-1-butanethiol hydrochloride. The thiolation reaction is allowed to proceed for 21±2 hours at 23±2° C., to produce a thiolated saccharide. The thiolation level is determined by the added amount of CDT/CDI.

Residual CDT/CDI in the activation reaction solution is quenched by the addition of 100 mM sodium tetraborate, pH 9.0 solution. Calculations are performed to determine the added amount of tetraborate and to adjust the final moisture content to be up to 1-2% of total aqueous.

Purification of Activated Thiolated Saccharide

To the thiolated saccharide reaction mixture a solution of tris(2-carboxyethyl)phosphine (TCEP), 1-5 mol. eq., is added and allowed to proceed for 3±1 hours at 23±2° C. The reaction mixture is then diluted 5-fold by addition to pre-chilled 5 mM sodium succinate in 0.9% saline, pH 6.0 and filtered through a 5 μm filter. Dialfiltration of thiolated saccharide is performed using 40-fold diavolume of pre-chilled 10 mM sodium phosphate monobasic, pH 4.3. An aliquot of activated thiolated saccharide retentate is pulled to determine the saccharide concentration and thiol content (Ellman) assays.

Conjugation of Activated Thiolated Saccharide to Bromoacetylated Carrier Protein, Capping and purification of the eTAC conjugate follows the general procedure described in example 10, as above.

Example 14. Preparation of Pn-33F Oxo-eTAC Conjugates Using Mercaptopropionylhydrazide (MPH)

Activation Process

Activation of Pn33F Polysaccharide with Mercaptopropionylhydrazide (MPH) Spacer

Pn-33F polysaccharide is compounded with 500 mM of 1,2,4-triazole (in WFI) to obtain 10 grams of triazole per gram of polysaccharide. The mixture is shell-frozen in dry ice-ethanol bath and then lyophilized to dryness. The lyophilized 33F polysaccharide is reconstituted in anhydrous dimethylsulfoxide (DMSO). Moisture content of the lyophilized 33F/DMSO solution is determined by Karl Fischer (KF) analysis. The moisture content is adjusted by adding WFI to the 33F/DMSO solution to reach a moisture content of 0.2%.

To initiate the activation, 1,1'-carbonyl-di-1,2,4-triazole (CDT) is freshly prepared as 100 mg/mL in DMSO solution. Pn33F polysaccharide is activated with various amounts of CDT prior to the thiolation step. The CDT activation is carried out at 23±2° C. for 1 hour. The activation level is determined by HPLC (A220/A205). Sodium tetraborate, 100 mM, pH 9.0 solution is added to quench any residual CDT in the activation reaction solution. Calculations are performed to determine the added amount of tetraborate and to allow the final moisture content to be 1.2% of total aqueous. The reaction is allowed to proceed for 1 hour at 23±2° C.

Thiolation of Activated Pn-33F Polysaccharide

MPH is freshly prepared in anhydrous DMSO and 1-2 mol. eq. of MPH is added to the activated polysaccharide reaction solution. The reaction is allowed to proceed for 21±2 hours at 23±2° C. To the reaction mixture a solution of tris(2-carboxyethyl)phosphine (TCEP), 1-5 mol. eq., is added and allowed to proceed for 3±1 hours at 23±2° C. The reaction mixture is then diluted 5-fold by addition to pre-chilled 5 mM sodium succinate in 0.9% saline, pH 6.0 and filtered through a 5 μm filter. Dialfiltration of thiolated saccharide is performed using 40-fold diavolume of pre-chilled 10 mM sodium phosphate monobasic, pH 4.3 with 100K MWCO ultrafilter membrane cassettes. The thiolated 33F polysaccharide retentate is pulled for both saccharide concentration and thiol (Ellman) assays.

Conjugation Process

Conjugation of Thiolated Pn33F Polysaccharide to Bromoacetylated $CRM_{197}$

The $CRM_{197}$ carrier protein is activated separately by bromoacetylation, and then reacted with the activated Pn-33F polysaccharide for the conjugation reaction. Before starting the conjugation reaction, the reaction vessel is pre-cooled to 5±3° C. Bromoacetylated $CRM_{197}$ and thiolated 33F polysaccharide were mixed together in a reaction vessel at an agitation speed of 150-200 rpm. The saccharide/protein input ratio is 0.9±0.1. The reaction pH is adjusted to 8.0-9.0. The conjugation reaction is allowed to proceed at 5±3° C. for 20±2 hours.

Capping of Reactive Groups on Bromoacetylated $CRM_{197}$ and Thiolated Pn33F Polysaccharide The unreacted bromoacetylated residues on $CRM_{197}$ proteins were capped by reacting with 2 mol. eq. of N-Acetyl-L-Cysteine hydrochloride for 3 hours at 5±3° C., followed by capping any residual free sulfhydryl groups of the thiolated 33F-polysaccharide with 4 mol. eq. of iodoacetamide (IAA) for 20 hours at 5±3° C.

Purification of Oxo-eTAC-Linked Pn-33F Glycoconjugate

The conjugation solution is filtered through a 0.45 μm or 5 μm filter. Dialfiltration of the 33F glycoconjugate is carried out with 300K MWCO ultrafilter membrane cassettes. Diafiltration is performed against 5 mM succinate-0.9% saline, pH 6.0. The Pn-33F glycoconjugate 300K retentate is then filtered through a 0.22 μm filter and stored at 5±3° C.

Example 15. Preparation of Pn-33F Oxo-eTAC Conjugates Using L-Cystine Dimethylester Activation Process Activation of Pn33F Polysaccharide with L-Cystine Dimethylester Dihydrochloride Spacer Pn-33F polysaccharide was compounded with 500 mM of 1,2,4-triazole (in WFI) to obtain 10 grams of triazole per gram of polysaccharide. The mixture was shell-frozen in dry ice-ethanol bath and then lyophilized to dryness. The lyophilized 33F polysaccharide was reconstituted in anhydrous dimethylsulfoxide (DMSO). Moisture content of the lyophilized 33F/DMSO solution was determined by Karl Fischer (KF) analysis. The moisture content was adjusted by adding WFI to the 33F/DMSO solution to reach a moisture content of 0.2%.

To initiate the activation, 1,1'-carbonyl-di-1,2,4-triazole (CDT) was freshly prepared as 100 mg/mL in DMSO solution. Pn33F polysaccharide was activated with various amounts of CDT prior to the thiolation step. The CDT activation was carried out at 23±2° C. for 1 hour. The activation level was determined by HPLC (A220/A205). Sodium tetraborate, 100 mM, pH 9.0 solution was added to quench any residual CDT in the activation reaction solution. Calculations were performed to determine the added amount of tetraborate and to allow the final moisture content to be 1.2% of total aqueous. The reaction was allowed to proceed for 1 hour at 23±2° C.

Thiolation of Activated Pn-33F Polysaccharide

L-Cystine dimethylester dihydrochloride was freshly prepared in anhydrous DMSO and 1 mol. eq. of L-Cystine dimethylester dihydrochloride was added to the activated polysaccharide reaction solution. The reaction was allowed to proceed for 21±2 hours at 23±2° C. The thiolated saccharide solution was diluted 10-fold by addition to pre-chilled 5 mM sodium succinate in 0.9% saline, pH 6.0. The diluted reaction solution was filtered through a 5 μm filter. Dialfiltration of thiolated Pn-33F polysaccharide was carried out with 100K MWCO ultrafilter membrane cassettes, using Water for Injection (WFI).

Reduction and Purification of Activated Thiolated Pn-33F Polysaccharide

To the retentate a solution of tris(2-carboxyethyl)phosphine (TCEP), 5 mol. eq., was added after dilution by 10% volume of 0.1M sodium phosphate buffer, pH 6.0. This reduction reaction was allowed to proceed for 2±1 hours at 23±2° C. Dialfiltration of thiolated 33F polysaccharide was carried out with 100K MWCO ultrafilter membrane cassettes. Diafiltration was performed against pre-chilled 10 mM sodium phosphate, pH 4.3. The thiolated 33F polysaccharide retentate was pulled for both saccharide concentration and thiol (Ellman) assays.

Alternative Reduction and Purification of Activated Thiolated Pn-33F Polysaccharide As an alternative to the purification procedure described above, 33F activated thiolated saccharide was also purified as follows.

To the thiolated saccharide reaction mixture a solution of tris(2-carboxyethyl)phosphine (TCEP), 5 mol. eq., was added and allowed to proceed for 3±1 hours at 23±2° C. The reaction mixture was then diluted 5-fold by addition to pre-chilled 5 mM sodium succinate in 0.9% saline, pH 6.0 and filtered through a 5 μm filter. Dialfiltration of thiolated saccharide was performed using 40-fold diavolume of pre-chilled 10 mM sodium phosphate monobasic, pH 4.3 with 100K MWCO ultrafilter membrane cassettes. The thiolated 33F polysaccharide retentate was pulled for both saccharide concentration and thiol (Ellman) assays.

Conjugation Process

Conjugation of Thiolated Pn33F Polysaccharide to Bromoacetylated $CRM_{197}$

The $CRM_{197}$ carrier protein was activated separately by bromoacetylation, and then reacted with the activated Pn-33F polysaccharide for the conjugation reaction. Before starting the conjugation reaction, the reaction vessel was pre-cooled to 5±3° C. Bromoacetylated $CRM_{197}$ and thiolated 33F polysaccharide were mixed together in a reaction vessel at an agitation speed of 150-200 rpm. The saccharide/protein input ratio was 0.9±0.1. The reaction pH was adjusted to 8.0-9.0. The conjugation reaction was allowed to proceed at 5±3° C. for 20±2 hours.

Capping of Reactive Groups on Bromoacetylated $CRM_{197}$ and Thiolated Pn33F Polysaccharide The unreacted bromoacetylated residues on $CRM_{197}$ proteins were capped by reacting with 2 mol. eq. of Cysteamine hydrochloride for 3 hours at 5±3° C., followed by capping any residual free sulfhydryl groups of the thiolated 33F-polysaccharide with 4 mol. eq. of iodoacetamide (IAA) for 20 hours at 5±3° C.

Purification of Oxo-eTAC-Linked Pn-33F Glycoconjugate

The conjugation solution was filtered through a 0.45 μm or 5 μm filter. Dialfiltration of the 33F glycoconjugate was carried out with 300K MWCO ultrafilter membrane cassettes. Diafiltration was performed against 5 mM succinate-0.9% saline, pH 6.0. The Pn-33F glycoconjugate 300K retentate was then filtered through a 0.22 μm filter and stored at 5±3° C.

Results

Characterization and process data for representative Pn-33F oxo-eTAC conjugates using L-Cystine dimethylester dihydrochloride spacer are provided at Table 16

Example 16. Preparation of Pn-33F oxo-eTAC Conjugates using 2-(2-Aminoethoxy)Ethane-1-Thiol (AEET)

Activation Process

Activation of Pn33F Polysaccharide with 2-(2-Aminoethoxy)Ethane-1-Thiol (AEET) Spacer Pn-33F polysaccharide was compounded with 500 mM of 1,2,4-triazole (in WFI) to obtain 10 grams of triazole per gram of polysaccharide. The mixture was shell-frozen in dry ice-ethanol bath and then lyophilized to dryness. The lyophilized 33F polysaccharide was reconstituted in anhydrous dimethylsulfoxide (DMSO). Moisture content of the lyophilized 33F/DMSO solution was determined by Karl Fischer (KF) analysis. The moisture content was adjusted by adding WFI to the 33F/DMSO solution to reach a moisture content of 0.2%.

To initiate the activation, 1,1'-carbonyl-di-1,2,4-triazole (CDT) was freshly prepared as 100 mg/mL in DMSO solution. Pn33F polysaccharide was activated with various amounts of CDT prior to the thiolation step. The CDT activation was carried out at 23±2° C. for 1 hour. The activation level is determined by HPLC (A220/A205). Sodium tetraborate, 100 mM, pH 9.0 solution was added to quench any residual CDT in the activation reaction solution. Calculations were performed to determine the added amount of tetraborate and to allow the final moisture content to be 1.2% of total aqueous. The reaction was allowed to proceed for 1 hour at 23±2° C.

Thiolation of Activated Pn-33F Polysaccharide

AEET was freshly prepared in anhydrous DMSO and 1-2 mol. eq. of AEET was added to the activated polysaccharide reaction solution. The reaction was allowed to proceed for 21±2 hours at 23±2° C. To the reaction mixture a solution of tris(2-carboxyethyl)phosphine (TCEP), 1-5 mol. eq., was added and allowed to proceed for 3±1 hours at 23±2° C. The reaction mixture was then diluted 5-fold by addition to pre-chilled 5 mM sodium succinate in 0.9% saline, pH 6.0 and filtered through a 5 μm filter. Dialfiltration of thiolated saccharide was performed using 40-fold diavolume of pre-chilled 10 mM sodium phosphate monobasic, pH 4.3 with 100K MWCO ultrafilter membrane cassettes. The thiolated 33F polysaccharide retentate was pulled for both saccharide concentration and thiol (Ellman) assays.

Conjugation Process

Conjugation of Thiolated Pn33F Polysaccharide to Bromoacetylated $CRM_{197}$

The $CRM_{197}$ carrier protein was activated separately by bromoacetylation, and then reacted with the activated Pn-33F polysaccharide for the conjugation reaction. Before starting the conjugation reaction, the reaction vessel was pre-cooled to 5±3° C. Bromoacetylated $CRM_{197}$ and thiolated 33F polysaccharide were mixed together in a reaction vessel at an agitation speed of 150-200 rpm. The saccharide/protein input ratio was 0.9±0.1. The reaction pH is adjusted to 8.0-9.0. The conjugation reaction was allowed to proceed at 5±3° C. for 20±2 hours.

Capping of Reactive Groups on Bromoacetylated $CRM_{197}$ and Thiolated Pn33F Polysaccharide The unreacted bromoacetylated residues on $CRM_{197}$ proteins were capped by reacting with 2 mol. eq. of N-Acetyl-L-Cysteine hydrochloride for 3 hours at 5±3° C., followed by capping any residual free sulfhydryl groups of the thiolated 33F-polysaccharide with 4 mol. eq. of iodoacetamide (IAA) for 20 hours at 5±3° C.

Purification of Oxo-eTAC-Linked Pn-33F Glycoconjugate

The conjugation solution was filtered through a 0.45 μm or 5 μm filter. Dialfiltration of the 33F glycoconjugate was carried out with 300K MWCO ultrafilter membrane cassettes. Diafiltration was performed against 5 mM succinate-0.9% saline, pH 6.0. The Pn-33F glycoconjugate 300K retentate was then filtered through a 0.22 μm filter and stored at 5±3° C.

Results

Characterization and process data for representative Pn-33F oxo-eTAC conjugates using 2-(2-aminoethoxy)ethane-1-thiol (AEET) spacer are provided at Table 16.

Example 17. Preparation of Pn-33F Oxo-eTAC Conjugates Using 4-Amino-1-Butanethiol (ABT)

Activation Process

Activation of Pn33F Polysaccharide with 4-Amino-1-Butanethiol Hydrochloride Spacer Pn-33F polysaccharide was compounded with 500 mM of 1,2,4-triazole (in WFI) to obtain 10 grams of triazole per gram of polysaccharide. The mixture was shell-frozen in dry ice-ethanol bath and then lyophilized to dryness. The lyophilized 33F polysaccharide was reconstituted in anhydrous dimethylsulfoxide (DMSO). Moisture content of the lyophilized 33F/DMSO solution was determined by Karl Fischer (KF) analysis. The moisture content was adjusted by adding WFI to the 33F/DMSO solution to reach a moisture content of 0.2%.

To initiate the activation, 1,1'-carbonyl-di-1,2,4-triazole (CDT) was freshly prepared as 100 mg/mL in DMSO solution. Pn33F polysaccharide was activated with various amounts of CDT prior to the thiolation step. The CDT activation was carried out at 23±2° C. for 1 hour. The activation level was determined by HPLC (A220/A205). Sodium tetraborate, 100 mM, pH 9.0 solution was added to quench any residual CDT in the activation reaction solution. Calculations were performed to determine the added amount of tetraborate and to allow the final moisture content to be 1.2% of total aqueous. The reaction was allowed to proceed for 1 hour at 23±2° C.

Thiolation of Activated Pn-33F Polysaccharide

4-Amino-1-butanethiol hydrochloride was freshly prepared in anhydrous DMSO and 1-2 mol. eq. of 4-Amino-1-butanethiol hydrochloride was added to the activated polysaccharide reaction solution. The reaction was allowed to proceed for 21±2 hours at 23±2° C. To the reaction mixture a solution of tris(2-carboxyethyl)phosphine (TCEP), 1-5 mol. eq., was added and allowed to proceed for 3±1 hours at 23±2° C. The reaction mixture was then diluted 5-fold by addition to pre-chilled 5 mM sodium succinate in 0.9% saline, pH 6.0 and filtered through a 5 μm filter. Dialfiltration of thiolated saccharide was performed using 40-fold diavolume of pre-chilled 10 mM sodium phosphate monobasic, pH 4.3 with 100K MWCO ultrafilter membrane cassettes. The thiolated 33F polysaccharide retentate was pulled for both saccharide concentration and thiol (Ellman) assays.

Conjugation Process

Conjugation of Thiolated Pn33F Polysaccharide to Bromoacetylated $CRM_{197}$

The $CRM_{197}$ carrier protein was activated separately by bromoacetylation, and then reacted with the activated Pn-33F polysaccharide for the conjugation reaction. Before starting the conjugation reaction, the reaction vessel was pre-cooled to 5±3° C. Bromoacetylated $CRM_{197}$ and thiolated 33F polysaccharide were mixed together in a reaction vessel at an agitation speed of 150-200 rpm. The saccharide/protein input ratio is 0.9±0.1. The reaction pH was adjusted to 8.0-9.0. The conjugation reaction was allowed to proceed at 5±3° C. for 20±2 hours.

Capping of Reactive Groups on Bromoacetylated $CRM_{197}$ and Thiolated Pn33F Polysaccharide The unreacted bromoacetylated residues on $CRM_{197}$ proteins were capped by reacting with 2 mol. eq. of N-Acetyl-L-Cysteine hydrochloride for 3 hours at 5±3° C., followed by capping any residual free sulfhydryl groups of the thiolated 33F-polysaccharide with 4 mol. eq. of iodoacetamide (IAA) for 20 hours at 5±3° C.

Purification of Oxo-eTAC-Linked Pn-33F Glycoconjugate

The conjugation solution was filtered through a 0.45 μm or 5 μm filter. Dialfiltration of the 33F glycoconjugate was carried out with 300K MWCO ultrafilter membrane cassettes. Diafiltration was performed against 5 mM succinate-0.9% saline, pH 6.0. The Pn-33F glycoconjugate 300K retentate was then filtered through a 0.22 μm filter and stored at 5±3° C.

Results

Characterization and process data for representative Pn-33F oxo-eTAC conjugates using 4-Amino-1-butanethiol hydrochloride (ABT) spacer are provided at Table 16.

TABLE 16

Experimental Parameters and Characterization Data for Pn-33F eTAC conjugates with various types of linkers

| | Conjugate Batch | | |
|---|---|---|---|
| | Pn-33F-eTAC-AEET (see example 16) | Pn-33F-eTAC-Cystine (see example 15) | Pn-33F-eTAC-ABT (see example 17) |
| Polysaccharide Mw (SEC-MALLS) Poly Activation | 1565 kDa | 1565 kDa | 1565 kDa |
| Meq. of CDT | 3 | 3 | 3 |
| Linker | AEET | Cystine | ABT |
| MEq. of Linker | 1 | 1 | 1 |
| MEq. of TCEP | 5 meq | 5 meq | 5 meq |
| Yield | 80% | 84% | 75% |
| Thiol content (mol of thiol/mol of polysaccharide) Conjugation to $CRM_{197}$ | 0.19 | 0.033 | 0.18 |
| Input ratio Conjugate Results | 0.80 | 0.80 | 0.80 |
| Saccharide yield (%) | 55% | 52% | 52% |
| Saccharide/Protein Ratio | 1.6 | 2.1 | 2.6 |

TABLE 16-continued

Experimental Parameters and Characterization Data for Pn-33F eTAC conjugates with various types of linkers

| | Conjugate Batch | | |
|---|---|---|---|
| | Pn-33F-eTAC-AEET (see example 16) | Pn-33F-eTAC-Cystine (see example 15) | Pn-33F-eTAC-ABT (see example 17) |
| Free Saccharide | 8% | 7% | 7% |
| Free Protein | <1% | <1% | <1% |
| Conjugate Mw (SEC-MALS) | 4518 kDa | 4369 kDa | 3616 kDa |

Polysaccharide-protein conjugates were generated with each of these linkers having good quality attributes including molecular weight, high yield, low free saccharide and low free protein levels.

Example 18. General Process for Preparation of (((2-Oxoethyl)Thio)Alkyl)Amine (Oxo-eTAAN) Linked Glycoconjugate Via Primary Hydroxyl Oxidation Oxidation of Primary Hydroxyl Groups of Polysaccharide Oxidation of primary alcohols in polysaccharide was achieved using the TEMPO/NCS system in either aqueous or organic solvent. The polysaccharides were oxidized to varying degrees of oxidation (DO) levels by adjusting the amount of NCS cooxidant. Generally 0.5-2.5 Molar Equivalents of NCS was used to achieve the target Degree of Oxidation. The oxidation reaction was typically done in bicarbonate/carbonate buffer (0.5 M $NaHCO_3$/0.05 M $Na_2CO_3$ buffer, pH 8.6) or sodium phosphate buffers of pH 6.5, 7.0, 7.5 and 8.0 and is complete in 2 hours. In some activation experiments a primary alcohol such as n-propanol was used to quench the reagents in order to avoid saccharide overoxidation.

In a specific example, the Serotype 33F polysaccharide was added to a reaction vessel at a concentration of 4.0 mg/mL and mixed with bicarbonate/carbonate buffer (0.5 M $NaHCO_3$/0.05 M $Na_2CO_3$ buffer, pH 8.6) at a ratio of 1:1 v/v. To the stirred mixture was added ≤0.1 mol equivalent of TEMPO. The reaction was started by the addition of 0.6 to 1.0 mol equivalent of N-chlorosuccinimide (NCS). The reaction mixture was stirred at room temperature for 2 hours, after which the activated polysaccharide was purified by diafiltration, with WFI using a 30K ultrafiltration membrane. The purified polysaccharide was collected and the degree of oxidation (DO) was determined by quantitative measurements of aldehyde (using a 3-methyl-2-benothiazolinone hydrazone (MBTH) assay) and polysaccharide (using an anthrone assay).

Thiolation of Oxidized Polysaccharide Using Reductive Amination Chemistry

Activation Using 2-(2-Aminoethoxy)Ethane-1-Thiol (AEET) Spacer ($3^{rd}$ Column of Table 17)

The oxidized and purified Serotype 33F polysaccharide was added to a reaction vessel followed by the addition of 0.5 M Sodium phosphate buffer (pH 6.5) to a final buffer concentration of 0.1 M. To this solution, 1 Meq 2-(2-aminoethoxy)ethane-1-thiol ($NH_2$—$CH_2$—$CH_2$—O—$CH_2$—$CH_2$—SH) (AEET) was added and mixed thoroughly in order to obtain a homogenous solution. The pH was adjusted to 6.8 using diluted HCl or 1N NaOH solution. This was followed by the addition of 1.5 molar equivalents of $NaCNBH_3$. The reaction mixture was stirred for 48 hours at room temperature (23° C.). The reaction mixture was then diluted with 1×0.9% saline and the unreacted aldehyde groups were "capped" with 2 molar equivalents of sodium borohydride. The sodium borohydride also functions as a reducing agent for the reduction of any disulfide formed during the reaction. The capping reaction time was typically 3 hours.

Activation Using Cystamine Spacer ($2^{nd}$ Column of Table 17)

The oxidized and purified Serotype 33F polysaccharide was added to a reaction vessel followed by the addition of 0.5 M Sodium phosphate buffer (pH 6.5) to a final buffer concentration of 0.1 M. To this solution, 1 MEq of Cystamine dihydrochloride solution was added and mixed thoroughly in order to obtain a homogenous solution. The pH was adjusted to 6.8 using diluted HCl or 1N NaOH solution. This was followed by the addition of 1.5 molar equivalents of $NaCNBH_3$. The reaction mixture was stirred for 48 hours at room temperature (23° C.). Alternatively the activated saccharide was reacted with 1 MEq of cysteamine hydrochloride. The reaction mixture was then diluted with 1×0.9% saline and the unreacted aldehyde groups were "capped" with 2 molar equivalents of sodium borohydride. The sodium borohydride also functions as a reducing agent for the reduction of any disulfide formed during the reaction. The capping reaction time was typically 3 hours.

Purification of the Activated Thiolated Saccharide

Any remaining disulfide bonds present in the saccharide was reduced using a suitable reducing agent such as (2-carboxyethyl)phosphine (TCEP) or dithioerythritol (DTT). The thiolated saccharide reaction mixture was diluted 10-fold by addition to pre-chilled 5 mM sodium succinate in 0.9% saline, pH 6.0 and filtered through a 5 µm filter. Dialfiltration of thiolated saccharide was performed against 40-fold diavolume of WFI. To the retentate a solution of tris(2-carboxyethyl)phosphine (TCEP), 1-5 mol. eq., was added after dilution by 10% volume of 0.1M sodium phosphate buffer, pH 6.0. This reduction reaction was allowed to proceed for 20±2 hours at 5±3° C. Purification of the activated thiolated saccharide was performed preferably by ultrafiltration/dialfiltration of against pre-chilled 10 mM sodium phosphate monobasic, pH 4.3. Alternatively, the thiolated saccharide was purified by standard size exclusion chromatographic (SEC) procedures or ion exchange chromatographic methods. An aliquot of activated thiolated saccharide retentate was pulled to determine the saccharide concentration and thiol content (Ellman) assays.

In another example, low molecular weight saccharides are used to react with the aminothiol reagent utilizing the reducing end of the saccharide chain. The low molecular weight saccharides are prepared by either chemical hydrolysis or mechanical homogenization of high molecular weight polysaccharides.

Conjugation of Thiolated 33F with Bromoacetylated $CRM_{197}$

Before starting the conjugation reaction, the reaction vessels were pre-cooled to 5±3° C. Bromoacetylated carrier protein and activated thiolated saccharide were subsequently added and mixed at an agitation speed of 150-200 rpm. The saccharide/protein input ratio was 0.9±0.1. The reaction pH was adjusted to 8.0±0.1 with 1 M NaOH solution. The conjugation reaction was allowed to proceed at 5° C. for 20±2 hours. The unreacted bromoacetylated residues on the carrier protein were quenched by reacting with 2 mol. eq. of N-acetyl-L-cysteine as a capping reagent for 3 hours at 5±3° C. Residual free sulfhydryl groups were capped with 4 mol. eq. of iodoacetamide (IAA) for 20 hours at 5±3° C.

The conjugation reaction (post-IAA-capped) mixture was filtered through a 5 µm filter and then purified using 100K MWCO ultra filtration membranes against 5 mM succinate-0.9% saline, pH 6.0. The purified conjugate was then filtered through 0.45/0.22 µm filters to obtain the bulk conjugate.

Results

Characterization and process data for representative Pn-33F eTAAN using either 2-(2-aminoethoxy)ethane-1-thiol (AEET) or cystamine as spacer and conjugated to $CRM_{197}$ are provided at Table 17.

TABLE 17

Experimental Parameters and Characterization Data for Pn-33F eTAAN conjugates

| | Conjugate Batch | |
| --- | --- | --- |
| | Pn-33F-eTAAN-TEMPO-Cystamine | Pn-33F-eTAAN-TEMPO-AEET |
| Polysaccharide Mw (SEC-MALLS) | 1565 kDa | 1565 kDa |
| Poly Oxidation | | |
| TEMPO (% v/v) | 1 | 1 |
| NCS (mol. eq.) | 0.6 | 0.6 |
| Yield | 68% | 68% |
| Oxidized poly Mw (SEC-MALS) | 217 kDa | 217 kDa |
| Degree of Oxidation | 10 | 10 |
| Thiolation | | |
| Linker | Cystamine | AEET |
| NaCNBH3 (mol. eq.) | 1.5 | 1.5 |
| Yield | 19% | 33% |
| Thiol content (mol of thiol/mol of polysaccharide) | 0.09 | 0.09 |
| Conjugation to CRM197 | | |
| Input ratio (SPR) | 0.8 | 0.8 |
| Conjugate Results | | |
| Saccharide yield (%) | 89% | 80% |
| Saccharide/Protein Ratio | 0.96 | 0.85 |
| Free Saccharide | 22% | 13% |
| Conjugate Mw (SEC-MALLS) | 331 kDa | 512 kDa |

Polysaccharide-protein conjugates were generated with each of these linkers having good quality attributes including molecular weight, high yield, low free saccharide levels.

Example 19. General Process for Preparation of (((2-Oxoethyl)Thio)Alkyl)Amine (Oxo-eTAAN) Linked Glycoconjugate Via Oxidation of Vicinal Diols of Polysaccharide Alternatively the saccharides can be activated by oxidizing the vicinal cis diols using periodate. In a specific example, the serotype 33F polysaccharide was dissolved in 100 mM sodium phosphate buffer (pH 6.0) to a final concentration of 2 mg/ml in 25 mM buffer. The reaction was initiated by the addition of 0.2 Meq of sodium periodate (50 mg/mL solution in water). After 18 hours the activated polysaccharide was purified by diafiltration, with WFI using a 30K ultrafiltration membrane. The purified polysaccharide was collected and the degree of oxidation (DO) was determined by quantitative measurements of aldehyde (using a 3-methyl-2-benothiazolinone hydrazone (MBTH) assay) and polysaccharide (using an anthrone assay).

Thiolation of the oxidized polysaccharide and conjugation were carried out by the procedure described in example 18 as described above.

Results

Characterization and process data for representative Pn-33F eTAAN glycoconjugates using either 2-(2-aminoethoxy)ethane-1-thiol (AEET) or cystamine as spacer and conjugated to $CRM_{197}$ are provided in Table 18.

TABLE 18

Experimental Parameters and Characterization Data for Pn-33F eTAAN conjugates

| | Conjugate Batch | |
|---|---|---|
| | Pn-33F-eTAAN-NaIO$_4$-Cystamine | Pn-33F-eTAAN-NaIO$_4$-AEET |
| Polysaccharide Mw (SEC-MALLS) | 1565 kDa | 1565 kDa |
| Poly Oxidation | | |
| NaIO$_4$ (mol. eq.) | 0.14 | 0.14 |
| Yield | 69% | 69% |
| Degree of Oxidation | 12 | 12 |
| Thiolation | | |
| Linker | Cystamine | AEET |
| NaCNBH3 (mol. eq.) | 1.5 | 1.5 |
| Yield | 100% | 100% |
| Thiol content (mol of thiol/mol of polysaccharide) | 0.06 | 0.06 |
| Conjugation to CRM197 | | |
| Input ratio (SPR) | 0.8 | 0.8 |
| Conjugate Results | | |
| Saccharide yield (%) | 56% | 59% |
| Output Ratio (SPR) | 1.9 | 2.2 |
| Free Saccharide | <5% | <5% |
| Free Protein | <1% | <1% |
| Conjugate Mw (SEC-MALLS) | 6324 kDa | 5890 kDa |

Polysaccharide-protein conjugates were generated with each of these linkers having good quality attributes including molecular weight, high yield, low free saccharide and low free protein levels.

Example 20. Process for Preparation of (((2-Oxoethyl)Thio)Alkyl)Amide (Oxo-eTAAD) Linked Glycoconjugate Pn-22F polysaccharide is compounded with 500 mM of 1,2,4-triazole (in WFI) to obtain 10 grams of triazole per gram of polysaccharide. The mixture is shell-frozen in dry ice-ethanol bath and then lyophilized to dryness. The lyophilized Pn-22F polysaccharide is reconstituted in anhydrous dimethylsulfoxide (DMSO). To this solution, cystamine hydrochloride (1.0 meq) is added, followed by 1-(3-dimethylaminopropyl)-3-ethylcarbodiimide hydrochloride (1.1 meq) and HOBt (1.1 meq). The mixture is then stirred for 18±2 hours at 23±2° C. before it is diluted 10-fold by pouring into pre-chilled sodium phosphate buffer, pH 6.0. The diluted solution is filtered through a 5 μm filter. Dialfiltration of derivatized Pn-22F polysaccharide is carried out with 100K MWCO ultrafilter membrane cassettes, against Water for Injection (WFI). The retentate is collected.

Reduction and Purification of Activated Thiolated Pn-22F Polysaccharide

To the retentate a solution of tris(2-carboxyethyl)phosphine (TCEP, 5 mol. eq.), is added after dilution by 10% volume of 0.1M sodium phosphate buffer, pH 6.0. This reduction reaction is allowed to proceed for 2±1 hours at 23±2° C. Dialfiltration of thiolated Pn-22F polysaccharide is carried out with 100K MWCO ultrafilter membrane cassettes. Diafiltration is performed against pre-chilled 10 mM sodium phosphate, pH 4.3. The thiolated Pn-22F polysaccharide retentate is pulled for both saccharide concentration and thiol (Ellman) assays.

Conjugation of Thiolated Pn-22F Polysaccharide to Bromoacetylated $CRM_{197}$

The $CRM_{197}$ carrier protein is activated separately by bromoacetylation, as described in Example 1, and then reacted with the activated Pn-22F polysaccharide for the conjugation reaction. Before starting the conjugation reaction, the reaction vessel is pre-cooled to 5±3° C. Bromoacetylated $CRM_{197}$ and thiolated Pn-22F polysaccharide are mixed together in a reaction vessel at an agitation speed of 150-200 rpm, using a saccharide/protein input ratio of 0.9±0.1. The reaction pH is adjusted to 8.0-9.0. The conjugation reaction is allowed to proceed at 5±3° C. for 20±2 hours.

Capping of Reactive Groups on Bromoacetylated $CRM_{197}$ and Thiolated Pn-22F Polysaccharide The unreacted bromoacetylated residues on $CRM_{197}$ proteins are capped by reacting with 2 mol. eq. of N-acetyl-L-cysteine for 3 hours at 5±3° C., followed by capping any residual free sulfhydryl groups of the thiolated Pn8-polysaccharide with 4 mol. eq. of iodoacetamide (IAA) for 20 hours at 5±3° C.

Purification of eTAAD-Linked Pn-22F Glycoconjugate

The conjugation solution is filtered through a 0.45 μm or 5 μm filter. Dialfiltration of the Pn-22F glycoconjugate is carried out with 100K MWCO ultrafilter membrane cassettes. Diafiltration is performed against 5 mM succinate-0.9% saline, pH 6.0. The Pn-22F glycoconjugate 100K retentate is then filtered through a 0.22 μm filter and stored at 5±3° C.

Example 21. Process for Preparation of (((2-Oxoethyl)Thio)Alkyl)Amide (Oxo-eTAAD) Linked Glycoconjugate Via Thiazolidinone Activation Route Derivatization of Pn-22F Polysaccharide Pn-22F polysaccharide is compounded with 500 mM of 1,2,4-triazole (in WFI) to obtain 10 grams of triazole per gram of polysaccharide. The mixture is shell-frozen in dry ice-ethanol bath and then lyophilized to dryness. The lyophilized Pn-22F polysaccharide is reconstituted in anhydrous dimethylsulfoxide (DMSO). To this solution, thiazolidine-2-thione (TT) (0.3 MEq) and 1-(3-dimethylaminopropyl)-3-ethylcarbodiimide hydrochloride (0.3 meq) solutions in DMSO are added. The mixture is then stirred for 18±2 hours at 23±2° C. To this solution 0.2 MEq cystamine hydrochloride is added and the reaction is continued for another 18 hours. The thiolated polysaccharide is buffer exchanged with water.

To the retentate a solution of tris(2-carboxyethyl)phosphine (TCEP, 5 mol. eq.), is added after dilution by 10% volume of 0.1M sodium phosphate buffer, pH 6.0. This reduction reaction is allowed to proceed for 2±1 hours at 23±2° C. Dialfiltration of thiolated Pn8 polysaccharide is carried out with 100K MWCO ultrafilter membrane cassettes. Diafiltration is performed against pre-chilled 10 mM sodium phosphate, pH 4.3. The thiolated Pn-22F polysaccharide retentate is pulled for both saccharide concentration and thiol (Ellman) assays.

Conjugation of Thiolated Pn-22F Polysaccharide to Bromoacetylated CRM$_{197}$

Conjugation of the Pn-22F thiolated polysaccharide is carried out as outlined in Example 20 above.

All publications and patent applications mentioned in the specification are indicative of the level of those skilled in the art to which this invention pertains. All publications and patent applications are hereby incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

The invention claimed is:

1. A glycoconjugate comprising a saccharide covalently conjugated to a carrier protein through a spacer containing ((2-oxoethyl)thio), wherein said glycoconjugate comprises formula (I):

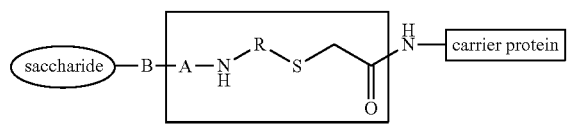

(I)

wherein:
A is a group (C=X)m, wherein X is S or O, and m is 0 or 1;
B is a bond, O, or CH$_2$; and when m is 0, B can also be (C=O);
R is selected from the group consisting of:
(i) O—CH$_2$, O—CH$_2$—CH$_2$, CH$_2$—CH$_2$—O—CH$_2$—CH$_2$, O—CH$_2$—CH$_2$—O—CH$_2$—CH$_2$, O—CH$_2$—CH$_2$—O—CH$_2$—CH$_2$—O—CH$_2$—CH$_2$, O—CH$_2$—CH$_2$—(N—CH$_3$)—CH$_2$—CH$_2$—O—CH$_2$—CH$_2$, CH$_2$—CH$_2$—(N—CH$_3$)—CH$_2$—CH$_2$ and CH$_2$—CH$_2$—S—CH$_2$—CH$_2$;
with the proviso that said spacer is not the (2-((2-oxoethyl)thio)ethyl)carbamate (eTec) spacer.

2. A glycoconjugate comprising formula (III):

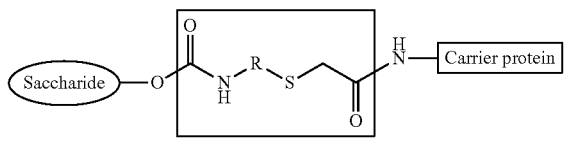

(III)

wherein R is selected from the group consisting of (CH$_2$CH$_2$O)$_m$CH$_2$CH$_2$, CH(COOH)(CH$_2$)$_n$, NHCO(CH$_2$)$_n$, NHCO(CH$_2$CH$_2$O)$_m$CH$_2$CH$_2$, OCH$_2$(CH$_2$)$_n$ and O(CH$_2$CH$_2$O)$_m$CH$_2$CH$_2$;
wherein n is selected from 1 to 10 and m is selected from 1 to 4.

3. The glycoconjugate of claim 1 wherein m is 0 and B is CH$_2$.

4. The glycoconjugate of claim 1 wherein m is 0 and B is C=O.

5. The glycoconjugate of claim 1, wherein the saccharide is a capsular polysaccharide derived from bacteria.

6. The glycoconjugate of claim 5, wherein said capsular polysaccharide is derived from *S. pneumoniae*.

7. The glycoconjugate of claim 6, wherein said capsular polysaccharide is selected from the group consisting of Pn-serotype 1, 2, 3, 4, 5, 6A, 6B, 7F, 8, 9V, 9N, 10A, 11A, 12F, 14, 15A, 15B, 17F, 18C, 19A, 19F, 20, 22F, 23A, 23B, 23F, 33F and 35B capsular polysaccharides.

8. The glycoconjugate of claim 1, wherein the saccharide has a molecular weight of between 10 kDa and 2,000 kDa.

9. The glycoconjugate of claim 1, wherein the glycoconjugate has a molecular weight of between 50 kDa and 20,000 kDa.

10. The glycoconjugate of claim 5, wherein the polysaccharide has a degree of O-acetylation between 75-100%.

11. The glycoconjugate of claim 1, wherein the carrier protein is selected from the group consisting of TT, DT, DT mutants, *H. influenzae* protein D, PhtX, PhtD, PhtE fusions, detoxified pneumolysin, PorB, N19 protein, PspA, OMPC, toxin A or B of *C. difficile*, and PsaA.

12. The glycoconjugate of claim 1, wherein the carrier protein is CRM$_{197}$.

* * * * *

UNITED STATES PATENT AND TRADEMARK OFFICE
CERTIFICATE OF CORRECTION

| | |
|---|---|
| PATENT NO. | : 10,668,164 B2 |
| APPLICATION NO. | : 15/118038 |
| DATED | : June 2, 2020 |
| INVENTOR(S) | : Jianxin Gu |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 88 days.

Signed and Sealed this
Thirty-first Day of January, 2023

Katherine Kelly Vidal
*Director of the United States Patent and Trademark Office*